US012686841B2

(12) United States Patent
Bachoo et al.

(10) Patent No.: US 12,686,841 B2
(45) Date of Patent: Jul. 21, 2026

(54) HIGH THROUGHPUT MIGRATING CELL ISOLATION RETRIEVAL DEVICE AND METHODS OF FABRICATION

(71) Applicant: The Board of Regents of The University of Texas System, Austin, TX (US)

(72) Inventors: Robert M. Bachoo, Southlake, TX (US); Digant P. Davé, Arlington, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 600 days.

(21) Appl. No.: 18/111,697

(22) Filed: Feb. 20, 2023

(65) Prior Publication Data

US 2023/0203416 A1 Jun. 29, 2023

Related U.S. Application Data

(63) Continuation-in-part of application No. PCT/US2021/056210, filed on Oct. 22, 2021.
(Continued)

(51) Int. Cl.
*C12M 1/32* (2006.01)
*B01L 3/00* (2006.01)
(Continued)

(52) U.S. Cl.
CPC ....... *C12M 23/12* (2013.01); *B01L 3/502707* (2013.01); *B01L 3/502761* (2013.01);
(Continued)

(58) Field of Classification Search
None
See application file for complete search history.

(56) References Cited

U.S. PATENT DOCUMENTS 7,858,044 B2 12/2010 Coassin et al.
10,012,640 B2 7/2018 Pant et al.
(Continued)

FOREIGN PATENT DOCUMENTS

JP 2007525647 A 9/2007
JP 2019517808 A 6/2019
WO WO-2019200401 A1 10/2019

OTHER PUBLICATIONS

International Search Report and Written Opinion issued in PCT/ US2021/056210, Mar. 4, 2022, 18 pages.
(Continued)

*Primary Examiner* — Holly Kipouros
(74) *Attorney, Agent, or Firm* — Polsinelli PC

(57) ABSTRACT

A Cell Migration Assay Plates (CMAP) assembly for high throughput microfluidic migration assays and method of manufacturing thereof are provided. The CMAP assembly includes a top plate having a plurality of wells aligned with a trough component having a plurality of troughs. Each of the wells is defined at least in part by first and second reservoirs and a divisional wall extending between the reservoirs. The trough component is secured to the top plate to form a plurality of micro-channels, such that each one of the micro-channels is defined by a portion of one of the divisional walls and a portion of a corresponding one of the plurality of troughs. The micro-channels enable communication between the reservoirs and visualization of cells migrating through the micro-channels. In this manner, migration of cells through the micro-channels can be visualized for testing and screening applications. A sealing component includes a trough gasket which is operable to be positioned against the bottom end of the well such that the sealing component is sandwiched between the divisional wall and the trough component. The trough gasket is operable to retain the plurality of cells within the troughs such
(Continued)

that the plurality of cells migrating towards the second reservoir are isolated within the corresponding trough. At least a portion of the trough component is reconfigurable in relation to the trough gasket and the top plate such that the troughs are exposed to permit a user to retrieve one or more of the cells from the troughs.

27 Claims, 21 Drawing Sheets

Related U.S. Application Data

(60) Provisional application No. 63/104,093, filed on Oct. 22, 2020.

(51) Int. Cl.
C12M 3/00 (2006.01)
C12M 3/06 (2006.01)

(52) U.S. Cl.
CPC ............ *C12M 23/16* (2013.01); *C12M 23/44* (2013.01); *B01L 2200/025* (2013.01); *B01L 2200/0647* (2013.01); *B01L 2200/12* (2013.01); *B01L 2300/0829* (2013.01); *B01L 2300/12* (2013.01)

(56) References Cited

U.S. PATENT DOCUMENTS

| | | | |
|---|---|---|---|
| 10,179,897 B2 | 1/2019 | Hung et al. | |
| 10,435,734 B2 | 10/2019 | Kim et al. | |
| 11,629,319 B2 | 4/2023 | Vulto et al. | |
| 2010/0081768 A1 | 4/2010 | Kizu et al. | |
| 2010/0258198 A1 | 10/2010 | Tonkovich et al. | |
| 2012/0003732 A1 | 1/2012 | Hung et al. | |
| 2014/0370593 A1 | 12/2014 | Achneck et al. | |
| 2015/0247112 A1* | 9/2015 | Orr ....................... | C12M 29/10 |
| | | | 435/395 |
| 2016/0303565 A1 | 10/2016 | Bhagat et al. | |
| 2019/0324028 A1 | 10/2019 | Fan et al. | |
| 2019/0339257 A1 | 11/2019 | Miklas et al. | |
| 2019/0390149 A1* | 12/2019 | Cho ....................... | C12M 23/12 |
| 2020/0063081 A1 | 2/2020 | Vulto et al. | |
| 2024/0368509 A1* | 11/2024 | Jeong ..................... | C12M 29/04 |

OTHER PUBLICATIONS

Dworak, et al., "Novel MEA platform with PDMS microtunnels enables the detection of action potential propagation from isolated axons in culture.", Lab on a Chip 9.3, Nov. 18, 2008, pp. 404-410.
Aghvami, et al., "Rapid prototyping of cyclic olefin copolymer (COC) microfluidic devices." Sensors and Actuators B: Chemical 247, Aug. 1, 2017, pp. 940-949.
Sep. 5, 2024—(EP) Extended European Search Report—App 21883969. 4, 8 Pages.
Nov. 18, 2025—(JP) Office Action—App 2023-519980, 4 Pages.

* cited by examiner

500

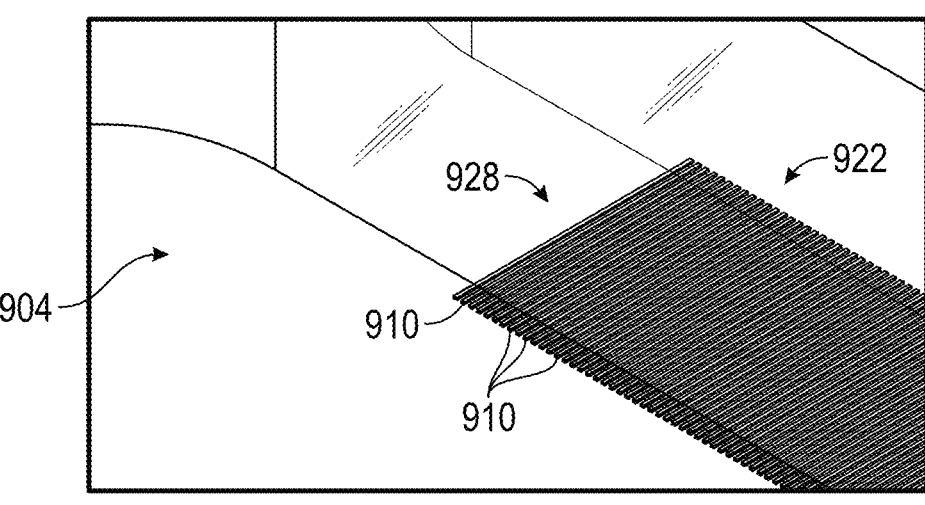
FIG. 10B
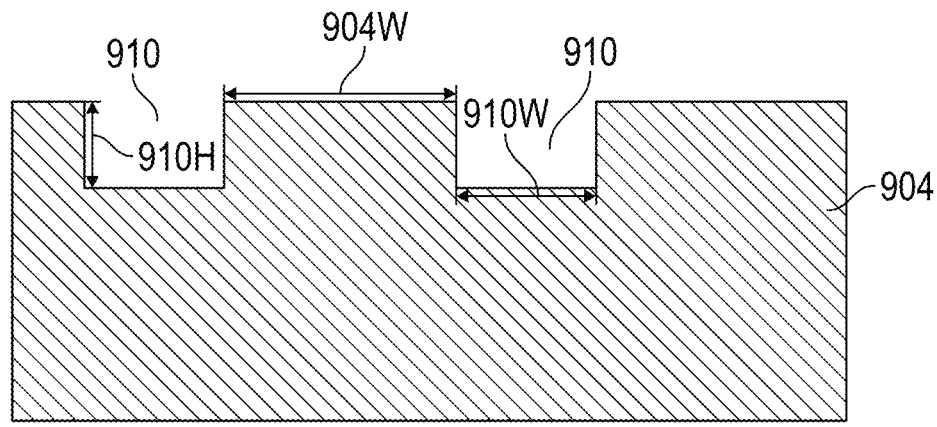
FIG. 10C
FIG. 10D

HIGH THROUGHPUT MIGRATING CELL ISOLATION RETRIEVAL DEVICE AND METHODS OF FABRICATION

CROSS-REFERENCE TO RELATED APPLICATIONS

This application is a continuation-in-part application of PCT/US2021/056210 filed on Oct. 22, 2021, which claims the benefit of U.S. Provisional Patent Application Ser. No. 63/104,093 filed on Oct. 22, 2020, the contents of each incorporated by reference in their entireties.

BACKGROUND

1. Field

The present inventive concept is directed to microfluidic devices for tumor cell migration with high throughput and fabrication methods thereof. The microfluidic devices can be used for tumor drug screening applications.

2. Discussion of Related Art

Conventional migration assays utilize two-dimensional (2D) surfaces for assessing tumor cell migration. In scratch/gap type assays, cells migrate towards an empty space via adhesion-dependent or mesenchymal-mode migration. In transwell assays, such as Boyden chamber, a dense extra-cellular matrix (ECM) and narrow pores are provided, and migration is driven by a chemotactic-gradient across a thin membrane. Neither the scratch/gap type assays nor the transwell assays are able to recapitulate any three-dimensional (3D) migration phenotypes of tumor cells seen in-vivo.

Although some more recent 3D assays, such as a multi-cellular tumor spheroid (MCTS), partially recreate the complex microenvironment of a tumor, such are not suitable for migration studies due to various reasons including that cells do not migrate within a spheroid of the tumor.

Further, commercial micro-channel devices are used in various biological applications. Conventional migration studies are conducted with polydimethylsiloxane (PDMS) based microfluidic devices fabricated using soft lithography. Although the PDMS-based migration devices are suitable for low throughput or proof-of-concept type of experiments, such are unsuitable for producing high density and high-volume migration device arrays with reproducible channel dimensions, which are required for a high-quality clinical assays. Moreover, the porous matrix of PDMS adsorbs drug molecules, making it unusable for drug screening applications.

Accordingly, there is a need to develop apparatuses and associated techniques for high throughput cell migration studies that do not suffer from the aforementioned deficiencies, are adaptable to accommodate a variety of different application requirements, and are efficient, economical, and easy to fabricate and utilize.

BRIEF SUMMARY

The present inventive concept provides multiple Cell Migration Assay Plates (CMAP) assemblies operable to function as high throughput microfluidic device plates for studying cell migration, methods to fabricate the microfluidic device plates and form the CMAP assemblies, and image analysis procedures to quantify cell migration using the CMAP assemblies.

The aforementioned may be achieved in one aspect of the present inventive concept by forming a CMAP assembly defined by a top plate and a bottom plate. The top plate has a plurality of wells arranged in an array with a plurality of columns and a plurality of rows. Each of the wells is defined at least in part by a pair of reservoirs. The bottom plate is a micro-fabricated plate having a plurality of troughs. When the top plate and the bottom plate are joined, a plurality of micro-channels are formed, which are defined by the plurality of troughs and a portion of the top plate. The micro-channels connect respective reservoirs in each of the pair of reservoirs. The top well plate and bottom plate can be manufactured with material and technologies compatible for large scale production with high feature reproducibility. In some embodiments, tumor cells can be seeded in one reservoir of the pair of reservoirs, referred to an input reservoir, while the other reservoir, referred to an output reservoir, is operable to receive the tumor cells after migration through one of the plurality of micro-channels. The micro-channels in the CMAP assembly can be designed to allow single cell migration and/or collective migration of tumor cells. The physical confinement of tumor cells in the micro-channels can trigger a 3D migration phenotype without any chemo-gradient between the two reservoirs. Migrating tumor cells are polarized due to spatial cues provided by the extended troughs and the micro-channels. Migrating cells have a polarity, e.g., a front and a back. Without the polarity, the cells would move in ail directions. With the spatially induced polarity, however, the cells are caused to move forward in the micro-channels. As such, dimensions (L×W×H) of troughs and micro-channels induce the 3D mode of migration and at the same time accomplish the migration assay in a reasonable time frame.

The CMAP assembly provides a 3D migration mode for tumor cells in the micro-channels. The 3D migration mode is similar to in-vivo migration mode. The 3D migration mode is fundamentally different than the 2D mesenchymal mode of migration. The difference in the mode of migration is important to evaluate drug response because the cytoskeleton of the cell undergoes a massive transformation, when a cell migrating on a 2D surface transitions to a 3D confined space. Additionally, the nucleus of the cell dramatically changes shape to facilitate movement in tightly-confined 3D space of the micro-channels. This change in the shape and size of the nucleus can modulate transcription and potentially affect cell cycle progression.

The CMAP assembly creates a physical environment, e.g., of a defined geometrical shape and size, to deliberately and controllably trigger a 3D migration phenotype observed in confined tumor cells. The CMAP assembly enables a user to study tumor cell migration, at a single cell level, without sacrificing any imaging resolution afforded by state-of-the-art microscopic imaging techniques. The CMAP assembly is operable to interrogate migration phenotype of tumor cells without any mechanical or chemical perturbation to cell culture. In contrast, conventional 2D surfaces used in conventional migration assays do not recapitulate 3D micro-environment, e.g., physically or bio-molecularly, of tumor tissue. The entire process of migration can be imaged and quantified in a high throughput plate reader using the CMAP assembly of the present inventive concept.

The disclosure provides different CMAP assemblies, e.g., a large array format and a small array format. In some embodiments, a small array format CMAP assembly, with an array four (4) sets of micro-wells arranged in a 2×2 pattern, has a same size as a standard microscope slide. The small array format CMAP assembly is designed for low through-put basic research applications to study 3D tumor cell migration.

In an embodiment, the large array format CMAP assembly, with an array of ninety-six (96) sets of micro-wells arranged in an 8×12 pattern, is dimensionally of a same size as an industry standard ninety-six (96) well plate for cell culture, with 240 micro-channels per well. One application of the CMAP assembly in the large array format is for high throughput screening of tumor drugs. The CMAP assembly in the large format array can have high throughput, high content imagers/plate readers, and can trigger in-vivo migra-tion phenotype, which is necessary for a robust migration assay screening of a large library of drugs.

Additional aspects, advantages, and utilities of the present inventive concept will be set forth, in part, in the description which follows and, in part, will be obvious from the descrip-tion, or may be learned by practice of the present inventive concept.

The foregoing is intended to be illustrative and is not meant in a limiting sense. Many features and subcombina-tions of the present inventive concept may be made and will be readily evident upon a study of the following specifica-tion and accompanying drawings comprising a part thereof. These features and subcombinations may be employed with-out reference to other features and subcombinations.

BRIEF DESCRIPTION OF THE DRAWINGS

Embodiments of the present inventive concept are illus-trated by way of example in which like reference numerals indicate similar elements and in which.

4

Figure 2A:
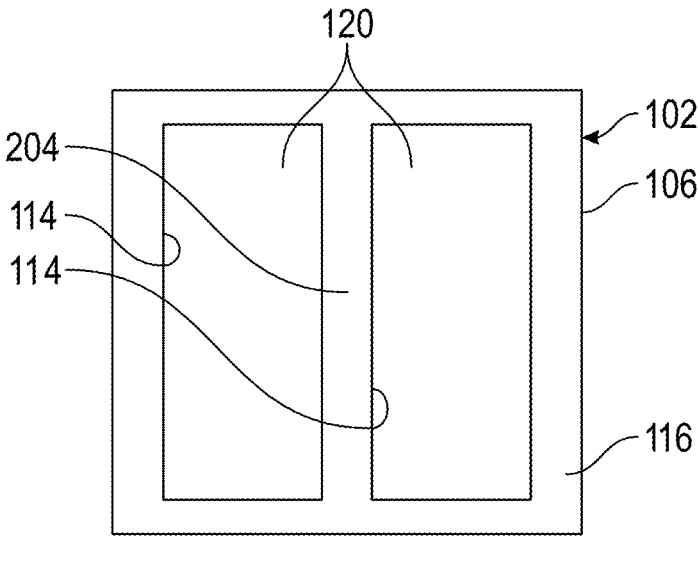
FIG. 2A is a top plan view of a single well of the top plate of FIG. 1A showing two reservoirs prior to assembly of the large format CMAP assembly, in accordance with embodi-ments of the present inventive concept.
Figure 2B:
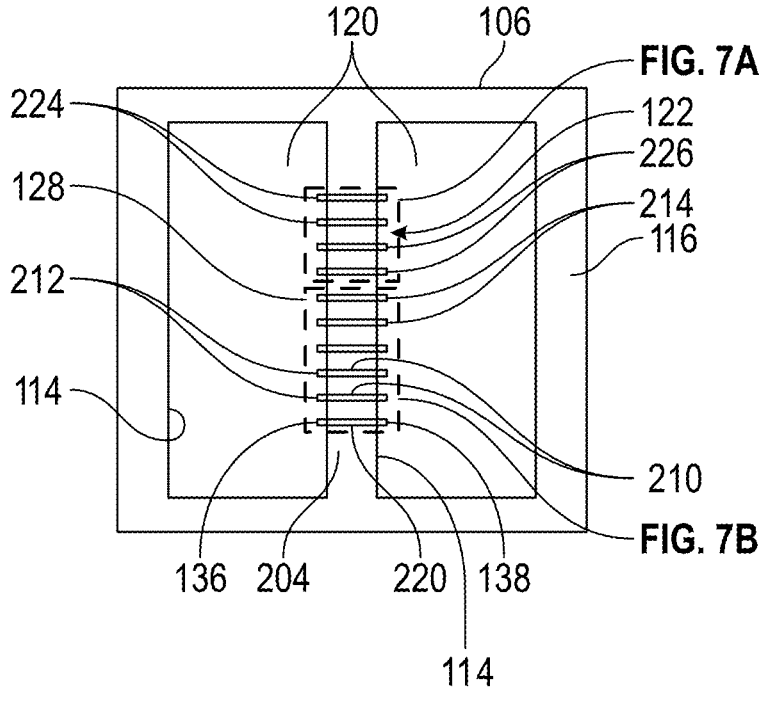
FIG. 2B is a top plan view of a single well of the top plate showing two reservoirs within the single well and a single set of troughs of the bottom plate assembled to form micro-channels, after assembly of the large format CMAP assembly, in accordance with embodiments of the present inventive concept.
Figure 3A:
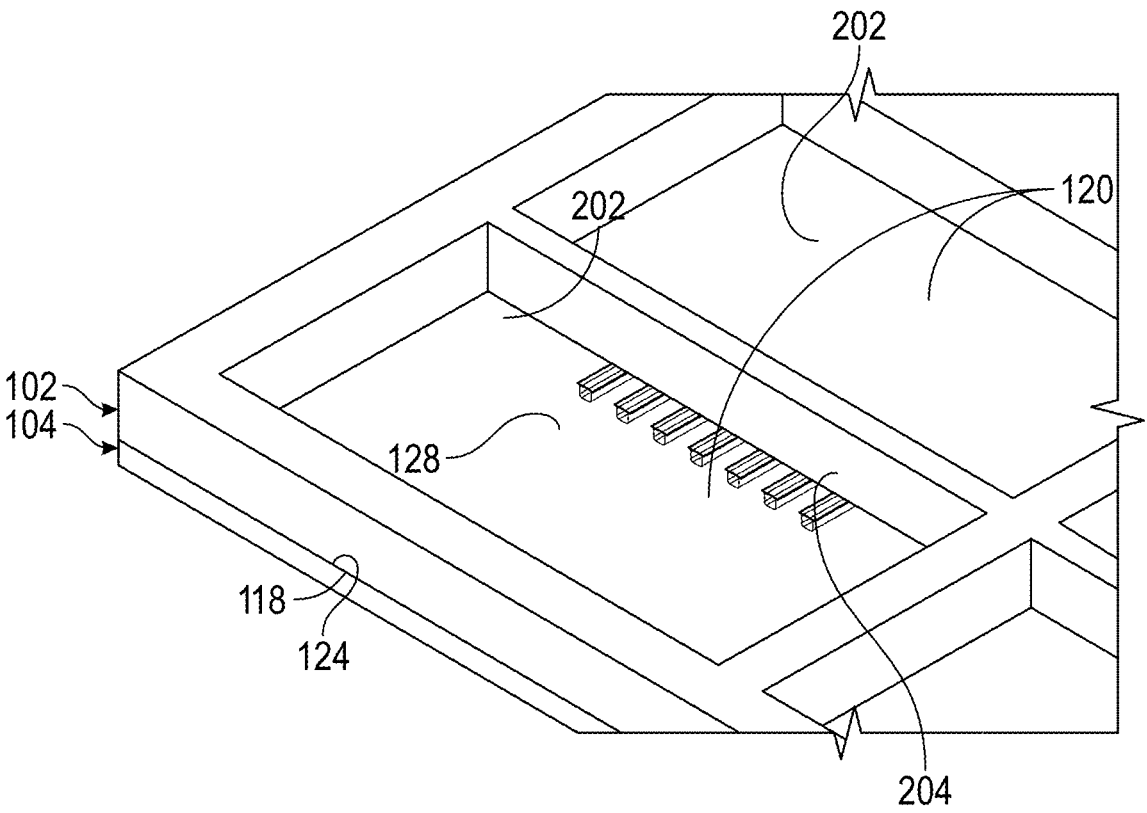
FIG. 3A is a perspective cross-sectional view of the CMAP assembly showing micro-channels formed, upon assembly of the large format CMAP assembly, in accordance with embodiments of the present inventive concept.
Figure 3B:
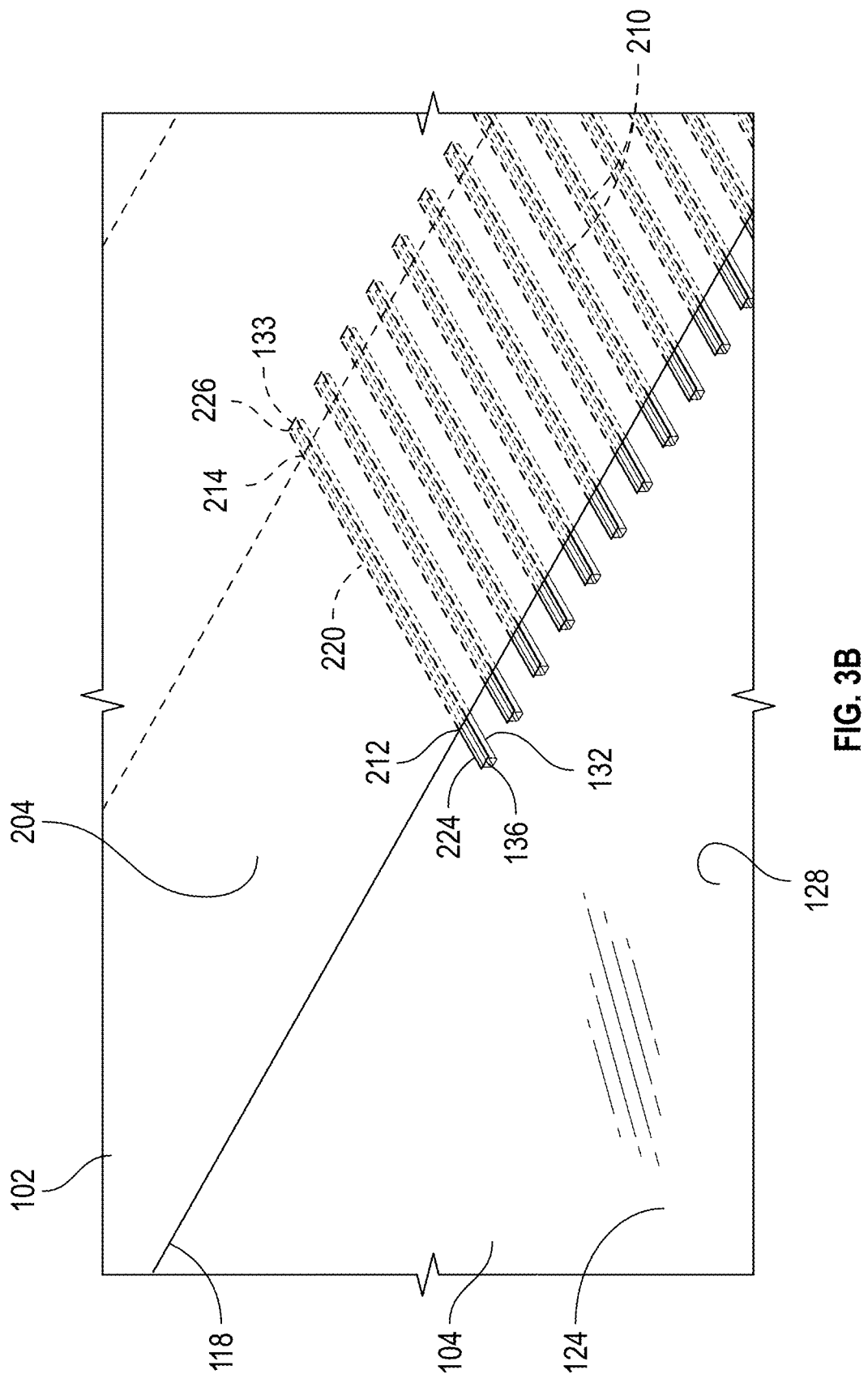
Figure 3C:
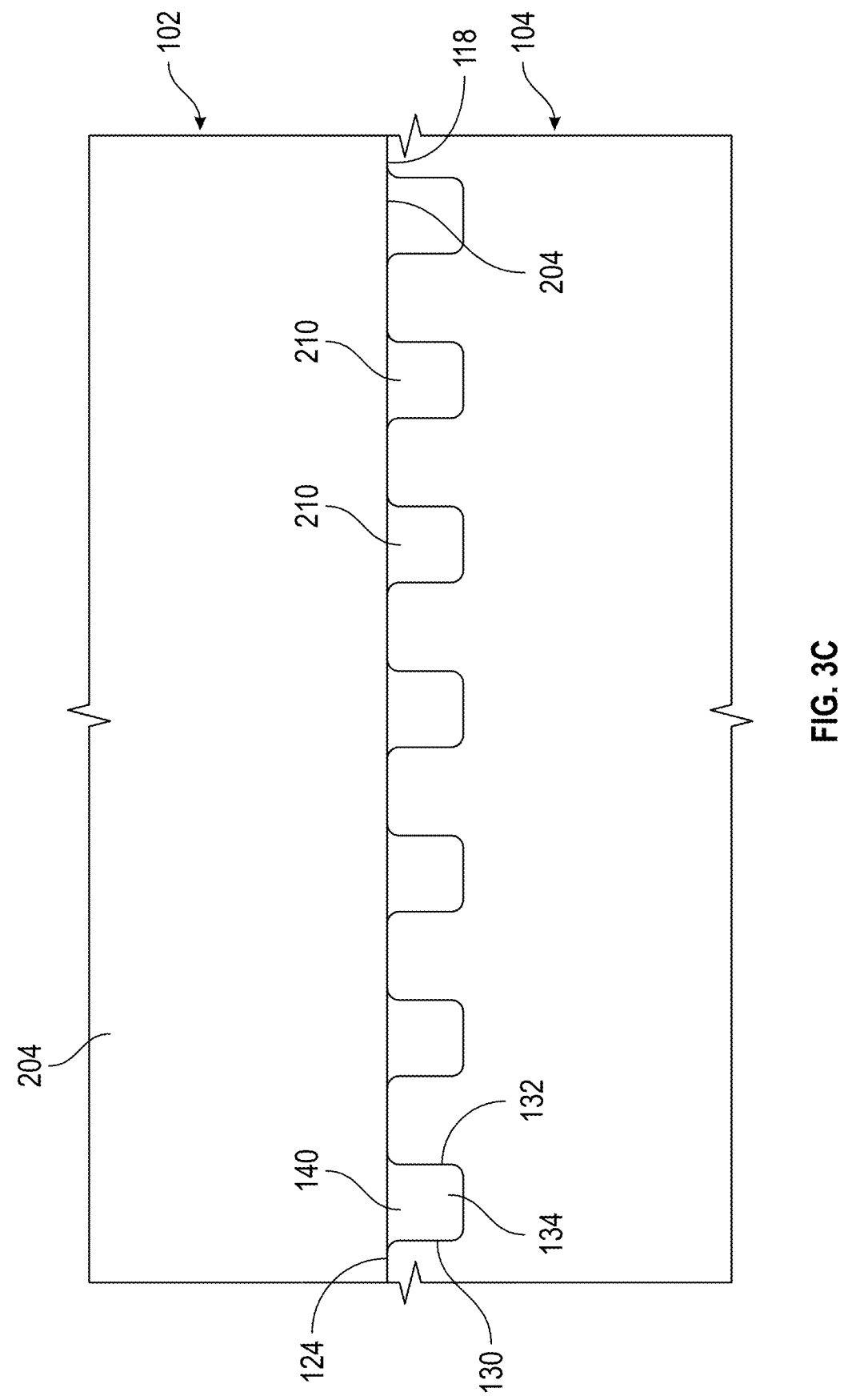
Figure 4A:
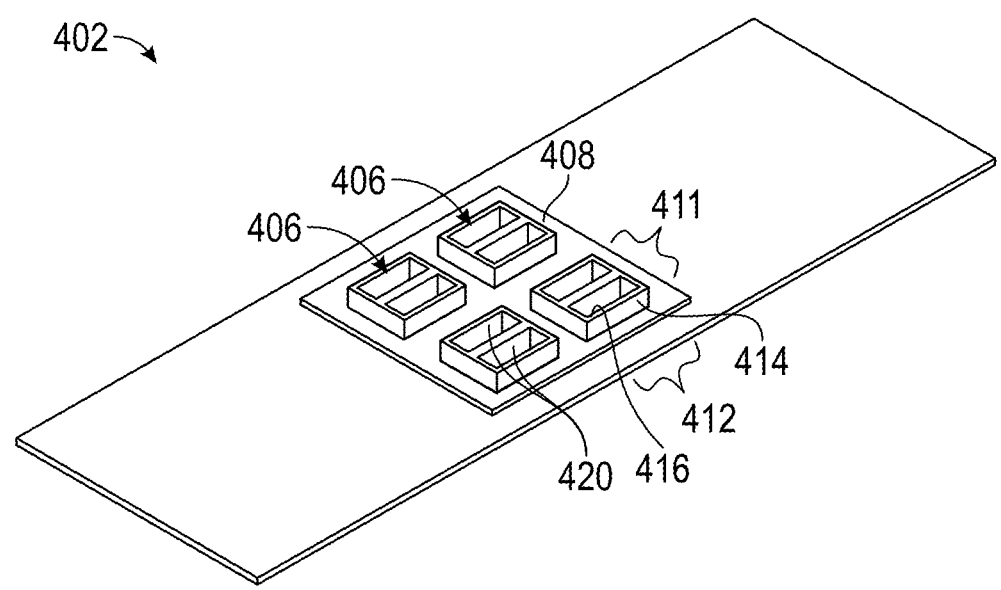
Figure 4B:
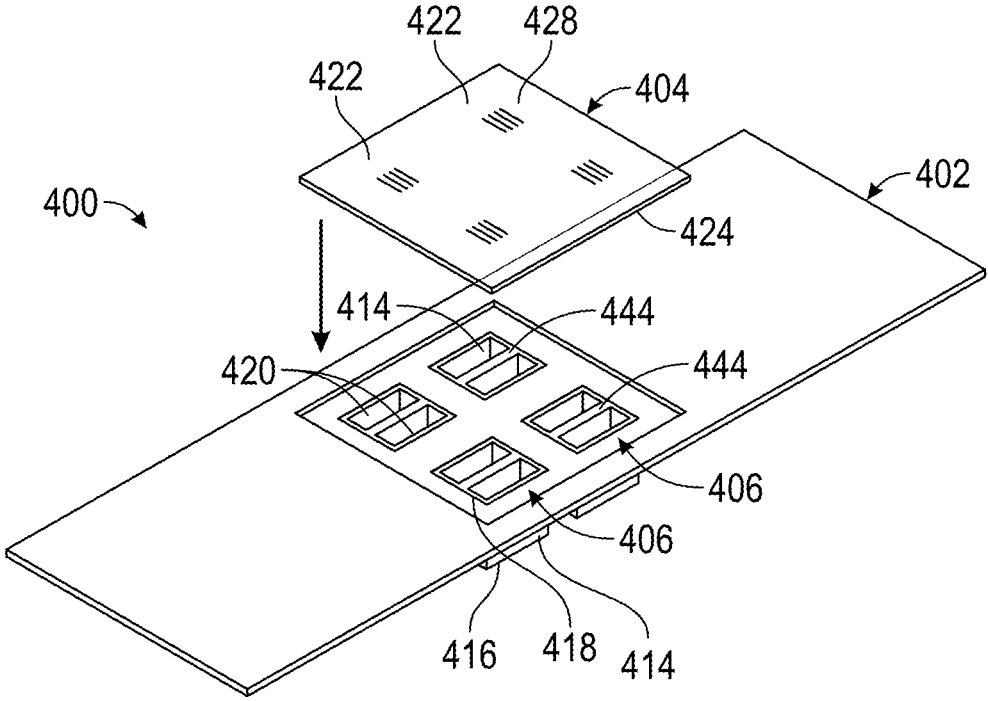
Figure 5:
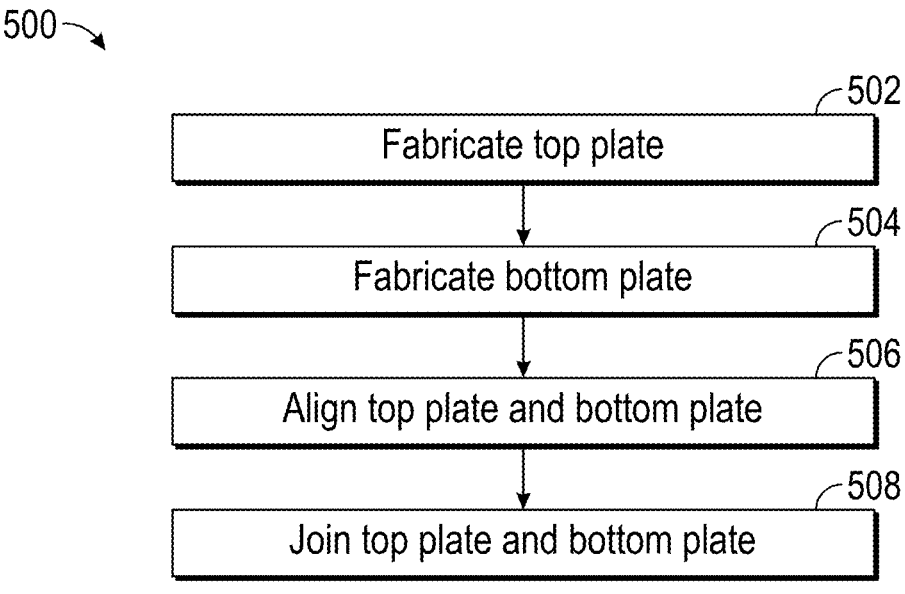
Figure 6A:
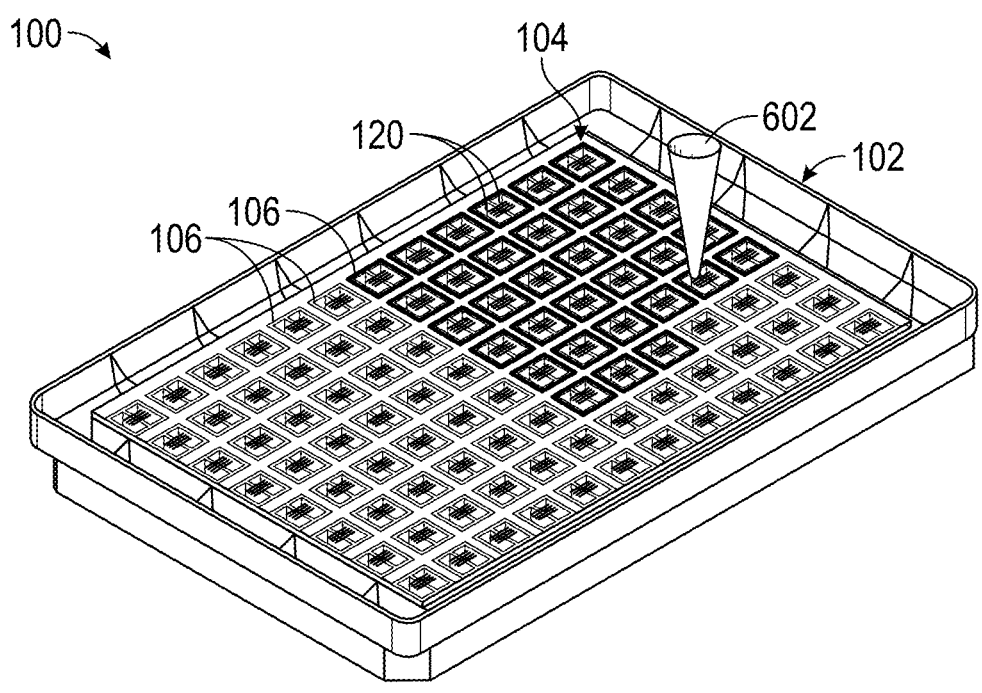
Figure 6B:
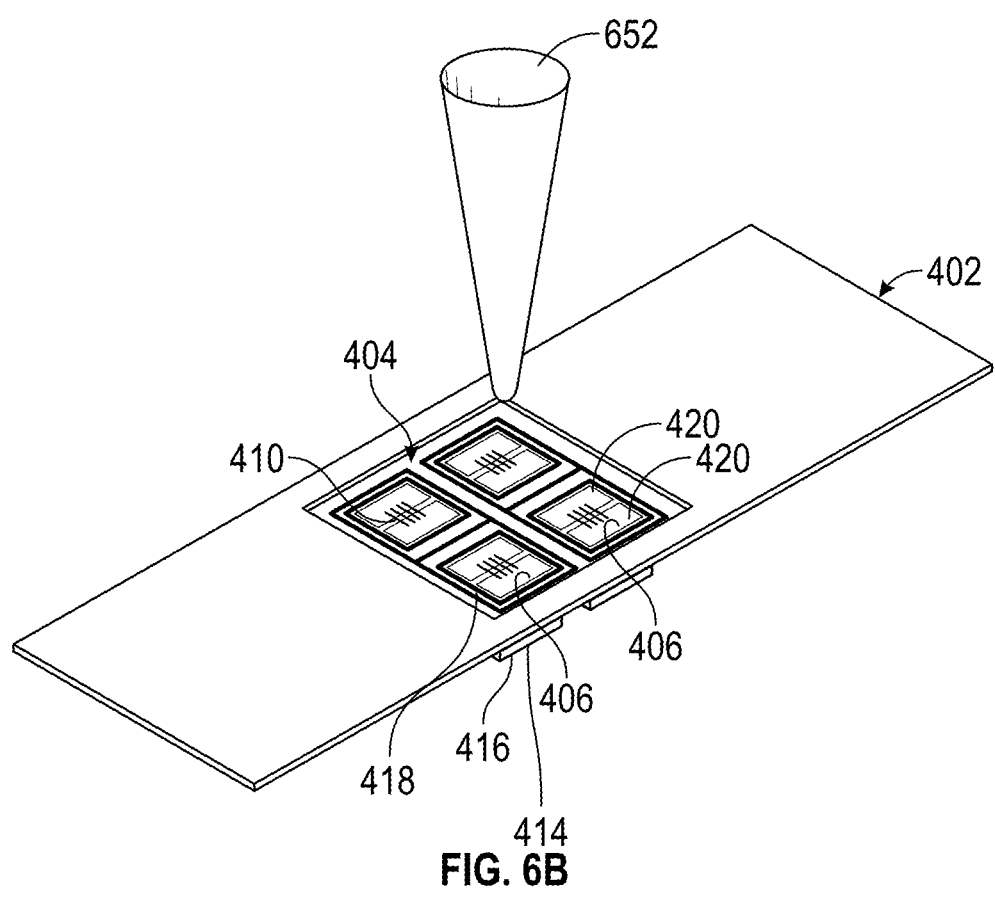
Figure 7A:
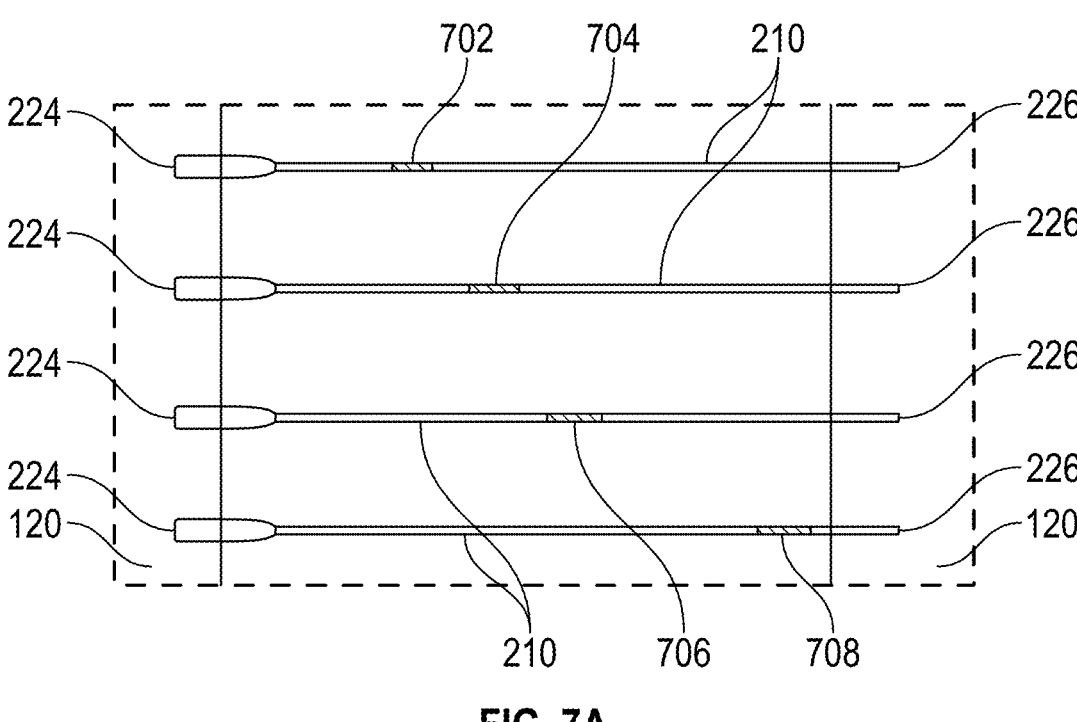
Figure 7B:
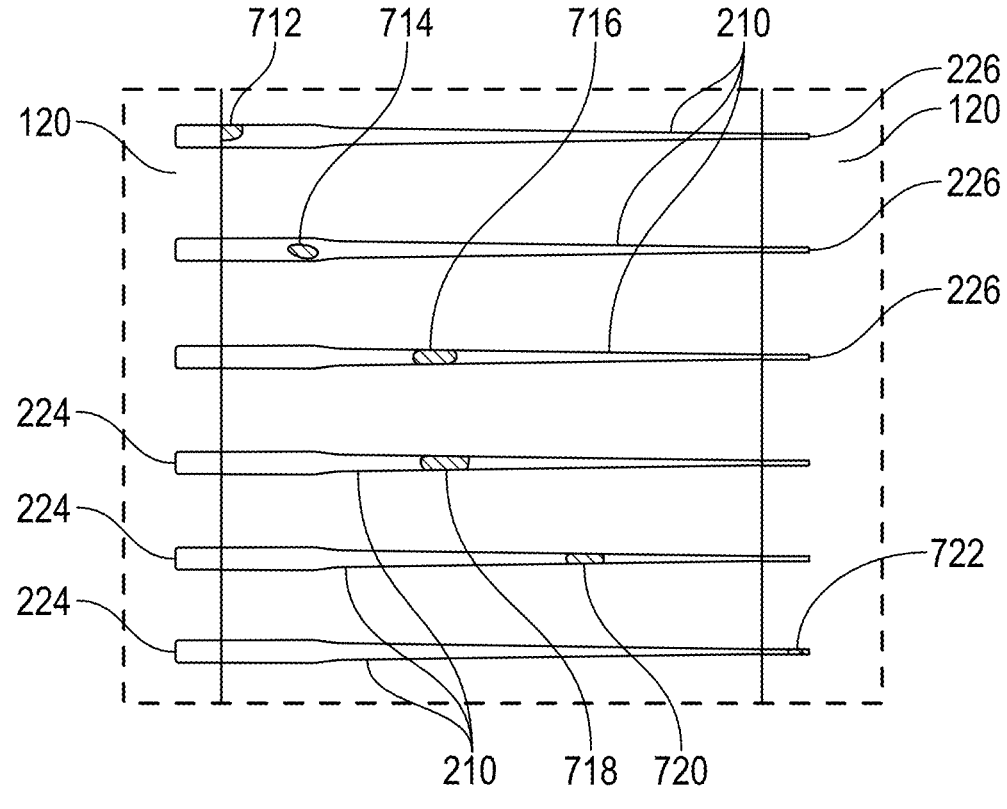
Figures 8A, 8B, 8C, 8D:
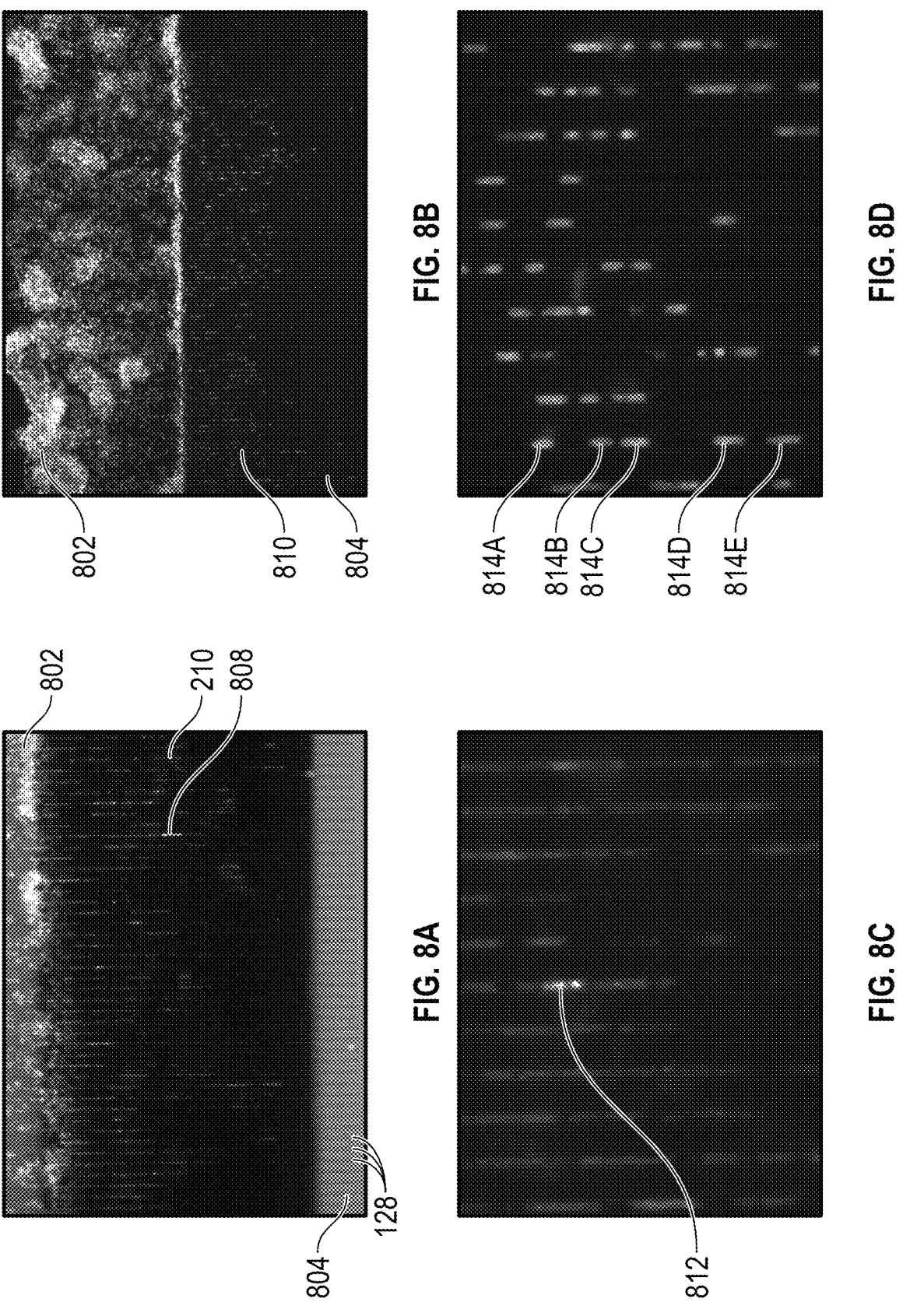
Figure 9A:
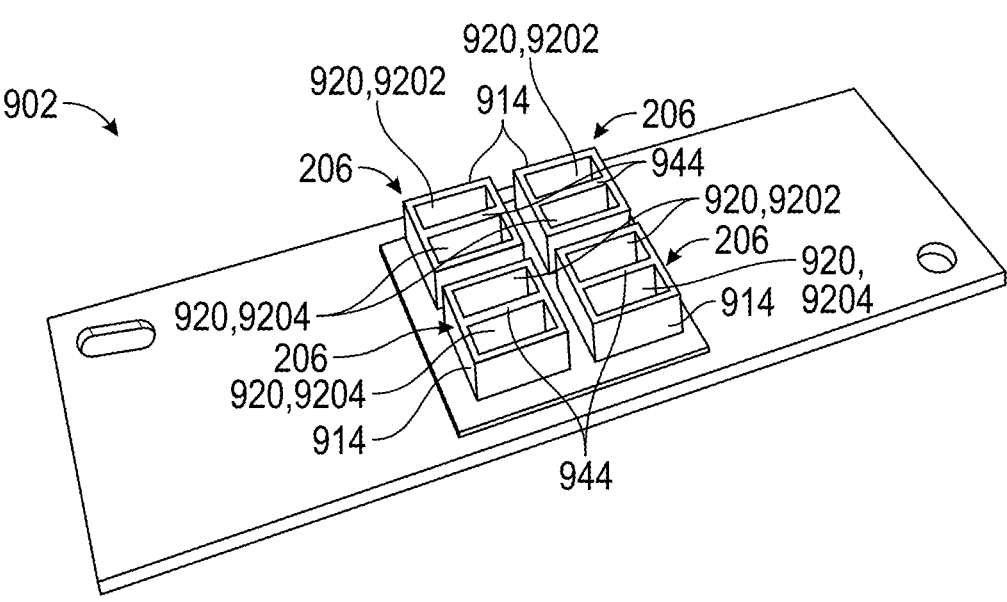
Figure 9B:
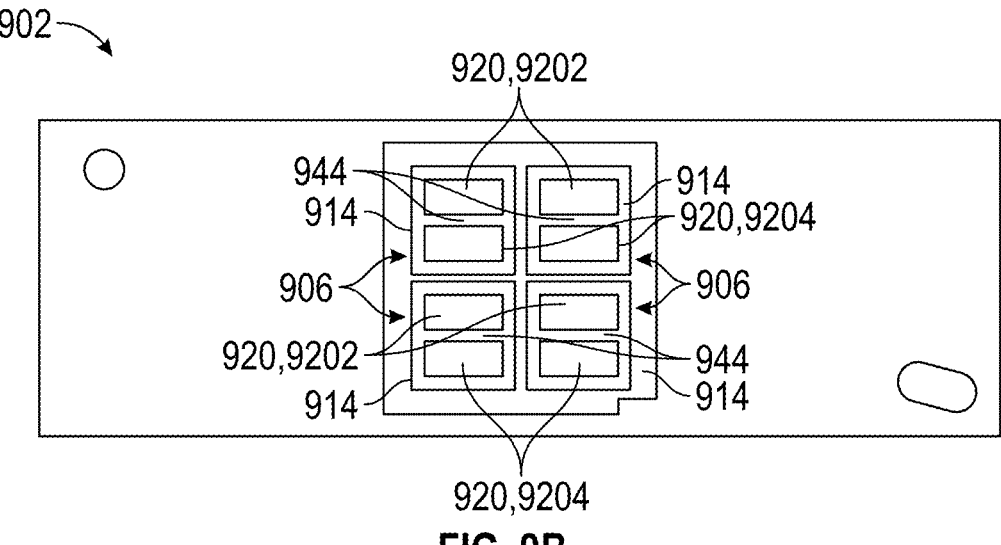
Figure 9C:
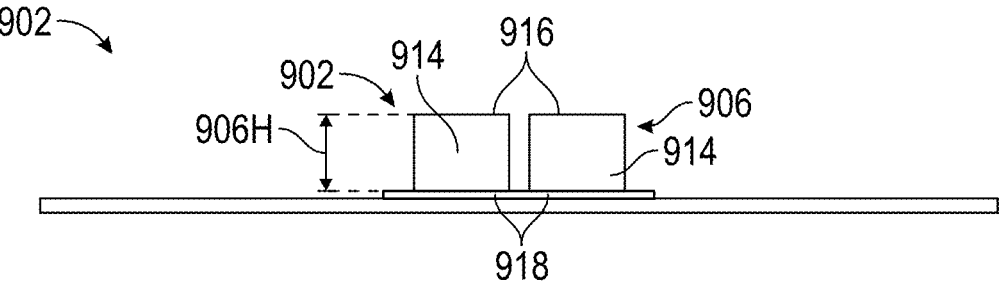
Figure 9D:
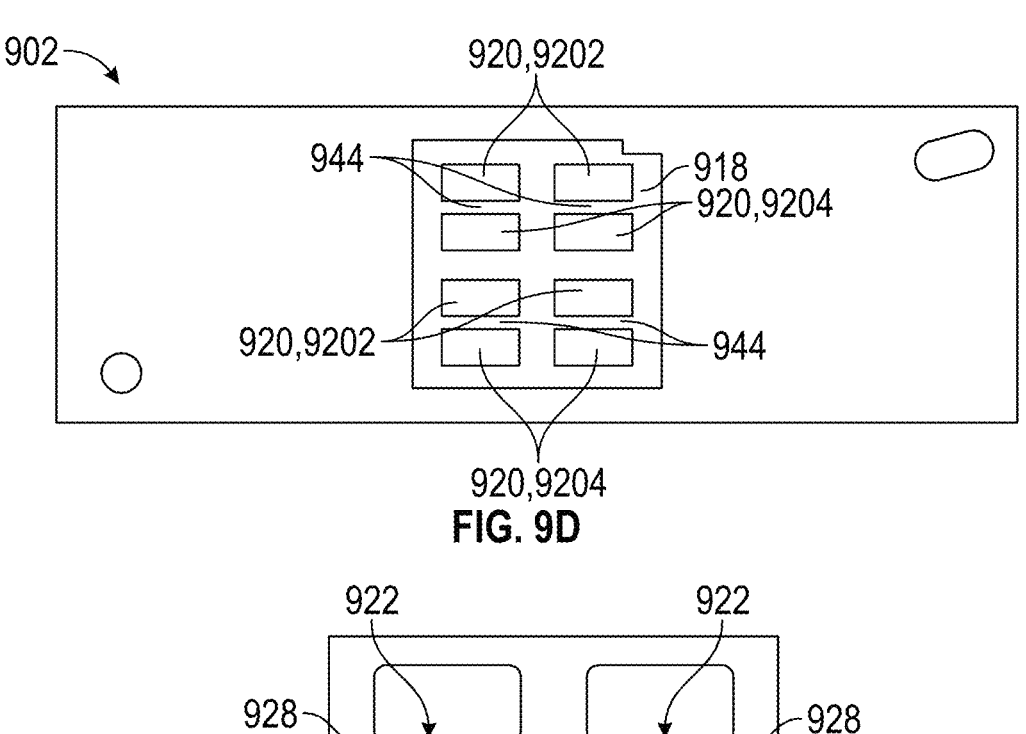
Figure 10A:
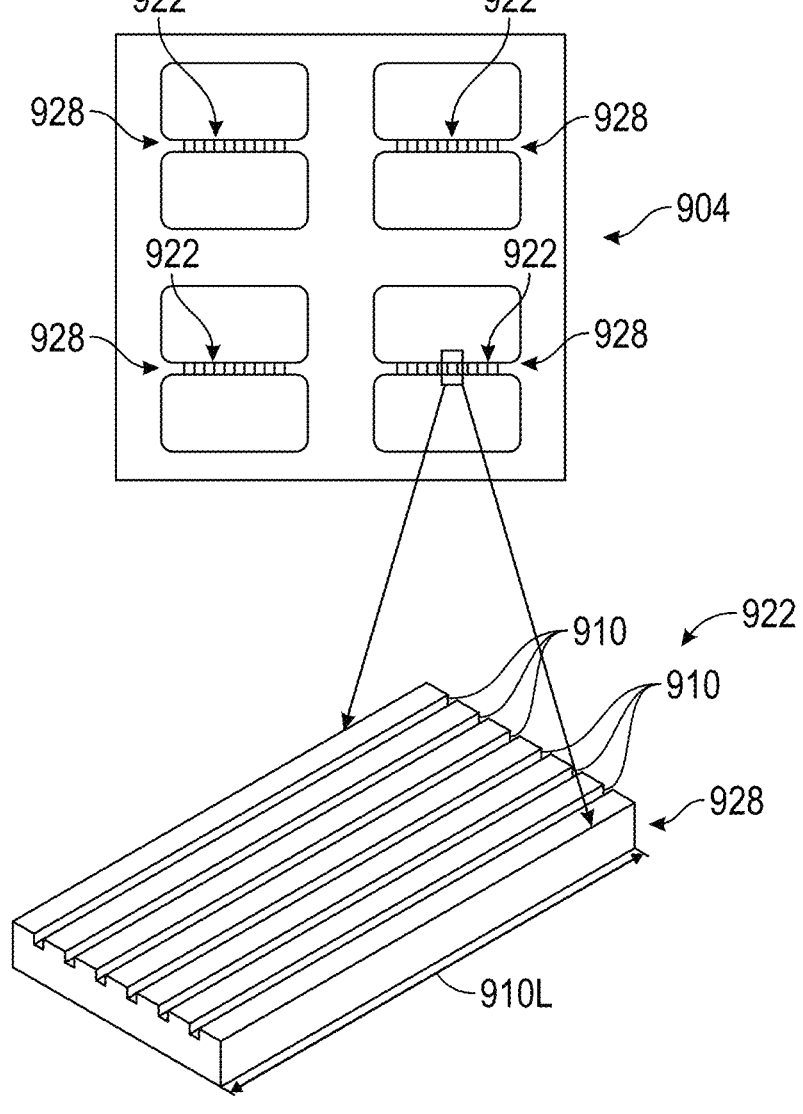
Figure 11:
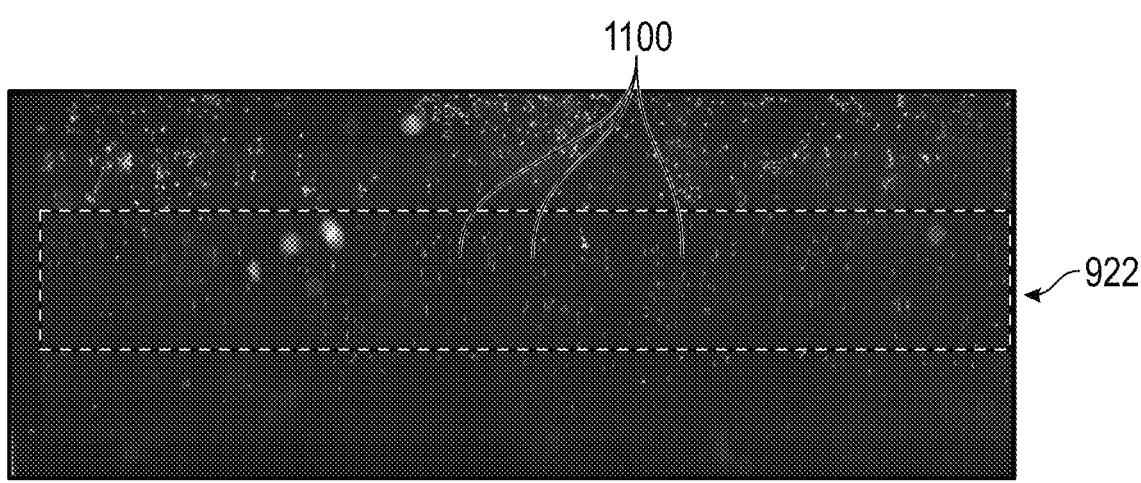
Figure 12A:
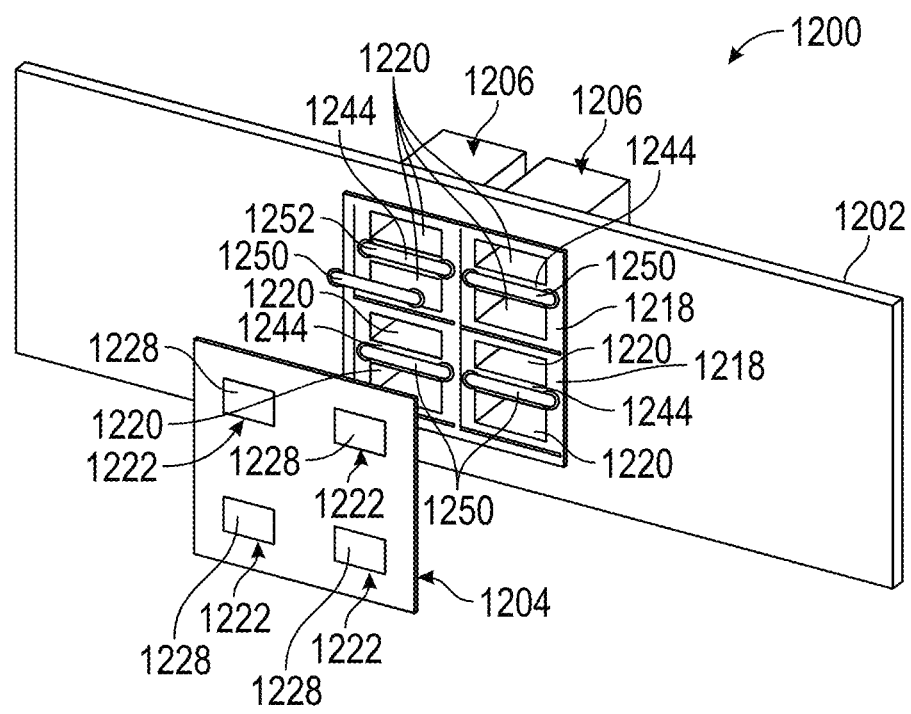
Figure 12B:
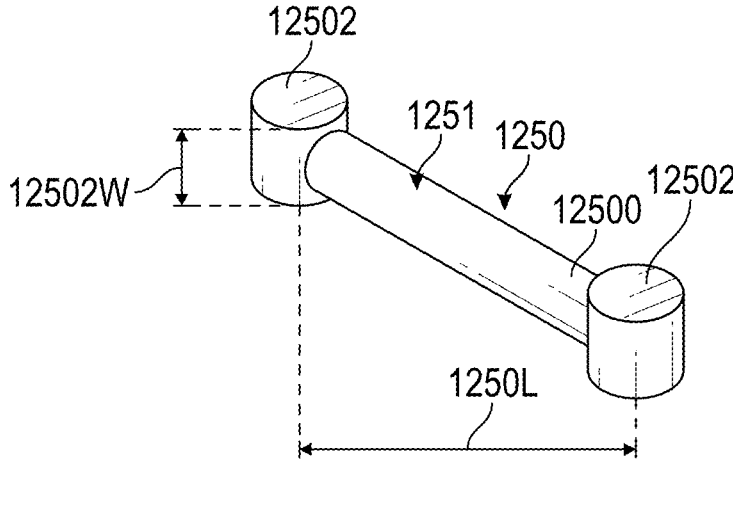
Figure 12C:
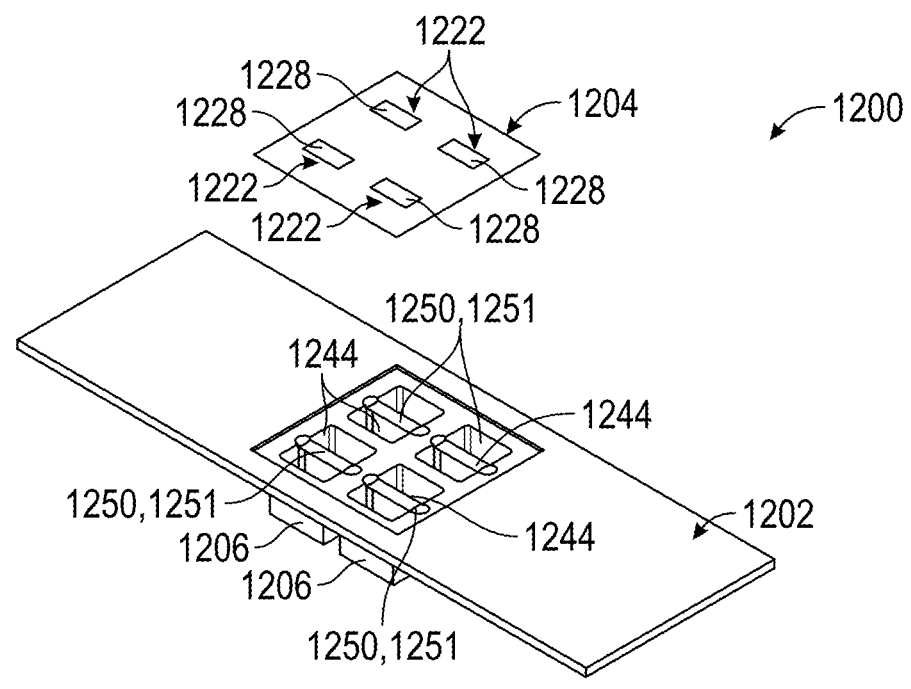
Figure 12D:
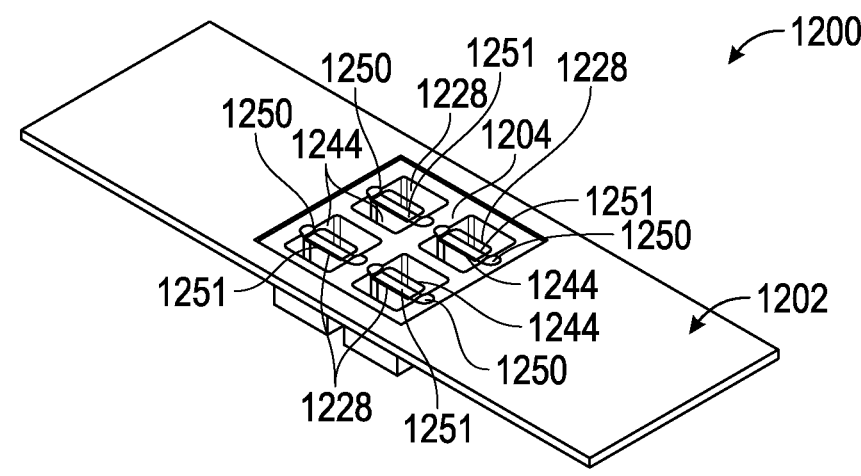
Figure 12E:
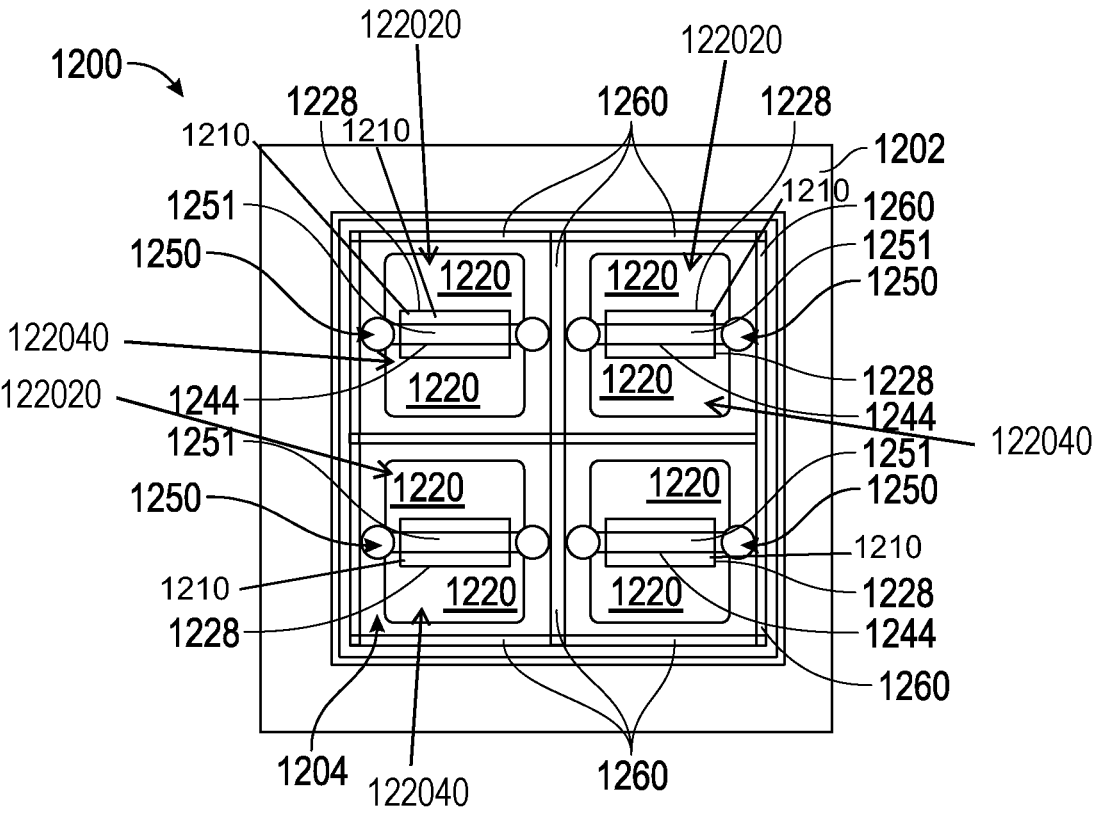
Figures 13, 14A:
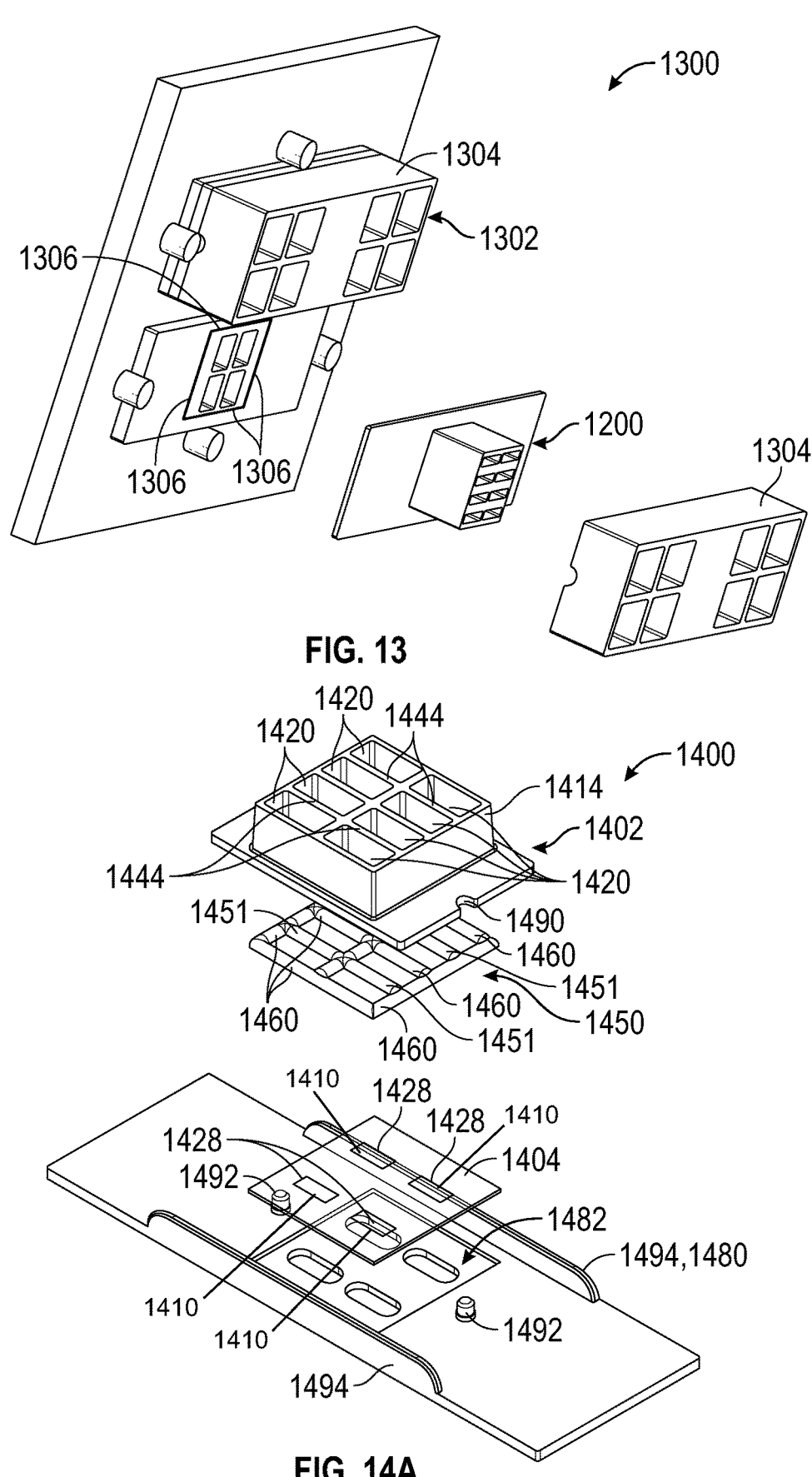
Figure 14B:
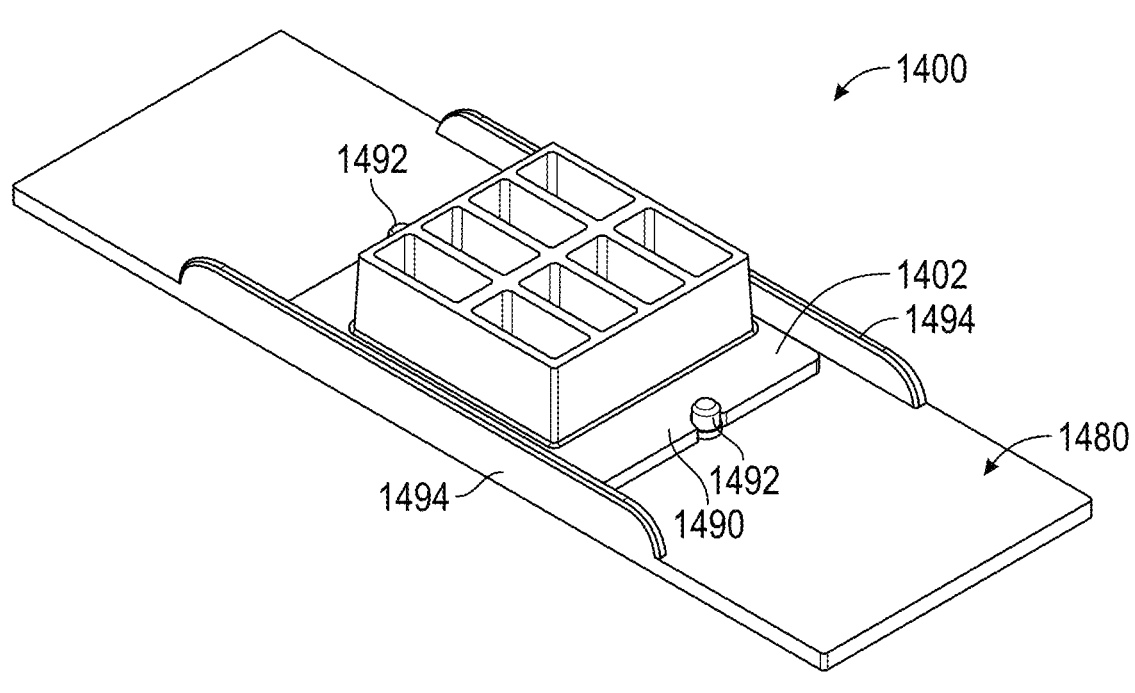
Figure 14C:
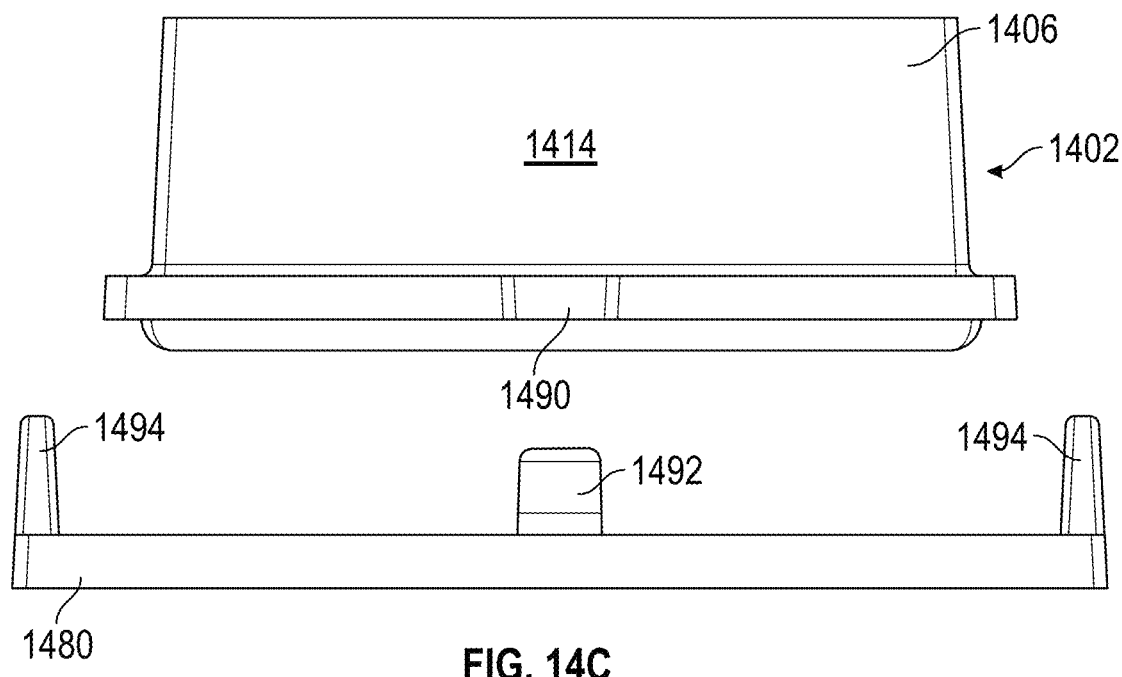
Figure 15A:
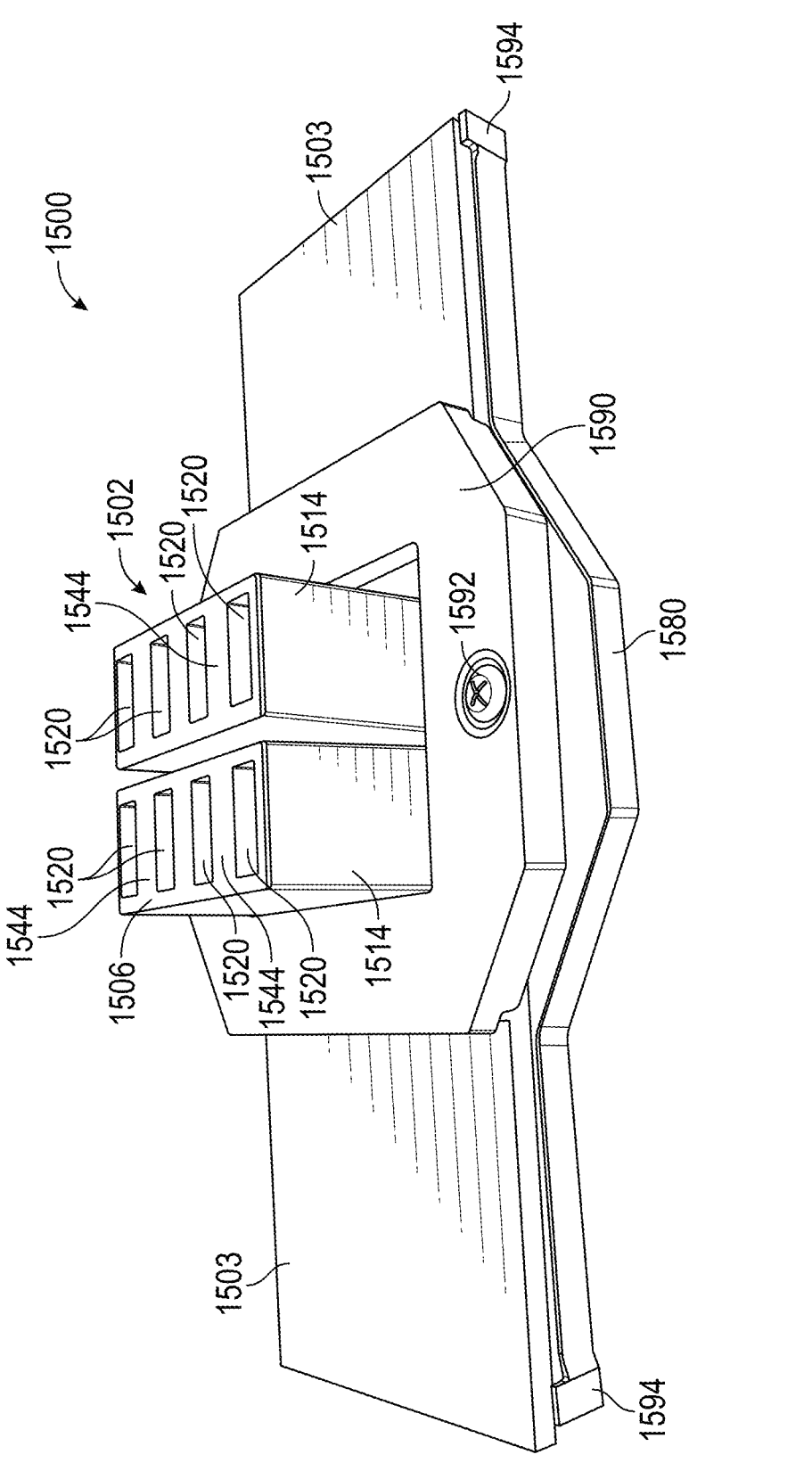
Figure 15B:
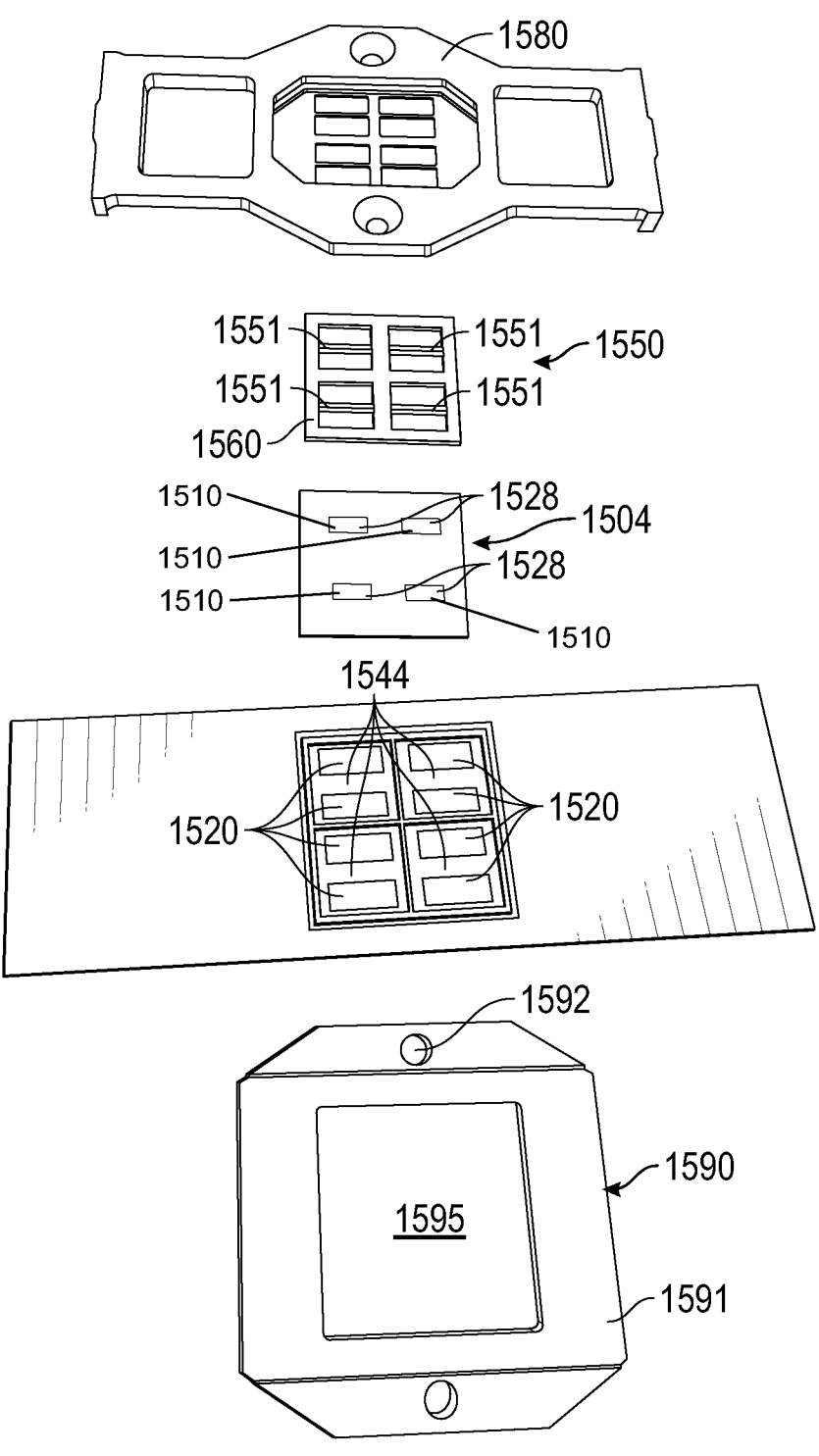

FIG. 3B is a magnified view of FIG. 3A, with hidden portions illustrated, in accordance with embodiments of the present inventive concept;

FIG. 3C is an elevated side, cross-sectional view of the CMAP assembly showing micro-channels formed, upon assembly of the large format CMAP assembly, in accordance with embodiments of the present inventive concept;

FIG. 4A is a top perspective view of a top plate of a small format CMAP assembly showing four (4) wells with eight (8) reservoirs extending through the top plate, prior to assembly of the small format CMAP assembly, in accor-dance with embodiments of the present inventive concept;

FIG. 4B is a bottom perspective view of the top plate of FIG. 4A and a bottom plate showing four (4) sets of troughs, prior to assembly of the small format CMAP assembly, in accordance with embodiments of the present inventive con-cept;

FIG. 5 is a flow chart illustrating steps to form the large format CMAP assembly or the small format CMAP assem-bly, in accordance with embodiments of the present inven-tive concept;

FIG. 6A is a bottom perspective view of the large format CMAP assembly with the top plate and the bottom plate of FIGS. 1A-1D being joined together via a welding process, in accordance with embodiments of the present inventive con-cept;

FIG. 6B is a bottom perspective view of the small format CMAP assembly with the top plate and the bottom plate of FIGS. 4A-4B being joined together via a welding process, in accordance with embodiments of the present inventive con-cept;

FIG. 7A is a magnified section view of FIG. 2B showing cells migrating through the straight micro-channels, in accordance with embodiments of the present inventive con-cept;

FIG. 7B is a magnified section view of FIG. 2B showing cells migrating through the tapered micro-channels, in accordance with embodiments of the present inventive con-cept;

FIG. 8A is a merged Differential Interference Contrast (DIC) and fluoresence image of an input reservoir and an output reservoir and cells migrating through micro-channels of the CMAP assembly, in accordance with embodiments of the present inventive concept;

FIG. 8B is a fluorescence image showing cell migration in the micro-channels, in accordance with embodiments of the present inventive concept;

FIG. 8C is a magnified fluorescence image showing cell body migration in the micro-channels, in accordance with embodiments of the present inventive concept;

FIG. 8D is a magnified fluorescence image showing cell nucleus of same cells in FIG. 8C in the micro-channels, in accordance with embodiments of the present inventive con-cept;

FIG. 9A is a top perspective view of a top plate, in accordance with embodiments of the present inventive con-cept;

FIG. 9B is a top view of the top plate of FIG. 9A, in accordance with embodiments of the present inventive con-cept;

FIG. 9C is a side view of the top plate of FIG. 9A, in accordance with embodiments of the present inventive con-cept;

FIG. 9D is a bottom view of the top plate of FIG. 9A, in accordance with embodiments of the present inventive con-cept;

FIG. 10A is a top view of a trough component and an enlarged view of a plurality of troughs, in accordance with embodiments of the present inventive concept;

FIG. 10B is a top perspective view of the trough component, in accordance with embodiments of the present inventive concept;

FIG. 10C is a cross-sectional side view of a portion of the plurality of troughs of the trough component, in accordance with embodiments of the present inventive concept;

FIG. 10D is a cross-sectional side view of the trough component positioned proximate a bottom end of the top plate, in accordance with embodiments of the present inventive concept;

FIG. 11 is a magnified fluorescence image showing cell migration in the troughs and micro-channels, in accordance with embodiments of the present inventive concept;

FIG. 12A is a bottom, partially exploded perspective view of a CMAP assembly, in accordance with embodiments of the present inventive concept;

FIG. 12B is a perspective view of a trough gasket, in accordance with embodiments of the present inventive concept;

FIG. 12C is a bottom, partially exploded perspective view of the CMAP assembly of FIG. 12A, in accordance with embodiments of the present inventive concept;

FIG. 12D is a bottom perspective view of the CMAP assembly of FIG. 12A, in accordance with embodiments of the present inventive concept;

FIG. 12E is a bottom view of a portion of the CMAP assembly of FIG. 12A with a sealing component including laser welding, in accordance with embodiments of the present inventive concept;

FIG. 13 is a partially exploded, perspective view of a cutting tool operable to cut the trough component of each well from the CMAP assembly, in accordance with embodiments of the present inventive concept;

FIG. 14A is a top perspective, partially exploded view of a CMAP assembly with a grid gasket and an alignment plate, in accordance with embodiments of the present inventive concept;

FIG. 14B is a top perspective view of the CMAP assembly of FIG. 14A in an assembled configuration, in accordance with embodiments of the present inventive concept;

FIG. 14C is a side view of the CMAP assembly of FIG. 14A, in accordance with embodiments of the present inventive concept;

FIG. 15A is a top perspective view of a CMAP assembly with a clamp component, in accordance with embodiments of the present inventive concept; and FIG. 15B is a bottom perspective, exploded view of the CMAP assembly of FIG. 15A.

The drawing figures do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The following detailed description references the accompanying drawings that illustrate various embodiments of the present inventive concept. The illustrations and description are intended to describe aspects and embodiments of the present inventive concept in sufficient detail to enable those skilled in the art to practice the present inventive concept. Other components can be utilized, and changes can be made without departing from the scope of the present inventive concept. The following description is, therefore, not to be taken in a limiting sense. The scope of the present inventive concept is defined only by the appended claims, along with the full scope of equivalents to which such claims are entitled.

I. Terminology

The phraseology and terminology employed herein are for the purpose of description and should not be regarded as limiting. For example, the use of a singular term, such as, "a" is not intended as limiting of the number of items. Also, the use of relational terms such as, but not limited to, "top," "bottom," "left," "right," "upper," "lower," "down," "up," and "side," are used in the description for clarity in specific reference to the figures and are not intended to limit the scope of the present inventive concept or the appended claims.

Further, as the present inventive concept is susceptible to embodiments of many different forms, it is intended that the present disclosure be considered as an example of the principles of the present inventive concept and not intended to limit the present inventive concept to the specific embodiments shown and described. Any one of the features of the present inventive concept may be used separately or in combination with any other feature. References to the terms "embodiment," "embodiments," and/or the like in the description mean that the feature and/or features being referred to are included in, at least, one aspect of the description. Separate references to the terms "embodiment," "embodiments," and/or the like in the description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments but is not necessarily included. Thus, the present inventive concept may include a variety of combinations and/or integrations of the embodiments described herein. Additionally, all aspects of the present disclosure, as described herein, are not essential for its practice. Likewise, other systems, methods, features, and advantages of the present inventive concept will be, or become, apparent to one with skill in the art upon examination of the figures and the description. It is intended that all such additional systems, methods, features, and advantages be included within this description, be within the scope of the present inventive concept, and be encompassed by the claims.

Any term of degree such as, but not limited to, "substantially" as used in the description and the appended claims, should be understood to include an exact, or a similar, but not exact configuration. For example, "a substantially planar surface" means having an exact planar surface or a similar, but not exact planar surface. Similarly, the terms "about" or "approximately," as used in the description and the appended claims, should be understood to include the recited values or a value that is three times greater or one third of the recited values. For example, about 3 mm includes all values from 1 mm to 9 mm, and approximately 50 degrees includes all values from 16.6 degrees to 150 degrees. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The terms "comprising," "including" and "having" are used interchangeably in this disclosure. The terms "comprising," "including" and "having" mean to include, but not necessarily be limited to the things so described.

Lastly, the terms "or" and "and/or," as used herein, are to be interpreted as inclusive or meaning any one or any combination. Therefore, "A, B or C" or "A, B and/or C" mean any of the following: "A," "B" or "C"; "A and B"; "A and C"; "B and C"; "A, B and C." An exception to this definition will occur only when a combination of elements, functions, steps or acts are in some way inherently mutually exclusive.

II. General Architecture

Turning to FIGS. 1A-1D, a large format Cell Migration Assay Plates (CMAP) assembly 100 is illustrated according to an embodiment of the present inventive concept. The CMAP assembly 100 is generally defined by a top plate 102 and a bottom plate 104.

The top plate 102 includes ninety-six (96) wells 106 extending entirely through the top plate 102. The wells 106 are arranged in an array 108, with eight (8) rows 110 and twelve (12) columns 112. The top plate 102 may also optionally include chamfered corners on one side of the top plate 102. The chamfered corners can serve as alignment markers to facilitate assembly of a cover of a similar shape, e.g., with corresponding chamfered corners, onto the top plate 102 to close one side of the wells 106.

Each of the wells 106 is defined by a perimeter sidewall 114 with a top peripheral edge 116 spaced from a bottom peripheral edge 118 of the perimeter sidewall 114. The perimeter sidewall 114 defines a set of reservoirs 120, e.g., a first reservoir and a second reservoir extending entirely through the top plate 102, thereby causing each of the wells 106 to be substantially bottomless.

The bottom plate 104 includes ninety-six (96) trough sets 122 formed into a substantially planar surface 124 on one side 126 of the bottom plate 104. Each set of the troughs sets 122 includes a linear array of troughs 128 that corresponds to one of the wells 106. Each trough of the linear array of troughs 128 is defined by opposing sidewalls 130, 132, a bottom wall 134 extending between the sidewalls 130, 132, and opposing end walls 136, 138 extending between the sidewalls 130, 132. The opposing sidewalls 130, 132, the bottom wall 134, and the end walls 136, 138 collectively define an elongated cavity 140 for receiving one or more cells or drugs.

It is foreseen that the linear array of troughs 128 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 128 includes two-hundred and forty (240) troughs, with a cross-section of 5 μm×5 μm, and a length of 700 μm.

Figure 1A:
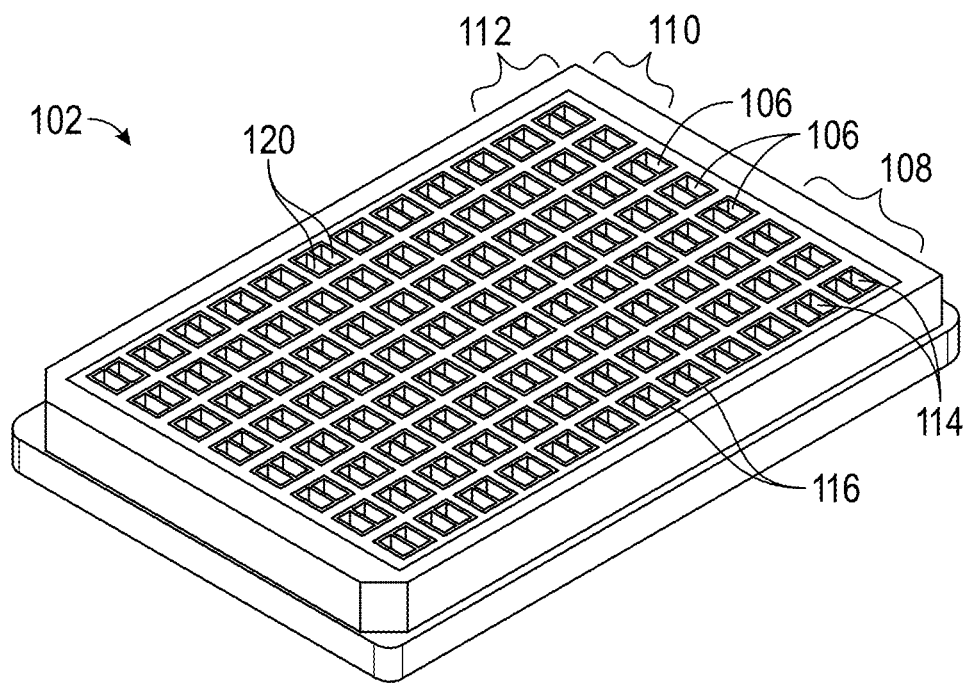
FIG. 1A is a top perspective view of a top plate of a large format Cell Migration Assay Plates (CMAP) assembly showing ninety-six (96) wells extending through the top plate, prior to assembly of the large format CMAP assembly, in accordance with embodiments of the present inventive concept.
Figure 1B:
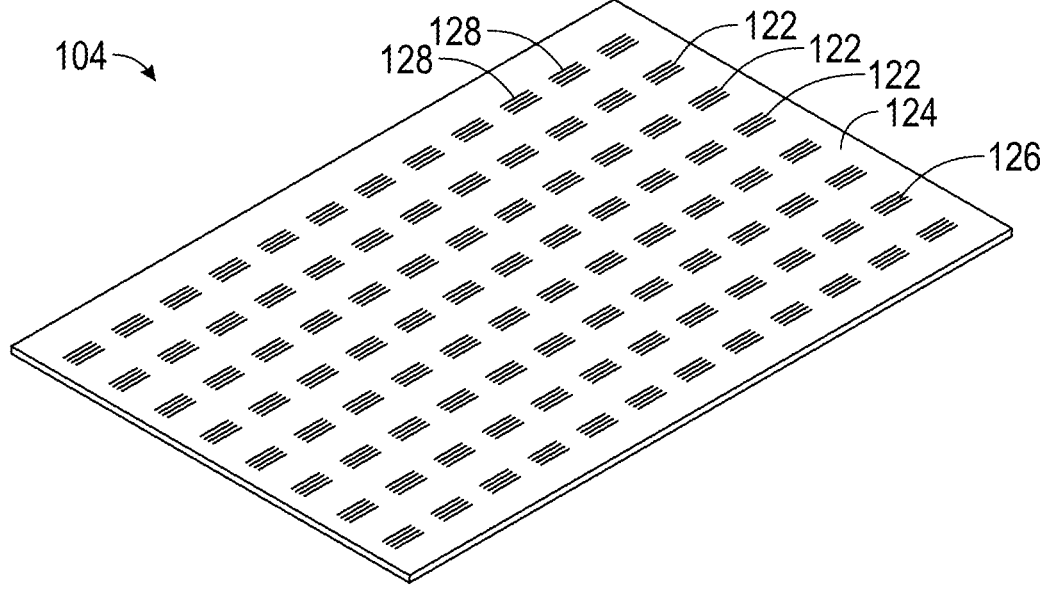
FIG. 1B is a top perspective view of a bottom plate of the large format CMAP assembly showing ninety-six (96) sets of troughs imprinted into the bottom plate, prior to assembly of the large format CMAP assembly, in accordance with embodiments of the present inventive concept.
Figure 1C:
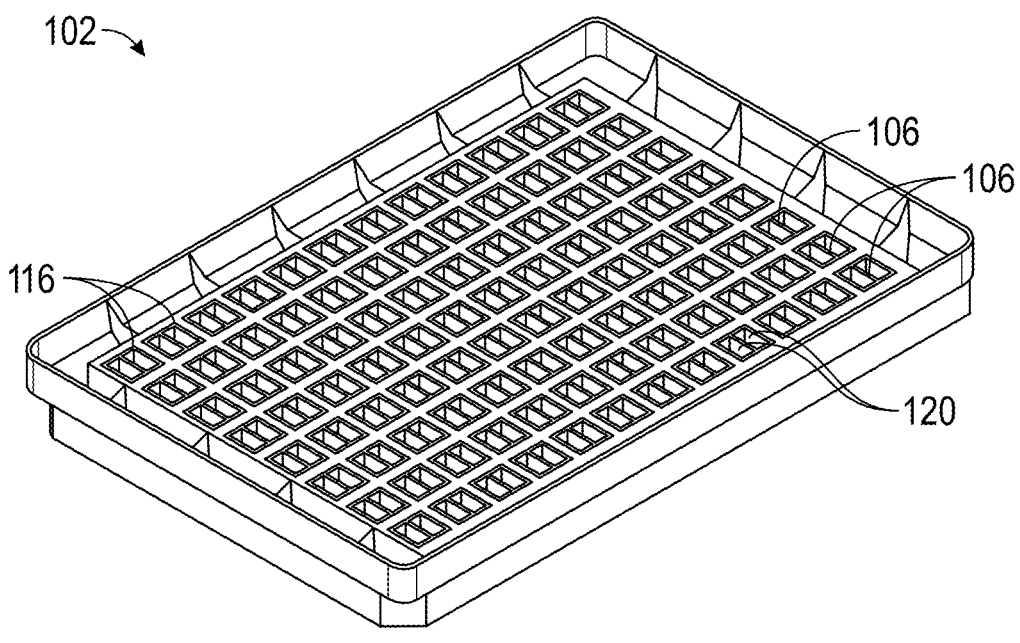
FIG. 1C is a bottom perspective view of the top plate of FIG. 1A, in accordance with embodiments of the present inventive concept.
Figure 1D:
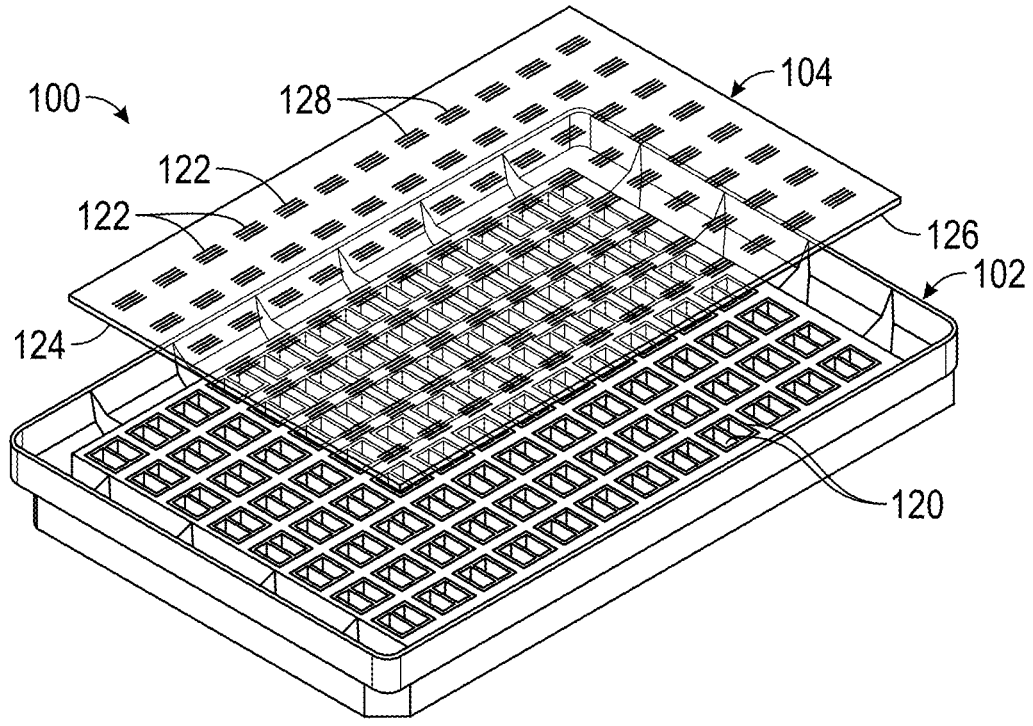
FIG. 1D is a bottom perspective view of the top plate and the bottom plate of FIGS. 1A-1C prior to assembly of the large format CMAP assembly, in accordance with embodi-ments of the present inventive concept.

As illustrated, FIGS. 1A and 10 respectively show bottom and top perspective views of the top plate 102 of the large format CMAP assembly 100 prior to assembly to the bottom plate 104, which is illustrated via FIG. 1B. FIG. 1D is a top perspective view of the top plate 102 aligned with the bottom plate 104 prior to securing the top plate 102 to the bottom plate 10 to form the large format CMAP assembly 100.

Turning to FIG. 2A, a magnified top plan view of one of the wells 106 with the set of reservoirs 120 of the top plate 102 is illustrated, prior to assembly of the large format CMAP assembly 100. Each of the reservoirs 120 includes the perimeter sidewall 114 with the top peripheral edge 116 spaced from the bottom peripheral edge 118 of the perimeter sidewall 114. A separation or divisional wall portion 204 extends between the reservoirs 120. In an embodiment, the divisional wall portion 204 separates the reservoirs 120 with a thickness of 500 μm. It is foreseen that the thickness of the divisional wall portion 204 may be greater or smaller without deviating from the scope of the present inventive concept.

Turning to FIG. 2B-3C, one of the wells 106 with the set of reservoirs 120 of the top plate 102 and one of the linear arrays of troughs 128 of the bottom plate 104 are illustrated, after assembly of the large format CMAP assembly 100. When the top plate 102 and the bottom plate 104 are assembled to form the large format CMAP assembly 100, the planar surface 124 of the bottom plate 104 abuts the bottom peripheral edge 118 of the perimeter sidewall 114 such that each reservoir of the set of reservoirs 120 and each of the wells 106 are sealed by the bottom plate 104 and micro-channels 210 are formed, which fluidly connect each reservoir of the set of reservoirs 120.

Each of the micro-channels 210 includes an entrance opening 212 and an exit opening 214 at opposite ends thereof to define a one-way direction of fluid communication between each reservoir of the set of reservoirs 120. Each of the micro-channels 210 is defined by a middle portion 220 of each trough of the linear array of troughs 128 and a surface of the divisional wall portion 204, which functions as a micro-channel roof. On one side of the middle portion 220, an entry portion 224 of each trough of the linear array of troughs 128 does not have the micro-channel roof and, therefore, remains open into a first one of the reservoirs 120, which is operable to function as a seeding or input reservoir. In this manner, the input reservoir can be used to temporarily contain a cell and guide the cell into a respective one of the micro-channels 210. On another side of the middle portion 220, an exit portion 226 of each trough of the linear array of troughs 128 also does not have the micro-channel roof and, therefore, also remains open into a second one of the reservoirs 120, which is operable to function as an output reservoir. In this manner, the output reservoir can be used to receive the tumor cells after migration through one of the plurality of micro-channels. The entry portion 224 and the exit portion 226 advantageously provide an extra margin in case of misalignment between the linear array of troughs 128 and the divisional wall portion 204 during assembly of the top plate 102 and the bottom plate 104. In an embodiment, when properly aligned, each trough of the linear array of troughs 128 has a length of approximately 700 μm, and the entry portion 224 and the exit portion 226 respectively protrude approximately 100 μm past either side of the divisional wall 204, which has a thickness of approximately 500 μm. In an embodiment, the micro-channels 210 have varying lengths and/or cross-sections. For instance, it is foreseen that a width of the divisional wall 204 may be increased or decreased to respectively increase or decrease a length and/or cross-section of the micro-channels 210. In this manner, the top plate 102, and the bottom plate 104 are advantageously operable to function as microfluidic device plates that enable a user to interrogate migratory potential of cells such as tumor cells.

In an embodiment, the large format CMAP assembly 100 includes 240×96 or 23,040 of the micro-channels 210. In an embodiment, the micro-channels 308 may have a square cross-section, e.g., 5 μm×5 μm, or a rectangular cross-section, e.g., 5 μm by 3 μm. It is foreseen that the number of micro-channels 210 may be of greater number or smaller number and/or of greater size or of smaller size, without deviating from the scope of the present inventive concept. In this manner, given the high number of micro-channels 210, the CMAP assembly 100 is advantageously operable to provide a high throughput relative to a basic microfluidic migration device.

As illustrated, FIG. 3A shows a perspective view of the CMAP assembly 100 with the micro-channels 210 formed, FIG. 3B shows a magnified view of FIG. 3A, except with portions hidden by the divisional wall portion 204 illustrated, and FIG. 3C shows a side view of the micro-channels 210 formed via the top plate 102 and the bottom plate 104.

Turning to FIGS. 4A-B, a small format Cell Migration Assay Plates (CMAP) assembly 400 is illustrated according to an embodiment of the present inventive concept. The CMAP assembly 400 is generally defined by a top plate 402 and a bottom plate 404.

The top plate 202 includes four (4) wells 406 extending entirely through the top plate 202. The wells 406 are arranged in an array 408 with two (2) rows 411 and two (2) columns 412. Each of the wells 406 is defined by a perimeter sidewall 414 with a top peripheral edge 416 spaced from a bottom peripheral edge 418 of the perimeter sidewall 414. The perimeter sidewall 414 defines a set of reservoirs 420, e.g., a first reservoir and a second reservoir, extending entirely through the top plate 202, thereby causing each of the wells 406 to be substantially bottomless.

The bottom plate 404 includes four (4) trough sets 422 formed into a planar surface 424 on one side 426 of the bottom plate 404. Each set of the troughs sets 422 includes a linear array of troughs 428 that correspond to a respective one of the wells 406. Similar to each trough of the linear array of troughs 128, each trough of the linear array of troughs 428 is defined by opposing sidewalls, a bottom wall extending between the sidewalls, and opposing end walls extending between the sidewalls. The opposing sidewalls, the bottom wall, and the end walls collectively define an elongated cavity for receiving one or more cells or drugs.

It is foreseen that the linear array of troughs 428 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 428 includes two-hundred and forty (240) troughs, with a cross-section of 5 μm×5 μm, and a length of 700 μm.

Each reservoir of the set of reservoirs 420 includes the perimeter sidewall 414 extending through the bottom plate 404. The top plate 402 includes a separation or divisional wall portion 444 extending between the set of reservoirs 420. In an embodiment, the divisional wall portion 444 separates the set of reservoirs 420 with a thickness of 500 μm. It is foreseen that the thickness of the divisional wall portion 444 may be greater or smaller without deviating from the scope of the present inventive concept.

When the top plate 402 and the bottom plate 404 are assembled to form the small format CMAP assembly 400, the planar surface 424 of the bottom plate 404 abuts the top plate 402 such that each reservoir of the set of reservoirs 420 and each of the wells 406 are sealed by the bottom plate 404 and micro-channels are formed, which fluidly connect each reservoir of the set of reservoirs 420.

Similar to the micro-channels 210, each of the micro-channels 410 include an entrance opening and an exit opening at opposite ends thereof to define a one-way direction of fluid communication between each reservoir of the set of reservoirs 420. Each of the micro-channels 410 are defined by a middle portion of each trough of the linear array of troughs 428 and a surface of the divisional wall portion 444, which functions as a micro-channel roof. On one side of the middle portion, an entry portion of each trough of the linear array of troughs 428 does not have the micro-channel roof and, therefore, remains open into a first one of the set of reservoirs 420, which is operable to function as a seeding or input reservoir. In this manner, the input reservoir can be used to temporarily contain a cell and guide the cell into a respective one of the micro-channels 410. On another side of the middle portion, an exit portion of each trough of the linear array of troughs 428 also does not have the micro-channel roof and, therefore, also remains open into a second one of the set of reservoirs 420, which is operable to function as an output reservoir. In this manner, the output reservoir can be used to receive the tumor cells after migration through one of the plurality of micro-channels. The entry portion and the exit portion advantageously provide an extra margin in case of misalignment between the linear array of troughs 428 and the divisional wall portion 444 during assembly of the top plate 402 and the bottom plate 404. In an embodiment, when properly aligned, each trough of the linear array of troughs 428 has a length of approximately 700 μm, and the entry portion and the exit portion respectively protrude approximately 100 μm past either side of the divisional wall portion 444, which has a thickness of approximately 500 μm. In an embodiment, the micro-channels 410 have varying lengths and/or cross-sections. For instance, it is foreseen that a width of the divisional wall portion 444 may be increased or decreased to respectively increase or decrease a length and/or cross-section of the micro-channels 410. In this manner, the top plate 402, and the bottom plate 404 are advantageously operable to function as microfluidic device plates that enable a user to interrogate migratory potential of cells such as tumor cells.

As illustrated, FIGS. 4A and 4B respectively show bottom and top perspective views of the top plate 402 of the small format CMAP assembly 400 prior to assembly to the bottom plate 404.

Micro-Channel Design

The CMAP assemblies 100, 400 can be designed with the micro-channels 210, 410 of various geometries, such as varying lengths, varying widths, and/or varying heights, which advantageously allow testing of and experimentations with various types of tumor cells and/or drugs.

The micro-channel dimensions (e.g., cross-section and length) can be selected for a single cell migration assay or a collective cell migration assay. When one of the micro-channels 210, 410 is wide and provides less physical confinement for cells, the one of the micro-channels 210, 410 provides two-dimensional (2D) migration for the cells and the cells do not touch fewer than all, e.g., one or two surfaces of the sidewalls 130, 132, the bottom wall 134, and the surface of the divisional wall portion 204, 444, which functions as the micro-channel roof. Conversely, when one of the micro-channels 210, 410 is narrow and provides greater physical confinement for cells, the cells are forced to squeeze through the one of the micro-channels 210, 410, for example, by touching all surfaces of the sidewalls 130, 132, the bottom wall 134, and the surface of the divisional wall portion 204, 444, which functions as the micro-channel roof. In this manner, greater physical confinement of the one of the micro-channels 210, 410 provides three-dimensional (3D) migration for cells.

The migration time of a cell in the micro-channels 210, 410 may vary between different ones of the micro-channels 210, 410 with different cross-section areas. For instance, if a same cell is caused to pass through a first one of the micro-channels 210, 410 and a second one of the micro-channels 210, 410, the cell may take more time to pass through the first one of the micro-channels 210, 410 than the second one of the micro-channels 210, 410 if the first one of the micro-channels 210, 410 has a smaller cross-section area than the second one of the micro-channels 210, 410. In some embodiments, tumor cells can migrate faster when their nucleus is totally confined (e.g., in the micro-channels 210, 410), which can happen up to a limit of physical confinement, beyond which the cell migration becomes slower. The cells can use a completely different mode of migration when physically confined which can confer faster migration speed.

In some embodiments, the micro-channels 210, 410 may have cross-section areas of a square shape, a rectangular shape, and/or a circular shape. Additionally, in some embodiments, the micro-channels 210, 410 may have a constant or consistent cross-section area. Additionally, in some embodiments, the micro-channels 210, 410 may have varying aspect ratios (e.g., a ratio of height to width) or varying heights and/or varying widths, for example, cross-section areas may vary along the length of a single one of the micro-channels 210, 410. For example, the single micro-channel may start with a width of 20 μm, then gradually contract to a width of 15 μm, a width of 10 μm, and a width of 5 μm. With such a varying cross-section area, the single micro-channel is advantageously operable to test cells in multiple one of the micro-channels 210, 410, e.g., four micro-channels, having widths of 20 μm, 15 μm, 10 μm, and 5 μm, respectively.

Additionally, in some embodiments, the cross-sections of the micro-channels 210, 410 may continuously decrease or at discrete steps, and/or may continuously increase or at discrete steps. Additionally, in some embodiments, the dimensions of the micro-channels 210, 410 may vary at discrete steps, for example, from width A, width B, width C, and width D, etc. For example, widths A, B, C, and D may decrease, or increase sequentially, or may vary with any pattern. Note that the physical gradient of the micro-channels 210, 410 are different from the chemo-gradient. There is no chemo-gradient between the set of reservoirs 120, 420, e.g., the input reservoir and the output reservoir.

In some embodiments, the micro-channels 210, 410 may have a cross-section ranging from 3 by 3 $\mu m^2$ to 20 by 20 $\mu m^2$. In some embodiments, the micro-channels 210, 410 may have a cross-section 5 by 5 $\mu m^2$. In some embodiments, the micro-channels 210, 410 may have a cross-section 10 by 10 $\mu m^2$. In some embodiments, the micro-channels 210, 410 may have a cross-section 15 by 15 $\mu m^2$. In some embodiments, the micro-channels 210, 410 may have a cross-section 3 by 5 $\mu m^2$. In some embodiments, the micro-channels 210, 410 may have a cross-section 3 by 10 $\mu m^2$. In some embodiments, the micro-channels 210, 410 may have a cross-section 5 by 10 $\mu m^2$. In some embodiments, the micro-channels 210, 410 may have a cross-section 5 by 15 $\mu m^2$. In some embodiments, the micro-channels 210, 410 may have varying lengths, for example, the length of the micro-channels 210, 410 may vary from 100 μm to 2 mm long. One of the micro-channels 210, 410 may have a different length from another one of the micro-channels 210, 410.

In some embodiments, the micro-channels 210, 410 may have a length ranging from 100 μm to 2.0 mm. In some embodiments, the micro-channels 210, 410 may have a length equal to or greater than 100 μm. In some embodiments, the micro-channels 210, 410 may have a length equal to or greater than 200 μm. In some embodiments, the micro-channels 210, 410 may have a length equal to or greater than 300 μm. In some embodiments, the micro-channels 210, 410 may have a length equal to or greater than 400 μm. In some embodiments, the micro-channels 210, 410 may have a length equal to or greater than 500 μm. In some embodiments, the micro-channels 210, 410 may have a length equal to or greater than 600 μm. In some embodiments, the micro-channels 210, 410 may have a length equal to or greater than 700 μm. In some embodiments, the micro-channels 210, 410 may have a length equal to or greater than 800 μm. In some embodiments, the micro-channels 210, 410 may have a length equal to or greater than 900 μm. In some embodiments, the micro-channels 210, 410 may have a length equal to or greater than 1.0 mm. In some embodiments, the micro-channels 210, 410 may have a length equal to or greater than 1.5 mm.

In some embodiments, the micro-channels 210, 410 may have a length less than or equal to 2.0 mm. In some embodiments, the micro-channels 210, 410 may have a length less than or equal to 1.5 mm. In some embodiments, the micro-channels 210, 410 may have a length less than or equal to 1.0 mm. In some embodiments, the micro-channels 210, 410 may have a length less than or equal to 900 μm. In some embodiments, the micro-channels 210, 410 may have a length less than or equal to 800 μm. In some embodiments, the micro-channels 210, 410 may have a length less than or equal to 700 μm. In some embodiments, the micro-channels 210, 410 may have a length less than or equal to 600 μm. In some embodiments, the micro-channels 210, 410 may have a length less than or equal to 500 μm. In some embodiments, the micro-channels 210, 410 may have a length less than or equal to 400 μm. In some embodiments, the micro-channels 210, 410 may have a length less than or equal to 300 μm. In some embodiments, the micro-channels 210, 410 may have a length less than or equal to 200 μm.

A higher density of the micro-channels 210, 410 is preferable for higher throughput applications of the present inventive concept. In some embodiments, the micro-channels 210, 410 may form an array including 50 to 400 micro-channels. In some embodiments, the micro-channels 210, 410 may form an array including 50 or more of the micro-channels 210, 410. In some embodiments, the micro-channels 210, 410 may form an array including 100 or more of the micro-channels 210, 410. In some embodiments, the micro-channels 210, 410 may form an array including 150 or more of the micro-channels 210, 410. In some embodiments, the micro-channels 210, 410 may form an array including 200 or more of the micro-channels 210, 410. In some embodiments, the micro-channels 210, 410 may form an array including 250 or more of the micro-channels 210, 410. In some embodiments, the micro-channels 210, 410 may form an array including 300 or more of the micro-channels 210, 410. In some embodiments, the micro-channels 210, 410 may form an array including 350 or more of the micro-channels 210, 410. In some embodiments, the micro-channels 210, 410 may form an array including 240 micro-channels.

In some embodiments, the micro-channels 210, 410 may form an array including 400 or fewer of the micro-channels 210, 410. In some embodiments, the micro-channels 210, 410 may form an array including 350 or fewer of the micro-channels 210, 410. In some embodiments, the micro-channels 210, 410 may form an array including 300 or fewer of the micro-channels 210, 410. In some embodiments, the micro-channels 210, 410 may form an array including 250 or fewer of the micro-channels 210, 410. In some embodiments, the micro-channels 210, 410 may form an array including 200 or fewer of the micro-channels 210, 410. In some embodiments, the micro-channels 210, 410 may form an array including 150 or fewer of the micro-channels 210, 410. In some embodiments, the micro-channels 210, 410 may form an array including 100 or fewer of the micro-channels 210, 410.

It will be appreciated by those skilled in the art that the dimensions, shape, and/or number of the micro-channels 210, 410 may vary with applications.

In some embodiments, of the micro-channels 210, 410 can be coated with extracellular matrix (ECM) molecules and/or filled with cells to create a tumor tissue like micro-environment.

One of the benefits of the CMAP assemblies 100, 400 is the high density of the micro-channels 210, 410, e.g., 240 micro-channels in each well, in an industry standard format, e.g., ninety-six (96) wells, and a total 23,040 micro-channels per plate.

Fabrication of CMAP Assembly

A fabrication process 500 includes forming the top plate 102, 402 using cyclic olefin polymer (COP) or cyclic olefin co-polymer (COC) of a black color. In this manner, laser welding of the top plate 102, 402 can be facilitated and artifact-free imaging due to reduced reflection and fluorescence can be obtained via the black COP. Using the black COP, the top plate 102, 402 is formed using an injection molding process, at operation 502. Injection molding is a manufacturing process for producing plastic parts by injecting molten material into a mold. For example, the mold may have the pattern of the top plate 102, 402, such as including the wells 106 and the reservoirs 120. COP pellets are fed into a heated barrel and injected into a mold cavity, where the COP cools down to form the top plate 102, 402.

Next, the fabrication process 500 includes forming the bottom plate 104, 404 using an optically clear COP, which provides an optically clear window when viewing cell migration through the micro-channels 210, 410 of the bottom plate 104, 404. In this manner, the bottom plate 104, 404 enables inspection or imaging of cells migrating through the micro-channels 210, 410 and analysis of images to visualize cell migrations. Using the optically clear COC/COP, the bottom plate 104, 404 is formed using a hot embossing process, at operation 504. The hot embossing process, which is a process of structuring polymer films or sheets by pressing a stamp into the polymer while the polymer is heated about its glass transition temperature. The polymer is much thicker than the height of the stamp structures. The relief is a perturbation of the total thickness of the polymer. Hot embossing is less prone to defects than nanoimprint lithography and is not limited to nano-structures or micro-structures. First, a silicon master mold is created with the imprint of the desired trough sets 122, 422. SU-8 is a commonly-used epoxy-based negative photoresist. Each set of the trough sets 122, 422 includes the linear array of troughs 128, 428, e.g., two-hundred and forty (240) troughs. The silicon SU-8 master mold is produced using a lithography process of spin coating SU-8 photoresist on a silicon wafer and then by exposure to UV light in a mask aligner. Then, non-cross-linked photoresist is washed away. The silicone SU-8 master mold with features of each trough in the linear array of troughs 128, 428 is produced. The master mold can also be created by dry or wet etching the trough pattern on a silicon wafer. Next, negative stamps of silicone are produced by pouring and peeling silicone on silicon mater. In the final step, the bottom plate 104, 404 is fabricated by transferring or imprinting features on the silicone stamp onto plain sheets of COP by the hot embossing process. In some embodiments, the COP sheets may have a thickness ranging from 100 μm to 800 μm. In some embodiments, the COP sheets may have a thickness ranging from 100 μm to 400 μm. In some embodiments, the COP sheets may be 188 μm thick. In this manner, the bottom plate 104, 404 is micro-fabricated.

Next, the fabrication process 500 includes aligning the top plate 102, 402 and the bottom plate 104, 404, at operation 506. Once aligned, the top plate 102, 402 and the bottom plate 104, 404 are held by fixture and vacuum. For example, the top plate 102, 402 and the bottom plate 104, 404 can be aligned for precision positioning of the trough sets 122, 422 with respect to the divisional wall portions 204, 444, and then held under suction, via a vacuum, on a 3D automated translation stage system during a joining process, at operation 508.

The joining process includes joining or bonding the top plate 102, 402 and the bottom plate 104, 404 together to form the CMAP assembly 100, 400. The top plate 102, 402 and the bottom plate 104, 404 are joined or bonded together and fluidly sealed by a laser welding process at an interface or junction between the top plate 102, 402 and the bottom plate 104, 404 along peripheries of the set of reservoirs 120, 420 and the wells 106, 406, as further discussed hereafter.

Laser welding provides a number of advantages over other bonding processes such as gluing. Laser welding is faster than gluing and can also be used for automatic and large-scale processes. Further, bonding provided via glue generally has low throughput, and potential complications due to chemical interactions with cells. The laser welding process of the present inventive concept is automatic and faster, and therefore has higher throughput. Further, the laser welding process of the present inventive concept better ensures no leaks will form and does not require chemicals. Other attachment processes such as via a friction-fit engagement and/or gluing provides a number of advantages over welding. For instance, the top plate 102, 402 and the bottom plate 104, 404 can be joined together to form the CMAP assembly 100, 400 so that the top plate 102, 402 is selectively detachable from the bottom plate 104, 404. For example, the joining process may utilize a friction-fit engagement and/or a reusable adhesive to allow the user to selectively attach and detach the top plate 102, 402 from the bottom plate 104, 404. In this manner, the user is advantageously provided with direct access to the cells migrating through the micro-channels 210, 410, thereby allowing further testing and/or inspection.

Turning to FIG. 6A, the operation 506 to form the CMAP assembly 100 is illustrated. The top plate 102 and the bottom plate 104 are aligned and held under suction on a 3D automated translation stage system including translation stages during the laser welding process. Next, via the operation 508, a laser spot from a laser source 602 is focused on a first interface between the top plate 102 and the bottom plate 104. Using alignment markers as a reference on the bottom plate 104, the translation stages move in a fixed 2D pattern, with the laser source 602 activated, thereby causing the bottom plate 104 to be welded, joined, and secured to the top plate 102 along each periphery of the wells 106, in a square pattern. In this manner, the top plate 102 and the bottom plate 104 are fluidly sealed to each other, and the CMAP assembly 100, with the micro-channels 210, is formed.

Turning to FIG. 6B, the operation 506 to form the CMAP assembly 400 is illustrated. The top plate 402 and the bottom plate 404 are aligned and held under suction on a 3D automated translation stage system including translation stages during the laser welding process. Next, via the operation 508, a laser spot from a laser source 652 is focused on a first interface between the top plate 402 and the bottom plate 404. Using alignment markers as a reference on the bottom plate 404, the translation stages move in a fixed 2D pattern, with the laser source 652 activated, thereby causing the bottom plate 404 to be welded to the top plate 402 along each periphery of the wells 406, in a square pattern. Next, the laser spot from the laser source 652 is focused on a second interface between the top plate 402 and the bottom plate 404. Using alignment markers as a reference on the bottom plate 404, the translation stages move in another fixed 2D pattern with respect to the laser spot, thereby causing the bottom plate 404 to be further welded to the top plate 402 along each of the reservoir peripheries, in a square pattern. In this manner, the top plate 402 and the bottom plate 404 are fluidly sealed to each other, and the CMAP assembly 400, with the micro-channels 410, is formed.

Image Analysis for Visualization of Cell Migrations

The present inventive concept utilizes a Fluorescence, Bright Field, Phase Contrast, plus Differential Interference Contrast (DIC) microscopy. DIC is an optical microscopy imaging method based on the principle of optical interference. Polarized light is split into two beams before it illuminates the sample and combined after exiting it. The combined beams form an interference image which maps the optical thickness of the sample.

Turning to FIGS. 7A and 7B, cells in different stages of migration through different ones of the micro-channels 210 are illustrated, which are exemplary of fluorescence images. FIG. 7A illustrates the CMAP assembly 100, with a constant aspect ratio at various times in accordance with embodiments of the present inventive concept. FIG. 7A shows that cells move along the micro-channels 210, to different positions 702, 704, 706, and 708 at 0 hours, 3 hours, 6 hours, and 9 hours, respectively, from left to right, in the micro-channels 210, with fixed dimensions. These cells may be put into an input reservoir of the reservoirs 120 and enter the entry portion 224 of one or more troughs, at different times. In an embodiment, straight ones of the micro-channels 210 are 5(w)×5(h) or 5×10 μm. In an embodiment, segments of tapered ones of the micro-channels 210 are 20(w)×10(h), 15×10 μm, 10×10 μm, 8×10 μm and 5×10 μm, respectively.

FIG. 7B illustrates the CMAP assembly 100, with a varying aspect ratio at various times in accordance with embodiments of the present inventive concept. FIG. 7B shows that cells move along the micro-channels 210, to different positions 712, 714, 716, 718, 720, and 722 from left to right at 0 hours, 4 hours, 16 hours, 18 hours, 22 hours, and 25 hours, respectively, in the micro-channels 210, with varying dimensions. In an embodiment, straight ones of the micro-channels 210 are 5(w)×5(h) or 5×10 μm. In an embodiment, segments of tapered ones of the micro-channels 210 are 20(w)×10(h), 15×10 μm, 10×10 μm, 8×10 μm and 5×10 μm, respectively. Again, these cells may be put in the input reservoir of the reservoirs 120, and enter the entry portion 224 of one or more troughs, at different times.

Turning to FIGS. 8A-8D, fluorescence plus DIC images of DAPI-stained and dtomato labelled cells in different stages of migration through the micro-channels 210 are shown. Cell body fluorescence by dtomato or similar stains is endogenously produced by cells by genetically transfecting cells them. DAPI or 4′, 6-diamidino-2-phenylindole is a nuclear fluorescent stain used to improve visualization and imaging of cells with the CMAP assembly, 100, 400. FIG. 8A shows a cell body 908, which has moved from an input reservoir 802 of the reservoirs 120 to a position along one of the micro-channels 210. FIG. 8B shows a cell body 810, which has moved from the input reservoir 802 to a position along one of the micro-channels 210. FIG. 8C shows a magnified image of a cell body 812, which has moved to a position along one of the micro-channels 210. FIG. 8D shows five (5) cells 814 A-E, which have moved to various positions along a single one of the micro-channels 210. In this manner, migration of cells through the micro-channels 210 can be visualized. With this visualization, cell migration can be studied for various purposes such as screening various tumor drugs.

Cell Migration Assay Plates (CMAP) Assemblies for Cell Isolation and Retrieval

Turning to FIGS. 9A-10D, the Cell Migration Assay Plates (CMAP) assembly 900 is illustrated according to an embodiment of the present inventive concept. The CMAP assembly 900 is generally defined by a top plate 902 and a trough component 904.

As illustrated in FIGS. 9A-9D, the top plate 902 includes four (4) wells 906 extending entirely through the top plate 902. The wells 906 are arranged in an array 908 with two (2) rows and two (2) columns. Each of the wells 906 is defined by a perimeter sidewall 914 with a top end 916 spaced from a bottom end 918 of the perimeter sidewall 914. The perimeter sidewall 914 defines a set of reservoirs 920, e.g., a first reservoir 9202 and a second reservoir 9204, extending entirely through the top plate 902, thereby causing each of the wells 906 to be substantially bottomless.

Referring also to FIGS. 10A-10D, the trough component 904 includes four (4) trough sets 922 formed into a planar surface 924 on one side 426 of the trough component 904. Each set of the troughs sets 922 includes a linear array of troughs 928 that correspond to a respective one of the wells 906. Similar to each trough of the linear array of troughs 128, 428, each trough of the linear array of troughs 928 is defined by opposing sidewalls, a bottom wall extending between the sidewalls, and opposing end walls extending between the sidewalls. The opposing sidewalls, the bottom wall, and the end walls collectively define an elongated cavity for receiving one or more cells and/or drugs.

It is foreseen that the linear array of troughs 928 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 928 includes two-hundred and forty (240) troughs, with a cross-section of 5 μm×5 μm, and a length of 700 μm.

Each reservoir of the set of reservoirs 920 includes the perimeter sidewall 914 extending through the trough component 904. The top plate 902 includes a separation or divisional wall 944 extending between the set of reservoirs 920. In an embodiment, the divisional wall 944 separates the set of reservoirs 920 with a thickness of 500 μm. It is foreseen that the thickness of the divisional wall 944 may be greater or smaller without deviating from the scope of the present inventive concept. In at least one embodiment, the divisional wall 944 can taper such that a top end 916 of the divisional wall 944 opposite the bottom end 918 has a first thickness greater than a second thickness of the bottom end 918 of the divisional wall 944. In an embodiment, the first thickness of the top end 916 of the divisional wall 944 can be about 1 millimeter. In an embodiment, the second thickness of the bottom end 918 of the divisional wall 944 can be about 500 micrometers.

As illustrated in FIGS. 10B and 10D, when the top plate 902 and the trough component 904 are assembled to form the small format CMAP assembly 900, the planar surface 924 of the trough component 904 abuts the top plate 902 such that each reservoir of the set of reservoirs 920 and each of the wells 906 are sealed by the trough component 904 and micro-channels 910 are formed, which fluidly connect each reservoir of the set of reservoirs 920.

Similar to the micro-channels 210, 410, each of the micro-channels 910 include an entrance opening and an exit opening at opposite ends thereof to define a one-way direction of fluid communication between each reservoir of the set of reservoirs 920. Each of the micro-channels 910 are defined by a middle portion of each trough of the linear array of troughs 928 and a surface of the divisional wall portion 944, which functions as a micro-channel roof. On one side of the middle portion, an entry portion of each trough of the linear array of troughs 928 does not have the micro-channel roof and, therefore, remains open into a first one of the set of reservoirs 920, which is operable to function as a seeding or input reservoir. In this manner, the input reservoir can be used to temporarily contain a cell and guide the cell into a respective one of the micro-channels 910. On another side of the middle portion, an exit portion of each trough of the linear array of troughs 928 also does not have the micro-channel roof and, therefore, also remains open into a second one of the set of reservoirs 920, which is operable to function as an output reservoir. In this manner, the output reservoir can be used to receive the tumor cells after migration through one of the plurality of micro-channels. The entry portion and the exit portion advantageously provide an extra margin in case of misalignment between the linear array of troughs 928 and the divisional wall 944 during assembly of the top plate 902 and the trough component 904. In an embodiment, when properly aligned, each trough of the linear array of troughs 928 has a length of approximately 700 μm, and the entry portion and the exit portion respectively protrude approximately 100 μm past either side of the divisional wall portion 944, which has a thickness of approximately 500 μm. In an embodiment, the micro-channels 910 have varying lengths and/or cross-sections. For instance, it is foreseen that a width of the divisional wall portion 944 may be increased or decreased to respectively increase or decrease a length and/or cross-section of the micro-channels 910. In this manner, the top plate 902, and the trough component 904 are advantageously operable to function as microfluidic device plates that enable a user to interrogate migratory potential of cells such as tumor cells.

As illustrated, FIGS. 9A, 9B, 9C, and 9D respectively show top perspective, top, side, and bottom views of the top plate 902 of the small format CMAP assembly 900 prior to assembly to the trough component 904. FIGS. 10A and 100 illustrate the trough component 904 prior to assembly to the top plate 902, while FIGS. 10B and 10D illustrate the top plate 902 assembled with the trough component 904 such that the trough component 904 is positioned proximate to the bottom end 918 of the divisional wall 944 of the top plate 902. Accordingly, as shown in FIG. 10B, the troughs 928 of the trough component 904 span the divisional wall 944 between the first opening of the first reservoir 9202 and the second opening of the second reservoir 9204 such that the cells deposited in the first reservoir 9202 are operable to migrate towards the second reservoir 9204 via the plurality of troughs 928. In at least one embodiment, the trough component 904 can include a film that forms the plurality of troughs 928.

The CMAP assembly 900 can be designed with the micro-channels 910 of various geometries, such as varying lengths, varying widths, and/or varying heights, which advantageously allow testing of and experimentations with various types of tumor cells and/or drugs.

The micro-channel dimensions (e.g., cross-section and length) can be selected for a single cell migration assay or a collective cell migration assay. When one of the micro-channels 910 is wide and provides less physical confinement for cells, the one of the micro-channels 910 provides two-dimensional (2D) migration for the cells and the cells do not touch fewer than all, e.g., one or two surfaces of the sidewalls 930, 932, the bottom wall 934, and the surface of the divisional wall portion 944, which functions as the micro-channel roof. Conversely, when one of the micro-channels 910 is narrow and provides greater physical confinement for cells, the cells are forced to squeeze through the one of the micro-channels 910, for example, by touching all surfaces of the sidewalls 930, 932, the bottom wall 934, and the surface of the divisional wall portion 944, which functions as the micro-channel roof. In this manner, greater physical confinement of the one of the micro-channels 910 triggers three-dimensional (3D) mode of migration for cells.

The migration time of a cell in the micro-channels 910 may vary between different ones of the micro-channels 910 with different cross-section areas. For instance, if a same cell is caused to pass through a first one of the micro-channels 910 and a second one of the micro-channels 910, the cell may take more time to pass through the first one of the micro-channels 910 than the second one of the micro-channels 910 if the first one of the micro-channels 910 has a smaller cross-section area than the second one of the micro-channels 910. In some embodiments, tumor cells can migrate faster when their nucleus is totally confined (e.g., in the micro-channels 910), which can happen up to a limit of physical confinement, beyond which the cell migration becomes slower. The cells can use a completely different mode of migration when physically confined which can confer faster migration speed.

In some embodiments, the micro-channels 910 may have cross-section areas of a square shape, a rectangular shape, and/or a circular shape. Additionally, in some embodiments, the micro-channels 910 may have a constant or consistent cross-section area. Additionally, in some embodiments, the micro-channels 910 may have varying aspect ratios (e.g., a ratio of height 910H to width 910W) or varying heights and/or varying widths, for example, cross-section areas may vary along the length of a single one of the micro-channels 910. For example, the single micro-channel may start with a width 910W of 20 μm, then gradually contract to a width 910W of 15 μm, a width 910W of 10 μm, and a width 910W of 5 μm. With such a varying cross-section area, the single micro-channel is advantageously operable to test cells in multiple one of the micro-channels 910, e.g., four micro-channels, having widths 910W of 20 μm, 15 μm, 10 μm, and 5 μm, respectively.

Additionally, in some embodiments, the cross-sections of the micro-channels 910 may continuously decrease or at discrete steps, and/or may continuously increase or at discrete steps. Additionally, in some embodiments, the dimensions of the micro-channels 910 may vary at discrete steps, for example, from width A, width B, width C, and width D, etc. For example, widths A, B, C, and D may decrease, or increase sequentially, or may vary with any pattern. Note that the physical gradient of the micro-channels 910 are different from the chemo-gradient. There is no chemo-gradient between the set of reservoirs 920, e.g., the input reservoir and the output reservoir.

In some embodiments, the micro-channels 910 may have a cross-section (e.g., height 910H by width 910W) ranging from 3 by 3 μm2 to 20 by 20 μm2. In some embodiments, the micro-channels 910 may have a cross-section 5 by 5 μm2. In some embodiments, the micro-channels 910 may have a cross-section 10 by 10 μm2. In some embodiments, the micro-channels 910 may have a cross-section 15 by 15 μm2. In some embodiments, the micro-channels 910 may have a cross-section 3 by 5 μm2. In some embodiments, the micro-channels 910 may have a cross-section 3 by 10 μm2. In some embodiments, the micro-channels 910 may have a cross-section 5 by 10 μm2. In some embodiments, the micro-channels 910 may have a cross-section 5 by 15 μm2.

In some embodiments, the micro-channels 910 may be separated from one another by a distance 904W of about 10 μm. The distance 904W between the micro-channels 910 may vary without deviating from the scope of the inventive concept.

In some embodiments, the micro-channels 910 may have varying lengths, for example, the length of the micro-channels 910 may vary from 100 μm to 2 mm long. One of the micro-channels 910 may have a different length from another one of the micro-channels 910.

In some embodiments, the micro-channels 910 may have a length ranging from 100 μm to 2.0 mm. In some embodiments, the micro-channels 910 may have a length equal to or greater than 100 μm. In some embodiments, the micro-channels 910 may have a length equal to or greater than 200 μm. In some embodiments, the micro-channels 910 may have a length equal to or greater than 300 μm. In some embodiments, the micro-channels 910 may have a length equal to or greater than 400 μm. In some embodiments, the micro-channels 910 may have a length equal to or greater than 500 μm. In some embodiments, the micro-channels 910 may have a length equal to or greater than 600 μm. In some embodiments, the micro-channels 910 may have a length equal to or greater than 700 μm. In some embodiments, the micro-channels 910 may have a length between about 700 μm and about 1200 μm. In some embodiments, the micro-channels 910 may have a length equal to or greater than 800 μm. In some embodiments, the micro-channels 910 may have a length equal to or greater than 900 μm. In some embodiments, the micro-channels 910 may have a length equal to or greater than 1.0 mm. In some embodiments, the micro-channels 910 may have a length equal to or greater than 1.5 mm.

In some embodiments, the micro-channels 910 may have a length less than or equal to 2.0 mm. In some embodiments, the micro-channels 910 may have a length less than or equal to 1.5 mm. In some embodiments, the micro-channels 910 may have a length less than or equal to 1.0 mm. In some embodiments, the micro-channels 910 may have a length less than or equal to 900 μm. In some embodiments, the micro-channels 910 may have a length less than or equal to 800 μm. In some embodiments, the micro-channels 910 may have a length less than or equal to 700 μm. In some embodiments, the micro-channels 910 may have a length less than or equal to 600 μm. In some embodiments, the micro-channels 910 may have a length less than or equal to 500 μm. In some embodiments, the micro-channels 910 may have a length less than or equal to 400 μm. In some embodiments, the micro-channels 910 may have a length less than or equal to 300 μm. In some embodiments, the micro-channels 910 may have a length less than or equal to 200 μm.

A higher density of the micro-channels 910 is preferable for higher throughput applications of the present inventive concept. In some embodiments, the micro-channels 910 may form an array including 50 to 400 micro-channels 910. In some embodiments, the micro-channels 910 may form an array including 200 to 280 micro-channels 910. In some embodiments, the micro-channels 910 may form an array including 50 or more of the micro-channels 910. In some embodiments, the micro-channels 910 may form an array including 100 or more of the micro-channels 910. In some embodiments, the micro-channels 910 may form an array including 150 or more of the micro-channels 910. In some embodiments, the micro-channels 910 may form an array including 200 or more of the micro-channels 910. In some embodiments, the micro-channels 910 may form an array including 250 or more of the micro-channels 910. In some embodiments, the micro-channels 910 may form an array including 300 or more of the micro-channels 910. In some embodiments, the micro-channels 910 may form an array including 350 or more of the micro-channels 910. In some embodiments, the micro-channels 910 may form an array including 290 micro-channels. In some embodiments, the micro-channels 910 may form an array including about 240 micro-channels.

In some embodiments, the micro-channels 910 may form an array including 400 or fewer of the micro-channels 910. In some embodiments, the micro-channels 910 may form an array including 350 or fewer of the micro-channels 910. In some embodiments, the micro-channels 910 may form an array including 300 or fewer of the micro-channels 910. In some embodiments, the micro-channels 910 may form an array including 250 or fewer of the micro-channels 910. In some embodiments, the micro-channels 910 may form an array including 200 or fewer of the micro-channels 910. In some embodiments, the micro-channels 910 may form an array including 150 or fewer of the micro-channels 910. In some embodiments, the micro-channels 910 may form an array including 100 or fewer of the micro-channels 910.

It will be appreciated by those skilled in the art that the dimensions, shape, and/or number of the micro-channels 910 may vary with applications.

In some embodiments, of the micro-channels 910 can be coated with extracellular matrix (ECM) molecules and/or filled with cells to create a tumor tissue like micro-environment.

One of the benefits of the CMAP assemblies 900 is the high density of the micro-channels 910, e.g., 240 micro-channels in each well, in an industry standard format, e.g., ninety-six (96) wells, and a total 23,090 micro-channels per plate.

Turning to FIG. 11, fluorescence plus DIC images of DAPI-stained cell nuclie 1100 in different stages of migration through the micro-channels 910 of the trough sets 922 are shown. DAPI or 4', 6-diamidino-2-phenylindole is a fluorescent stain used to improve visualization and imaging of cells 1100 with the CMAP assembly 900. FIG. 11 shows a plurality of cells 1100 which have moved from an input reservoir 9202 of the reservoirs 920 towards an output reservoir 9204 via the troughs 928 to a position along one of the micro-channels 910. In this manner, migration of cells 1100 through the micro-channels 910 can be visualized. With this visualization, cell migration can be studied for various purposes such as screening various tumor drugs. Additionally, referring also to FIG. 9D, the trough component 904 can be at least partially transparent so that the cells 1100 can be visualized during the process of cell migration. Accordingly, the user can determine whether the cells 1100 are ready to be removed from the micro-channels 910.

FIGS. 12A-13, 14A-140, and 15A-15B illustrate three examples of a CMAP assembly 1200, 1400, 1500 where at least a portion of the trough component 1204, 1404, 1504 is reconfigurable in relation to the top plate 1202, 1402, 1502 such that the plurality of troughs 1228, 1428, 1528 is exposed to permit a user to retrieve on or more of the plurality of cells from the troughs 1228, 1428, 1528. By being able to retrieve the cells that have been isolated while migrating across the troughs 1228, 1428, 1528, individual cells can be preserved and examined. Features in each of the CMAP assemblies 900, 1200, 1300, 1400, 1500 with similar reference numbers (e.g., 920, 1220, 1320, 1420, 1520) may correspond with one another, and also may correspond with similar reference numbers for CMAP assemblies 200, 400. In some examples, the features between examples may be interchanged without deviating from the scope of the present inventive concept. Additionally, the components, dimensions, quantity, configuration, etc. of the top plate 902 and the trough component 904 as discussed above with FIGS. 9A-10D can correspond with the features of the CMAP assemblies 1200, 1400, 1500 as illustrated in FIGS. 12A-15B. Turning to FIGS. 12A-12E, the Cell Migration Assay Plates (CMAP) assembly 1200 is illustrated according to an embodiment of the present inventive concept. The CMAP assembly 1200 is generally defined by a top plate 1202, a trough component 1204, and a sealing component 1250.

As illustrated in FIGS. 12A, 12C, 12D, and 12E, the top plate 1202 includes four (4) wells 1206 extending entirely through the top plate 1202. The wells 1206 are arranged in an array 1208 with two (2) rows and two (2) columns. Each of the wells 1206 is defined by a perimeter sidewall 1214 with a top end 1216 spaced from a bottom end 1218 of the perimeter sidewall 1214. The perimeter sidewall 1214 defines a set of reservoirs 1220, e.g., a first reservoir 12202 and a second reservoir 12204, extending entirely through the top plate 1202, thereby causing each of the wells 1206 to be substantially bottomless.

Referring to FIGS. 12C-12E, the trough component 1204 includes four (4) trough sets 1222 formed into a planar surface 1224 on one side 426 of the trough component 1204. Each set of the troughs sets 1222 includes a linear array of troughs 1228 that correspond to a respective one of the wells 1206. Similar to each trough of the linear array of troughs 128, 428, each trough of the linear array of troughs 1228 is defined by opposing sidewalls, a bottom wall extending between the sidewalls, and opposing end walls extending between the sidewalls. The opposing sidewalls, the bottom wall, and the end walls collectively define an elongated cavity for receiving one or more cells and/or drugs.

It is foreseen that the linear array of troughs 1228 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 1228 includes two-hundred and forty (240) troughs, with a cross-section of 5 μm×5 μm, and a length of 700 μm.

Each reservoir of the set of reservoirs 1220 includes the perimeter sidewall 1214 extending through the trough component 1204. The top plate 1202 includes a separation or divisional wall 1244 extending between the set of reservoirs 1220. In an embodiment, the divisional wall 1244 separates the set of reservoirs 1220 with a thickness of 500 μm. It is foreseen that the thickness of the divisional wall 1244 may be greater or smaller without deviating from the scope of the present inventive concept. In at least one embodiment, the divisional wall 1244 can taper such that a top end 1216 of the divisional wall 1244 opposite the bottom end 1218 has a first thickness greater than a second thickness of the bottom end 1218 of the divisional wall 1244. In an embodiment, the first thickness of the top end 1216 of the divisional wall 1244 can be about 1 millimeter. In an embodiment, the second thickness of the bottom end 1218 of the divisional wall 1244 can be about 500 micrometers.

As illustrated in FIGS. 12D and 12E, when the top plate 1202 and the trough component 1204 are assembled to form the small format CMAP assembly 1200, the planar surface 1224 of the trough component 1204 abuts the top plate 1202 such that each reservoir of the set of reservoirs 1220 and each of the wells 1206 are sealed by the trough component 1204 and micro-channels 1210 are formed, which fluidly connect each reservoir of the set of reservoirs 1220.

Similar to the micro-channels 210, 410, 910, each of the micro-channels 1210 include an entrance opening and an exit opening at opposite ends thereof to define a one-way direction of fluid communication between each reservoir of the set of reservoirs 1220. Each of the micro-channels 1210 are defined by a middle portion of each trough of the linear array of troughs 1228 and a surface of the divisional wall portion 1244, which functions as a micro-channel roof. On one side of the middle portion, an entry portion of each trough of the linear array of troughs 1228 does not have the micro-channel roof and, therefore, remains open into a first one of the set of reservoirs 1220, which is operable to function as a seeding or input reservoir. In this manner, the input reservoir can be used to temporarily contain a cell and guide the cell into a respective one of the micro-channels 1210. On another side of the middle portion, an exit portion of each trough of the linear array of troughs 1228 also does not have the micro-channel roof and, therefore, also remains open into a second one of the set of reservoirs 1220, which is operable to function as an output reservoir. In this manner, the output reservoir can be used to receive the tumor cells after migration through one of the plurality of micro-channels. The entry portion and the exit portion advantageously provide an extra margin in case of misalignment between the linear array of troughs 1228 and the divisional wall 1244 during assembly of the top plate 1202 and the trough component 1204. In an embodiment, when properly aligned, each trough of the linear array of troughs 1228 has a length of approximately 700 μm, and the entry portion and the exit portion respectively protrude approximately 100 μm past either side of the divisional wall portion 1244, which has a thickness of approximately 500 μm. In an embodiment, the micro-channels 1210 have varying lengths and/or cross-sections. For instance, it is foreseen that a width of the divisional wall portion 1244 may be increased or decreased to respectively increase or decrease a length and/or cross-section of the micro-channels 1210. In this manner, the top plate 1202, and the trough component 1204 are advantageously operable to function as microfluidic device plates that enable a user to interrogate migratory potential of cells such as tumor cells.

As illustrated, FIGS. 12A, 12B, and 12C respectively show top perspective, top, side, and bottom views of the top plate 1202 of the small format CMAP assembly 1200 prior to assembly to the trough component 1204. FIGS. 12D and 12E illustrate the top plate 1202 assembled with the trough component 1204 such that the trough component 1204 is positioned proximate to the bottom end 1218 of the divisional wall 1244 of the top plate 1202. Accordingly, as shown in FIGS. 12D and 12E, the troughs 1228 of the trough component 1204 span the divisional wall 1244 between the first opening 122020 of the first reservoir 12202 and the second opening 122040 of the second reservoir 12204 such that the cells deposited in the first reservoir 12202 are operable to migrate towards the second reservoir 12204 via the plurality of troughs 1228. In at least one embodiment, the trough component 904 can include a film that forms the plurality of troughs 928.

The CMAP assembly 1200 can be designed with the micro-channels 1210 of various geometries, such as varying lengths, varying widths, and/or varying heights, which advantageously allow testing of and experimentations with various types of tumor cells and/or drugs.

The micro-channel dimensions (e.g., cross-section and length) can be selected for a single cell migration assay or a collective cell migration assay. When one of the micro-channels 1210 is wide and provides less physical confinement for cells, the one of the micro-channels 1210 provides two-dimensional (2D) migration for the cells and the cells do not touch fewer than all, e.g., one or two surfaces of the sidewalls 1230, 1232, the bottom wall 1234, and the surface of the divisional wall portion 1244, which functions as the micro-channel roof. Conversely, when one of the micro-channels 1210 is narrow and provides greater physical confinement for cells, the cells are forced to squeeze through the one of the micro-channels 1210, for example, by touching all surfaces of the sidewalls 1230, 1232, the bottom wall 1234, and the surface of the divisional wall portion 1244, which functions as the micro-channel roof. In this manner, greater physical confinement of the one of the micro-channels 1210 provides three-dimensional (3D) migration for cells.

The migration time of a cell in the micro-channels 1210 may vary between different ones of the micro-channels 1210 with different cross-section areas. For instance, if a same cell is caused to pass through a first one of the micro-channels 1210 and a second one of the micro-channels 1210, the cell may take more time to pass through the first one of the micro-channels 1210 than the second one of the micro-channels 1210 if the first one of the micro-channels 1210 has a smaller cross-section area than the second one of the micro-channels 1210. In some embodiments, tumor cells can migrate faster when their nucleus is totally confined (e.g., in the micro-channels 1210), which can happen up to a limit of physical confinement, beyond which the cell migration becomes slower. The cells can use a completely different mode of migration when physically confined which can confer faster migration speed.

In some embodiments, the micro-channels 1210 may have cross-section areas of a square shape, a rectangular shape, and/or a circular shape. Additionally, in some embodiments, the micro-channels 1210 may have a constant or consistent cross-section area. Additionally, in some embodiments, the micro-channels 1210 may have varying aspect ratios (e.g., a ratio of height 1210H to width 1210W) or varying heights and/or varying widths, for example, cross-section areas may vary along the length of a single one of the micro-channels 1210. For example, the single micro-channel may start with a width 1210W of 20 μm, then gradually contract to a width 1210W of 15 μm, a width 1210W of 10 μm, and a width 1210W of 5 μm. With such a varying cross-section area, the single micro-channel is advantageously operable to test cells in multiple one of the micro-channels 1210, e.g., four micro-channels, having widths 1210W of 20 μm, 15 μm, 10 μm, and 5 μm, respectively.

Additionally, in some embodiments, the cross-sections of the micro-channels 1210 may continuously decrease or at discrete steps, and/or may continuously increase or at discrete steps. Additionally, in some embodiments, the dimensions of the micro-channels 1210 may vary at discrete steps, for example, from width A, width B, width C, and width D, etc. For example, widths A, B, C, and D may decrease, or increase sequentially, or may vary with any pattern. Note that the physical gradient of the micro-channels 1210 are different from the chemo-gradient. There is no chemo-gradient between the set of reservoirs 1220, e.g., the input reservoir and the output reservoir.

In some embodiments, the micro-channels 1210 may have a cross-section (e.g., height 1210H by width 1210W) ranging from 3 by 3 μm2 to 20 by 20 μm2. In some embodiments, the micro-channels 1210 may have a cross-section 5 by 5 μm2. In some embodiments, the micro-channels 1210 may have a cross-section 10 by 10 μm2. In some embodiments, the micro-channels 1210 may have a cross-section 15 by 15 μm2. In some embodiments, the micro-channels 1210 may have a cross-section 3 by 5 μm2. In some embodiments, the micro-channels 1210 may have a cross-section 3 by 10 μm2. In some embodiments, the micro-channels 1210 may have a cross-section 5 by 10 μm2. In some embodiments, the micro-channels 1210 may have a cross-section 5 by 15 μm2.

In some embodiments, the micro-channels 1210 may be separated from one another by a distance 1204W of about 10 μm. The distance 1204W between the micro-channels 1210 may vary without deviating from the scope of the inventive concept.

In some embodiments, the micro-channels 1210 may have varying lengths, for example, the length of the micro-channels 1210 may vary from 100 μm to 2 mm long. One of the micro-channels 1210 may have a different length from another one of the micro-channels 1210.

In some embodiments, the micro-channels 1210 may have a length ranging from 100 μm to 2.0 mm. In some embodiments, the micro-channels 1210 may have a length equal to or greater than 100 μm. In some embodiments, the micro-channels 1210 may have a length equal to or greater than 200 μm. In some embodiments, the micro-channels 1210 may have a length equal to or greater than 300 μm. In some embodiments, the micro-channels 1210 may have a length equal to or greater than 400 μm. In some embodiments, the micro-channels 1210 may have a length equal to or greater than 500 μm. In some embodiments, the micro-channels 1210 may have a length equal to or greater than 600 μm. In some embodiments, the micro-channels 1210 may have a length equal to or greater than 700 μm. In some embodiments, the micro-channels 1210 may have a length between about 700 μm and about 1200 μm. In some embodiments, the micro-channels 1210 may have a length equal to or greater than 800 μm. In some embodiments, the micro-channels 1210 may have a length equal to or greater than 1200 μm. In some embodiments, the micro-channels 1210 may have a length equal to or greater than 1.0 mm. In some embodiments, the micro-channels 1210 may have a length equal to or greater than 1.5 mm.

In some embodiments, the micro-channels 1210 may have a length less than or equal to 2.0 mm. In some embodiments, the micro-channels 1210 may have a length less than or equal to 1.5 mm. In some embodiments, the micro-channels 1210 may have a length less than or equal to 1.0 mm. In some embodiments, the micro-channels 1210 may have a length less than or equal to 1200 μm. In some embodiments, the micro-channels 1210 may have a length less than or equal to 800 μm. In some embodiments, the micro-channels 1210 may have a length less than or equal to 700 μm. In some embodiments, the micro-channels 1210 may have a length less than or equal to 600 μm. In some embodiments, the micro-channels 1210 may have a length less than or equal to 500 μm. In some embodiments, the micro-channels 1210 may have a length less than or equal to 400 μm. In some embodiments, the micro-channels 1210 may have a length less than or equal to 300 μm. In some embodiments, the micro-channels 1210 may have a length less than or equal to 200 μm.

A higher density of the micro-channels 1210 is preferable for higher throughput applications of the present inventive concept. In some embodiments, the micro-channels 1210 may form an array including 50 to 400 micro-channels 1210. In some embodiments, the micro-channels 1210 may form an array including 200 to 280 micro-channels 1210. In some embodiments, the micro-channels 1210 may form an array including 50 or more of the micro-channels 1210. In some embodiments, the micro-channels 1210 may form an array including 100 or more of the micro-channels 1210. In some embodiments, the micro-channels 1210 may form an array including 150 or more of the micro-channels 1210. In some embodiments, the micro-channels 1210 may form an array including 200 or more of the micro-channels 1210. In some embodiments, the micro-channels 1210 may form an array including 250 or more of the micro-channels 1210. In some embodiments, the micro-channels 1210 may form an array including 300 or more of the micro-channels 1210. In some embodiments, the micro-channels 1210 may form an array including 350 or more of the micro-channels 1210. In some embodiments, the micro-channels 1210 may form an array including 2120 micro-channels. In some embodiments, the micro-channels 1210 may form an array including about 240 micro-channels.

In some embodiments, the micro-channels 1210 may form an array including 400 or fewer of the micro-channels 1210. In some embodiments, the micro-channels 1210 may form an array including 350 or fewer of the micro-channels 1210. In some embodiments, the micro-channels 1210 may form an array including 300 or fewer of the micro-channels 1210. In some embodiments, the micro-channels 1210 may form an array including 250 or fewer of the micro-channels 1210. In some embodiments, the micro-channels 1210 may form an array including 200 or fewer of the micro-channels 1210. In some embodiments, the micro-channels 1210 may form an array including 150 or fewer of the micro-channels 1210. In some embodiments, the micro-channels 1210 may form an array including 100 or fewer of the micro-channels 1210.

It will be appreciated by those skilled in the art that the dimensions, shape, and/or number of the micro-channels 1210 may vary with applications.

In some embodiments, of the micro-channels 1210 can be coated with extracellular matrix (ECM) molecules and/or filled with cells to create a tumor tissue like micro-environment.

One of the benefits of the CMAP assemblies 1200 is the high density of the micro-channels 1210, e.g., 2120 micro-channels in each well, in an industry standard format, e.g., ninety-six (126) wells, and a total 23,0120 micro-channels per plate.

As illustrated in FIGS. 12A-12E, the CMAP assembly 1200 includes a sealing component 1250 operable to retain the cells and/or fluid within the desired sections (e.g., the reservoirs 1220, the troughs 1228, etc.). The sealing component 1250 includes a trough gasket 1251 which is operable to be positioned against the bottom end 1218 of the well 1206 such that the sealing component 1250 is sandwiched between the divisional wall 1244 and the trough component 1204. The trough gasket 1251 can be operable to retain the cells within the troughs 1228 such that the plurality of cells migrating towards the second reservoir 1220 are isolated within the corresponding troughs 1228.

The alignment and seal provided by the sealing component 1250 (e.g., the trough gasket 1251) is critical to maintaining the cells within the troughs 1228. During testing, it was determined that without the sealing component 1250, a gap may be formed between a top of the trough 1228 and the bottom end 1218 of the divisional wall 1244. Accordingly, cells would escape out of the top of the troughs 1228, and the individual cells were not isolated. Additionally, it was determined that maintaining position of the top plate 1202, the sealing component 1250, and the trough component 1204 is critical to achieve a successful seal to maintain isolation of the cells within the troughs 1228. Due to the microscopic size of the individual cells, it cannot be determined whether the desired seal has been achieved until the experiment begins. Accordingly, it is imperative that the desired position of the sealing component 1250 and the pressure on the sealing component 1250 is realized.

The bottom end 1218 of the top plate 1202 can form a gasket recess 1252 operable to receive the trough gasket 1251. The gasket recess 1252 can have a corresponding shape and size to the trough gasket 1251 to assist in aligning the trough gasket 1251 and maintaining position of the trough gasket 1251 in relation to the top plate 1202 and the trough component 1204.

As illustrated in FIG. 12B, the trough gasket 1251 can have a central portion 12500 and two end portions 12502 on opposing sides of the central portion 12500. The central portion 12500 can be substantially linear while the two end portions 12502 can be substantially cylindrical. In some embodiments, the central portion 12500 can be substantially circular or oval. In some examples, the central portion 12500 can be substantially rectangular. In some examples, the two end portions 12502 can be substantially rectangular. In some examples, the end portions 12502 can be substantially pyramidal. The shape of the central portion 12500 and the end portions 12502 can vary without deviating from the scope of the inventive concept.

The length 1250L of the trough gasket 1251 can be between about 2 millimeters and about 8 millimeters. In some embodiments, the length 1250L can be between about 3 millimeters and about 5 millimeters. In some embodiments, the length 1250L can be about 4.8 millimeters. The trough gasket 1251 can have varying lengths 1250L without deviating from the scope of the inventive concept so long as the trough gasket 1251 spans the plurality of troughs 1228.

The width 12502W of the end portions 12502 can be between 0.3 millimeters and about 1.5 millimeters. In some embodiments, the width 12502W of the end portions 12502 can be between about 0.5 millimeters and about 1 millimeter. In some embodiments, the width 12502W of the end portions 12502 can be about 0.83 millimeters. The width 12502W of the end portions 12502 can be greater than a width of the central portion 12500. Accordingly, the position of the trough gasket 1251 within the gasket recess 1252 can be better ensured.

Additionally, referring also to FIGS. 12C and 12D, the trough component 1204 can be at least partially transparent so that the cells 1100 can be visualized during the process of cell migration. With this visualization, cell migration can be studied for various purposes such as screening various tumor drugs. Accordingly, the user can determine whether the cells are ready to be removed from the micro-channels 1210.

In at least one embodiment, the sealing component 1250 is operable to retain the cells within the first reservoir 1220 and/or the second reservoir 1220 except via the plurality of troughs 1228. Accordingly, the sealing component 1250 can also provide a seal around each reservoir 1220. Along with the trough gasket 1251, the sealing component 1250 can then ensure that the cells are retained in either the reservoirs 1220 and/or the troughs 1228. As illustrated in FIG. 12E, the sealing component 1250 can include laser welding a pattern 1260 of the trough component 1204 to the top plate 1202. As illustrated in FIG. 12E, the pattern 1260 can surround the reservoirs 1220 and the trough gasket 1251. The pattern 1260 can be substantially rectangular. The pattern 1260 can form a grid. When the trough component 1204 is laser welded to the top plate 1202, the position of the trough component 1204 with the top plate 1202 is maintained.

To permit a user to retrieve the isolated cells within the micro-channels 1210 of the troughs 1228, at least a portion of the trough component 1204 is reconfigurable in relation to the trough gasket 1251 and the top plate 1202 such that the plurality of troughs 1228 is exposed. For example, the portion of the trough component 1204 with the troughs 1228 can be separated from the trough gasket 1251 and the top plate 1202. In at least one embodiment, for example as illustrated in FIG. 12E where the sealing component 1250 includes laser welding the trough component 1204 to the top plate 1202, the trough component 1204 may be cut to remove the portion of the trough component 1204 from the trough gasket 1251 and the top plate 1202. For example, FIG. 13 illustrates a cutting tool 1300 operable to cut the trough component 1204 of the CMAP assembly 1200. The cutting component 1300 can include a cutting assembly 1302 which includes die cut blades 1306 operable to cut the trough component 1204. The die cut blades 1306 can be shaped to cut the trough component 1204 adjacent to the pattern 1260 of the laser welding so that the portion of the trough component 1204 including the plurality of troughs 1228 is separable from the trough gasket 1251 and the top plate 1202. In at least one embodiment, the cutting assembly 1302 can include a push block 1304 operable to be used to enact a force onto the CMAP assembly 1200 so that the trough component 1204 is pressed against the die cut blades 1306 to be cut.

Turning to FIGS. 14A-14C, the Cell Migration Assay Plates (CMAP) assembly 1400 is illustrated according to an embodiment of the present inventive concept. The CMAP assembly 1400 is generally defined by a top plate 1402, a trough component 1404, and a sealing component 1450.

As illustrated in FIGS. 14A-14C, the top plate 1402 includes four (4) wells 1406 extending entirely through the top plate 1402. The wells 1406 are arranged in an array 1408 with two (2) rows and two (2) columns. Each of the wells 1406 is defined by a perimeter sidewall 1414 with a top end 1416 spaced from a bottom end 1418 of the perimeter sidewall 1414. The perimeter sidewall 1414 defines a set of reservoirs 1420, e.g., a first reservoir 14202 and a second reservoir 14204, extending entirely through the top plate 1402, thereby causing each of the wells 1406 to be substantially bottomless.

Referring to FIG. 14A, the trough component 1404 includes four (4) trough sets 1422 formed into a planar surface 1424 on one side 426 of the trough component 1404. Each set of the troughs sets 1422 includes a linear array of troughs 1428 that correspond to a respective one of the wells 1406. Similar to each trough of the linear array of troughs 148, 428, each trough of the linear array of troughs 1428 is defined by opposing sidewalls, a bottom wall extending between the sidewalls, and opposing end walls extending between the sidewalls. The opposing sidewalls, the bottom wall, and the end walls collectively define an elongated cavity for receiving one or more cells and/or drugs.

It is foreseen that the linear array of troughs 1428 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 1428 includes two-hundred and forty (240) troughs, with a cross-section of 5 μm×5 μm, and a length of 700 μm.

Each reservoir of the set of reservoirs 1420 includes the perimeter sidewall 1414 extending through the trough component 1404. The top plate 1402 includes a separation or divisional wall 1444 extending between the set of reservoirs 1420. In an embodiment, the divisional wall 1444 separates the set of reservoirs 1420 with a thickness of 500 μm. It is foreseen that the thickness of the divisional wall 1444 may be greater or smaller without deviating from the scope of the present inventive concept. In at least one embodiment, the divisional wall 1444 can taper such that a top end 1416 of the divisional wall 1444 opposite the bottom end 1418 has a first thickness greater than a second thickness of the bottom end 1418 of the divisional wall 1444. In an embodiment, the first thickness of the top end 1416 of the divisional wall 1444 can be about 1 millimeter. In an embodiment, the second thickness of the bottom end 1418 of the divisional wall 1444 can be about 500 micrometers.

As illustrated in FIG. 14B, when the top plate 1402 and the trough component 1404 are assembled to form the small format CMAP assembly 1400, the planar surface 1424 of the trough component 1404 abuts the top plate 1402 such that each reservoir of the set of reservoirs 1420 and each of the wells 1406 are sealed by the trough component 1404 and micro-channels 1410 are formed, which fluidly connect each reservoir of the set of reservoirs 1420.

Similar to the micro-channels 210, 410, 910, each of the micro-channels 1410 include an entrance opening and an exit opening at opposite ends thereof to define a one-way direction of fluid communication between each reservoir of the set of reservoirs 1420. Each of the micro-channels 1410 are defined by a middle portion of each trough of the linear array of troughs 1428 and a surface of the divisional wall portion 1444, which functions as a micro-channel roof. On one side of the middle portion, an entry portion of each trough of the linear array of troughs 1428 does not have the micro-channel roof and, therefore, remains open into a first one of the set of reservoirs 1420, which is operable to function as a seeding or input reservoir. In this manner, the input reservoir can be used to temporarily contain a cell and guide the cell into a respective one of the micro-channels 1410. On another side of the middle portion, an exit portion of each trough of the linear array of troughs 1428 also does not have the micro-channel roof and, therefore, also remains open into a second one of the set of reservoirs 1420, which is operable to function as an output reservoir. In this manner, the output reservoir can be used to receive the tumor cells after migration through one of the plurality of micro-channels. The entry portion and the exit portion advantageously provide an extra margin in case of misalignment between the linear array of troughs 1428 and the divisional wall 1444 during assembly of the top plate 1402 and the trough component 1404. In an embodiment, when properly aligned, each trough of the linear array of troughs 1428 has a length of approximately 700 μm, and the entry portion and the exit portion respectively protrude approximately 100 μm past either side of the divisional wall portion 1444, which has a thickness of approximately 500 μm. In an embodiment, the micro-channels 1410 have varying lengths and/or cross-sections. For instance, it is foreseen that a width of the divisional wall portion 1444 may be increased or decreased to respectively increase or decrease a length and/or cross-section of the micro-channels 1410. In this manner, the top plate 1402, and the trough component 1404 are advantageously operable to function as microfluidic device plates that enable a user to interrogate migratory potential of cells such as tumor cells.

As illustrated, FIGS. 14A and 14C respectively show the top plate 1402 of the small format CMAP assembly 1400 prior to assembly to the trough component 1404. FIG. 14B illustrates the top plate 1402 assembled with the trough component 1404 such that the trough component 1404 is positioned proximate to the bottom end 1418 of the divisional wall 1444 of the top plate 1402. Accordingly, the troughs 1428 of the trough component 1404 span the divisional wall 1444 between the first opening of the first reservoir 14202 and the second opening of the second reservoir 14204 such that the cells deposited in the first reservoir 14202 are operable to migrate towards the second reservoir 14204 via the plurality of troughs 1428. In at least one embodiment, the trough component 904 can include a film that forms the plurality of troughs 928.

The CMAP assembly 1400 can be designed with the micro-channels 1410 of various geometries, such as varying lengths, varying widths, and/or varying heights, which advantageously allow testing of and experimentations with various types of tumor cells and/or drugs.

The micro-channel dimensions (e.g., cross-section and length) can be selected for a single cell migration assay or a collective cell migration assay. When one of the micro-channels 1410 is wide and provides less physical confinement for cells, the one of the micro-channels 1410 provides two-dimensional (2D) migration for the cells and the cells do not touch fewer than all, e.g., one or two surfaces of the sidewalls 1430, 1432, the bottom wall 1434, and the surface of the divisional wall portion 1444, which functions as the micro-channel roof. Conversely, when one of the micro-channels 1410 is narrow and provides greater physical confinement for cells, the cells are forced to squeeze through the one of the micro-channels 1410, for example, by touching all surfaces of the sidewalls 1430, 1432, the bottom wall 1434, and the surface of the divisional wall portion 1444, which functions as the micro-channel roof. In this manner, greater physical confinement of the one of the micro-channels 1410 provides three-dimensional (3D) migration for cells.

The migration time of a cell in the micro-channels 1410 may vary between different ones of the micro-channels 1410 with different cross-section areas. For instance, if a same cell is caused to pass through a first one of the micro-channels 1410 and a second one of the micro-channels 1410, the cell may take more time to pass through the first one of the micro-channels 1410 than the second one of the micro-channels 1410 if the first one of the micro-channels 1410 has a smaller cross-section area than the second one of the micro-channels 1410. In some embodiments, tumor cells can migrate faster when their nucleus is totally confined (e.g., in the micro-channels 1410), which can happen up to a limit of physical confinement, beyond which the cell migration becomes slower. The cells can use a completely different mode of migration when physically confined which can confer faster migration speed.

In some embodiments, the micro-channels 1410 may have cross-section areas of a square shape, a rectangular shape, and/or a circular shape. Additionally, in some embodiments, the micro-channels 1410 may have a constant or consistent cross-section area. Additionally, in some embodiments, the micro-channels 1410 may have varying aspect ratios (e.g., a ratio of height 1410H to width 1410W) or varying heights and/or varying widths, for example, cross-section areas may vary along the length of a single one of the micro-channels 1410. For example, the single micro-channel may start with a width 1410W of 20 μm, then gradually contract to a width 1410W of 15 μm, a width 1410W of 10 μm, and a width 1410W of 5 μm. With such a varying cross-section area, the single micro-channel is advantageously operable to test cells in multiple one of the micro-channels 1410, e.g., four micro-channels, having widths 1410W of 20 μm, 15 μm, 10 μm, and 5 μm, respectively.

Additionally, in some embodiments, the cross-sections of the micro-channels 1410 may continuously decrease or at discrete steps, and/or may continuously increase or at discrete steps. Additionally, in some embodiments, the dimensions of the micro-channels 1410 may vary at discrete steps, for example, from width A, width B, width C, and width D, etc. For example, widths A, B, C, and D may decrease, or increase sequentially, or may vary with any pattern. Note that the physical gradient of the micro-channels 1410 are different from the chemo-gradient. There is no chemo-gradient between the set of reservoirs 1420, e.g., the input reservoir and the output reservoir.

In some embodiments, the micro-channels 1410 may have a cross-section (e.g., height 1410H by width 1410W) ranging from 3 by 3 μm2 to 20 by 20 μm2. In some embodiments, the micro-channels 1410 may have a cross-section 5 by 5 μm2. In some embodiments, the micro-channels 1410 may have a cross-section 10 by 10 μm2. In some embodiments, the micro-channels 1410 may have a cross-section 15 by 15 μm2. In some embodiments, the micro-channels 1410 may have a cross-section 3 by 5 μm2. In some embodiments, the micro-channels 1410 may have a cross-section 3 by 10 μm2. In some embodiments, the micro-channels 1410 may have a cross-section 5 by 10 μm2. In some embodiments, the micro-channels 1410 may have a cross-section 5 by 15 μm2.

In some embodiments, the micro-channels 1410 may be separated from one another by a distance 1404W of about 10 μm. The distance 1404W between the micro-channels 1410 may vary without deviating from the scope of the inventive concept.

In some embodiments, the micro-channels 1410 may have varying lengths, for example, the length of the micro-channels 1410 may vary from 100 μm to 2 mm long. One of the micro-channels 1410 may have a different length from another one of the micro-channels 1410.

In some embodiments, the micro-channels 1410 may have a length ranging from 100 μm to 2.0 mm. In some embodiments, the micro-channels 1410 may have a length equal to or greater than 100 μm. In some embodiments, the micro-channels 1410 may have a length equal to or greater than 200 μm. In some embodiments, the micro-channels 1410 may have a length equal to or greater than 300 μm. In some embodiments, the micro-channels 1410 may have a length equal to or greater than 400 μm. In some embodiments, the micro-channels 1410 may have a length equal to or greater than 500 μm. In some embodiments, the micro-channels 1410 may have a length equal to or greater than 600 μm. In some embodiments, the micro-channels 1410 may have a length equal to or greater than 700 μm. In some embodiments, the micro-channels 1410 may have a length between about 700 μm and about 1400 μm. In some embodiments, the micro-channels 1410 may have a length equal to or greater than 800 μm. In some embodiments, the micro-channels 1410 may have a length equal to or greater than 1400 μm. In some embodiments, the micro-channels 1410 may have a length equal to or greater than 1.0 mm. In some embodiments, the micro-channels 1410 may have a length equal to or greater than 1.5 mm.

In some embodiments, the micro-channels 1410 may have a length less than or equal to 2.0 mm. In some embodiments, the micro-channels 1410 may have a length less than or equal to 1.5 mm. In some embodiments, the micro-channels 1410 may have a length less than or equal to 1.0 mm. In some embodiments, the micro-channels 1410 may have a length less than or equal to 1400 μm. In some embodiments, the micro-channels 1410 may have a length less than or equal to 800 μm. In some embodiments, the micro-channels 1410 may have a length less than or equal to 700 μm. In some embodiments, the micro-channels 1410 may have a length less than or equal to 600 μm. In some embodiments, the micro-channels 1410 may have a length less than or equal to 500 μm. In some embodiments, the micro-channels 1410 may have a length less than or equal to 400 μm. In some embodiments, the micro-channels 1410 may have a length less than or equal to 300 μm. In some embodiments, the micro-channels 1410 may have a length less than or equal to 200 μm.

A higher density of the micro-channels 1410 is preferable for higher throughput applications of the present inventive concept. In some embodiments, the micro-channels 1410 may form an array including 50 to 400 micro-channels 1410. In some embodiments, the micro-channels 1410 may form an array including 200 to 280 micro-channels 1410. In some embodiments, the micro-channels 1410 may form an array including 50 or more of the micro-channels 1410. In some embodiments, the micro-channels 1410 may form an array including 100 or more of the micro-channels 1410. In some embodiments, the micro-channels 1410 may form an array including 150 or more of the micro-channels 1410. In some embodiments, the micro-channels 1410 may form an array including 200 or more of the micro-channels 1410. In some embodiments, the micro-channels 1410 may form an array including 250 or more of the micro-channels 1410. In some embodiments, the micro-channels 1410 may form an array including 300 or more of the micro-channels 1410. In some embodiments, the micro-channels 1410 may form an array including 350 or more of the micro-channels 1410. In some embodiments, the micro-channels 1410 may form an array including 2140 micro-channels. In some embodiments, the micro-channels 1410 may form an array including about 240 micro-channels.

In some embodiments, the micro-channels 1410 may form an array including 400 or fewer of the micro-channels 1410. In some embodiments, the micro-channels 1410 may form an array including 350 or fewer of the micro-channels 1410. In some embodiments, the micro-channels 1410 may form an array including 300 or fewer of the micro-channels 1410. In some embodiments, the micro-channels 1410 may form an array including 250 or fewer of the micro-channels 1410. In some embodiments, the micro-channels 1410 may form an array including 200 or fewer of the micro-channels 1410. In some embodiments, the micro-channels 1410 may form an array including 150 or fewer of the micro-channels 1410. In some embodiments, the micro-channels 1410 may form an array including 100 or fewer of the micro-channels 1410.

It will be appreciated by those skilled in the art that the dimensions, shape, and/or number of the micro-channels 1410 may vary with applications.

In some embodiments, of the micro-channels 1410 can be coated with extracellular matrix (ECM) molecules and/or filled with cells to create a tumor tissue like micro-environment.

One of the benefits of the CMAP assemblies 1400 is the high density of the micro-channels 1410, e.g., 2140 micro-channels in each well, in an industry standard format, e.g., ninety-six (146) wells, and a total 23,0140 micro-channels per plate.

As illustrated in FIG. 14A, the CMAP assembly 1400 includes a sealing component 1450 operable to retain the cells and/or fluid within the desired sections (e.g., the reservoirs 1420, the troughs 1428, etc.). The sealing component 1450 includes a trough gasket 1451 which is operable to be positioned against the bottom end 1418 of the well 1406 such that the sealing component 1450 is sandwiched between the divisional wall 1444 and the trough component 1404. The trough gasket 1451 can be operable to retain the cells within the troughs 1428 such that the plurality of cells migrating towards the second reservoir 1420 are isolated within the corresponding troughs 1428.

The alignment and seal provided by the sealing component 1450 (e.g., the trough gasket 1451) is critical to maintaining the cells within the troughs 1428. During testing, it was determined that without the sealing component 1450, a gap may be formed between a top of the trough 1428 and the bottom end 1418 of the divisional wall 1444. Accordingly, cells would escape out of the top of the troughs 1428, and the individual cells were not isolated. Additionally, it was determined that maintaining position of the top plate 1402, the sealing component 1450, and the trough component 1404 is critical to achieve a successful seal to maintain isolation of the cells within the troughs 1428. Due to the microscopic size of the individual cells, it cannot be determined whether the desired seal has been achieved until the experiment begins. Accordingly, it is imperative that the desired position of the sealing component 1450 and the pressure on the sealing component 1450 is realized.

The bottom end 1418 of the top plate 1402 can form a gasket recess 1452 operable to receive the trough gasket 1451. The gasket recess 1452 can have a corresponding shape and size to the trough gasket 1451 to assist in aligning the trough gasket 1451 and maintaining position of the trough gasket 1451 in relation to the top plate 1402 and the trough component 1404.

Additionally, the trough component 1404 can be at least partially transparent so that the cells 1100 can be visualized during the process of cell migration. With this visualization, cell migration can be studied for various purposes such as screening various tumor drugs. Accordingly, the user can determine whether the cells are ready to be removed from the micro-channels 1410.

In at least one embodiment, the sealing component 1450 is operable to retain the cells within the first reservoir 1420 and/or the second reservoir 1420 except via the plurality of troughs 1428. Accordingly, the sealing component 1450 can also provide a seal around each reservoir 1420. Along with the trough gasket 1451, the sealing component 1450 can then ensure that the cells are retained in either the reservoirs 1420 and/or the troughs 1428. As illustrated in FIG. 14A, the sealing component 1450 can include a grid gasket 1460. As illustrated in FIG. 14A, the grid gasket 1460 can surround the reservoirs 1420 and the trough gasket 1451. In at least one embodiment, the grid gasket 1460 can be separate from the trough gasket 1451. In some embodiments, the grid gasket 1460 can be integral with the trough gasket 1451. The grid gasket 1460 can be substantially rectangular. The grid gasket 1460 can form a grid to form a seal around each of the first reservoir 14202, the second reservoir 14204, and the trough gasket 1451. When the trough component 1404 is positioned against the top plate 1402 sandwiching the grid gasket 1460, the position of the trough component 1404 with the top plate 1402 is maintained.

In at least one embodiment, as illustrated in FIGS. 14A-14C, the CMAP assembly 1400 can include an alignment plate 1480 operable to receive the trough component 1404 and the top plate 1402. Accordingly, the arrangement of the CMAP assembly 1400 can be the top plate 1402, the sealing component 1450, the trough component 1404, and the alignment plate 1480. The alignment plate 1480 can include a receiving portion 1482 operable to receive the trough component 1404 to ensure alignment and positioning of the trough component 1404. The receiving portion 1482 can form a recess to receive the trough component 1404. In at least one embodiment, the receiving portion 1482 of the alignment plate 1480 can be at least partially transparent to permit visualization of the cells migrating in the trough component 1404.

In some embodiments, to ensure the alignment and maintain positioning of the top plate 1402, the sealing component 1450, and the trough component 1404, the alignment plate 1480 can include alignment walls 1494. The alignment walls 1494 can extend from the alignment plate 1480 and abut against the top plate 1402. The alignment walls 1494 form a space to receive the top plate 1402 such that the top plate 1402 can only be positioned in the desired alignment. Also, the alignment walls 1494 can maintain the position of the top plate 1402 by preventing movement and/or rotation of the top plate 1402 in relation to the alignment plate 1480.

In some embodiments, the alignment plate 1480 can include at least two pins 1492 extending therefrom. The top plate 1402 can include at least two receiving portions 1490 operable to receive the corresponding pins 1492 to align the top plate 1402, the trough component 1404, and the alignment plate 1480. In at least one embodiment, as illustrated in FIG. 14C, the receiving portions 1490 can form holes have substantially frustoconical shapes. With the frustoconical shaped holes, the pins 1492 cannot be easily removed from the receiving portions 1490, ensuring the positioning of the top plate 1402.

To permit a user to retrieve the isolated cells within the micro-channels 1410 of the troughs 1428, at least a portion of the trough component 1404 is reconfigurable in relation to the trough gasket 1451 and the top plate 1402 such that the plurality of troughs 1428 is exposed. For example, the portion of the trough component 1404 with the troughs 1428 can be separated from the trough gasket 1451 and the top plate 1402. In at least one embodiment, for example as illustrated in FIG. 14C, the pins 1492 are operable to be removed from the receiving portions 1490 to decouple the alignment plate 1480 from the top plate 1402 such that the trough component is separable from the top plate 1402.

Turning to FIGS. 15A-15B, the Cell Migration Assay Plates (CMAP) assembly 1500 is illustrated according to an embodiment of the present inventive concept. The CMAP assembly 1500 is generally defined by a top plate 1502, a trough component 1504, and a sealing component 1550.

As illustrated in FIGS. 15A-15B, the top plate 1502 includes four (4) wells 1506 extending entirely through the top plate 1502. The wells 1506 are arranged in an array 1508 with two (2) rows and two (2) columns. Each of the wells 1506 is defined by a perimeter sidewall 1515 with a top end 1516 spaced from a bottom end 1518 of the perimeter sidewall 1515. The perimeter sidewall 1515 defines a set of reservoirs 1520, e.g., a first reservoir 15202 and a second reservoir 15204, extending entirely through the top plate 1502, thereby causing each of the wells 1506 to be substantially bottomless.

Referring to FIG. 15B, the trough component 1504 includes four (4) trough sets 1522 formed into a planar surface 1524 on one side 426 of the trough component 1504. Each set of the troughs sets 1522 includes a linear array of troughs 1528 that correspond to a respective one of the wells 1506. Similar to each trough of the linear array of troughs 158, 428, each trough of the linear array of troughs 1528 is defined by opposing sidewalls, a bottom wall extending between the sidewalls, and opposing end walls extending between the sidewalls. The opposing sidewalls, the bottom wall, and the end walls collectively define an elongated cavity for receiving one or more cells and/or drugs.

It is foreseen that the linear array of troughs 1528 may include any number of troughs, with different ones of the troughs being of different shapes and/or sizes, without deviating from the scope of the present inventive concept. Indeed, the number, size, and shape of troughs shown by the figures are merely for illustrative purposes for understanding the present inventive concept. In an embodiment, the linear array of troughs 1528 includes two-hundred and forty (240) troughs, with a cross-section of 5 µm×5 µm, and a length of 700 µm.

Each reservoir of the set of reservoirs 1520 includes the perimeter sidewall 1515 extending through the trough component 1504. The top plate 1502 includes a separation or divisional wall 1544 extending between the set of reservoirs 1520. In an embodiment, the divisional wall 1544 separates the set of reservoirs 1520 with a thickness of 500 µm. It is foreseen that the thickness of the divisional wall 1544 may be greater or smaller without deviating from the scope of the present inventive concept. In at least one embodiment, the divisional wall 1544 can taper such that a top end 1516 of the divisional wall 1544 opposite the bottom end 1518 has a first thickness greater than a second thickness of the bottom end 1518 of the divisional wall 1544. In an embodiment, the first thickness of the top end 1516 of the divisional wall 1544 can be about 1 millimeter. In an embodiment, the second thickness of the bottom end 1518 of the divisional wall 1544 can be about 500 micrometers.

As illustrated in FIG. 15A, when the top plate 1502 and the trough component 1504 are assembled to form the small format CMAP assembly 1500, the planar surface 1524 of the trough component 1504 abuts the top plate 1502 such that each reservoir of the set of reservoirs 1520 and each of the wells 1506 are sealed by the trough component 1504 and micro-channels 1510 are formed, which fluidly connect each reservoir of the set of reservoirs 1520.

Similar to the micro-channels 210, 410, 910, each of the micro-channels 1510 include an entrance opening and an exit opening at opposite ends thereof to define a one-way direction of fluid communication between each reservoir of the set of reservoirs 1520. Each of the micro-channels 1510 are defined by a middle portion of each trough of the linear array of troughs 1528 and a surface of the divisional wall portion 1544, which functions as a micro-channel roof. On one side of the middle portion, an entry portion of each trough of the linear array of troughs 1528 does not have the micro-channel roof and, therefore, remains open into a first one of the set of reservoirs 1520, which is operable to function as a seeding or input reservoir. In this manner, the input reservoir can be used to temporarily contain a cell and guide the cell into a respective one of the micro-channels 1510. On another side of the middle portion, an exit portion of each trough of the linear array of troughs 1528 also does not have the micro-channel roof and, therefore, also remains open into a second one of the set of reservoirs 1520, which is operable to function as an output reservoir. In this manner, the output reservoir can be used to receive the tumor cells after migration through one of the plurality of micro-channels. The entry portion and the exit portion advantageously provide an extra margin in case of misalignment between the linear array of troughs 1528 and the divisional wall 1544 during assembly of the top plate 1502 and the trough component 1504. In an embodiment, when properly aligned, each trough of the linear array of troughs 1528 has a length of approximately 700 μm, and the entry portion and the exit portion respectively protrude approximately 100 μm past either side of the divisional wall portion 1544, which has a thickness of approximately 500 μm. In an embodiment, the micro-channels 1510 have varying lengths and/or cross-sections. For instance, it is foreseen that a width of the divisional wall portion 1544 may be increased or decreased to respectively increase or decrease a length and/or cross-section of the micro-channels 1510. In this manner, the top plate 1502, and the trough component 1504 are advantageously operable to function as microfluidic device plates that enable a user to interrogate migratory potential of cells such as tumor cells.

As illustrated, FIG. 15A shows the top plate 1502 of the small format CMAP assembly 1500 prior to assembly to the trough component 1504. FIG. 15B illustrates the top plate 1502 assembled with the trough component 1504 such that the trough component 1504 is positioned proximate to the bottom end 1518 of the divisional wall 1544 of the top plate 1502. Accordingly, the troughs 1528 of the trough component 1504 span the divisional wall 1544 between the first opening of the first reservoir 15202 and the second opening of the second reservoir 15204 such that the cells deposited in the first reservoir 15202 are operable to migrate towards the second reservoir 15204 via the plurality of troughs 1528. In at least one embodiment, the trough component 904 can include a film that forms the plurality of troughs 928.

The CMAP assembly 1500 can be designed with the micro-channels 1510 of various geometries, such as varying lengths, varying widths, and/or varying heights, which advantageously allow testing of and experimentations with various types of tumor cells and/or drugs.

The micro-channel dimensions (e.g., cross-section and length) can be selected for a single cell migration assay or a collective cell migration assay. When one of the micro-channels 1510 is wide and provides less physical confinement for cells, the one of the micro-channels 1510 provides two-dimensional (2D) migration for the cells and the cells do not touch fewer than all, e.g., one or two surfaces of the sidewalls 1530, 1532, the bottom wall 1534, and the surface of the divisional wall portion 1544, which functions as the micro-channel roof. Conversely, when one of the micro-channels 1510 is narrow and provides greater physical confinement for cells, the cells are forced to squeeze through the one of the micro-channels 1510, for example, by touching all surfaces of the sidewalls 1530, 1532, the bottom wall 1534, and the surface of the divisional wall portion 1544, which functions as the micro-channel roof. In this manner, greater physical confinement of the one of the micro-channels 1510 provides three-dimensional (3D) migration for cells.

The migration time of a cell in the micro-channels 1510 may vary between different ones of the micro-channels 1510 with different cross-section areas. For instance, if a same cell is caused to pass through a first one of the micro-channels 1510 and a second one of the micro-channels 1510, the cell may take more time to pass through the first one of the micro-channels 1510 than the second one of the micro-channels 1510 if the first one of the micro-channels 1510 has a smaller cross-section area than the second one of the micro-channels 1510. In some embodiments, tumor cells can migrate faster when their nucleus is totally confined (e.g., in the micro-channels 1510), which can happen up to a limit of physical confinement, beyond which the cell migration becomes slower. The cells can use a completely different mode of migration when physically confined which can confer faster migration speed.

In some embodiments, the micro-channels 1510 may have cross-section areas of a square shape, a rectangular shape, and/or a circular shape. Additionally, in some embodiments, the micro-channels 1510 may have a constant or consistent cross-section area. Additionally, in some embodiments, the micro-channels 1510 may have varying aspect ratios (e.g., a ratio of height 1510H to width 1510W) or varying heights and/or varying widths, for example, cross-section areas may vary along the length of a single one of the micro-channels 1510. For example, the single micro-channel may start with a width 1510W of 20 μm, then gradually contract to a width 1510W of 15 μm, a width 1510W of 10 μm, and a width 1510W of 5 μm. With such a varying cross-section area, the single micro-channel is advantageously operable to test cells in multiple one of the micro-channels 1510, e.g., four micro-channels, having widths 1510W of 20 μm, 15 μm, 10 μm, and 5 μm, respectively.

Additionally, in some embodiments, the cross-sections of the micro-channels 1510 may continuously decrease or at discrete steps, and/or may continuously increase or at discrete steps. Additionally, in some embodiments, the dimensions of the micro-channels 1510 may vary at discrete steps, for example, from width A, width B, width C, and width D, etc. For example, widths A, B, C, and D may decrease, or increase sequentially, or may vary with any pattern. Note that the physical gradient of the micro-channels 1510 are different from the chemo-gradient. There is no chemo-gradient between the set of reservoirs 1520, e.g., the input reservoir and the output reservoir.

In some embodiments, the micro-channels 1510 may have a cross-section (e.g., height 1510H by width 1510W) ranging from 3 by 3 μm2 to 20 by 20 μm2. In some embodiments, the micro-channels 1510 may have a cross-section 5 by 5 μm2. In some embodiments, the micro-channels 1510 may have a cross-section 10 by 10 μm2. In some embodiments, the micro-channels 1510 may have a cross-section 15 by 15 μm2. In some embodiments, the micro-channels 1510 may have a cross-section 3 by 5 μm2. In some embodiments, the micro-channels 1510 may have a cross-section 3 by 10 μm2. In some embodiments, the micro-channels 1510 may have a cross-section 5 by 10 μm2. In some embodiments, the micro-channels 1510 may have a cross-section 5 by 15 μm2.

In some embodiments, the micro-channels 1510 may be separated from one another by a distance 1504W of about 10 μm. The distance 1504W between the micro-channels 1510 may vary without deviating from the scope of the inventive concept.

In some embodiments, the micro-channels 1510 may have varying lengths, for example, the length of the micro-channels 1510 may vary from 100 μm to 2 mm long. One of the micro-channels 1510 may have a different length from another one of the micro-channels 1510.

In some embodiments, the micro-channels 1510 may have a length ranging from 100 μm to 2.0 mm. In some embodiments, the micro-channels 1510 may have a length equal to or greater than 100 μm. In some embodiments, the micro-channels 1510 may have a length equal to or greater than 200 μm. In some embodiments, the micro-channels 1510 may have a length equal to or greater than 300 μm. In some embodiments, the micro-channels 1510 may have a length equal to or greater than 400 μm. In some embodiments, the micro-channels 1510 may have a length equal to or greater than 500 μm. In some embodiments, the micro-channels 1510 may have a length equal to or greater than 600 μm. In some embodiments, the micro-channels 1510 may have a length equal to or greater than 700 μm. In some embodiments, the micro-channels 1510 may have a length between about 700 μm and about 1500 μm. In some embodiments, the micro-channels 1510 may have a length equal to or greater than 800 μm. In some embodiments, the micro-channels 1510 may have a length equal to or greater than 1500 μm. In some embodiments, the micro-channels 1510 may have a length equal to or greater than 1.0 mm. In some embodiments, the micro-channels 1510 may have a length equal to or greater than 1.5 mm.

In some embodiments, the micro-channels 1510 may have a length less than or equal to 2.0 mm. In some embodiments, the micro-channels 1510 may have a length less than or equal to 1.5 mm. In some embodiments, the micro-channels 1510 may have a length less than or equal to 1.0 mm. In some embodiments, the micro-channels 1510 may have a length less than or equal to 1500 μm. In some embodiments, the micro-channels 1510 may have a length less than or equal to 800 μm. In some embodiments, the micro-channels 1510 may have a length less than or equal to 700 μm. In some embodiments, the micro-channels 1510 may have a length less than or equal to 600 μm. In some embodiments, the micro-channels 1510 may have a length less than or equal to 500 μm. In some embodiments, the micro-channels 1510 may have a length less than or equal to 400 μm. In some embodiments, the micro-channels 1510 may have a length less than or equal to 300 μm. In some embodiments, the micro-channels 1510 may have a length less than or equal to 200 μm.

A higher density of the micro-channels 1510 is preferable for higher throughput applications of the present inventive concept. In some embodiments, the micro-channels 1510 may form an array including 50 to 400 micro-channels 1510. In some embodiments, the micro-channels 1510 may form an array including 200 to 280 micro-channels 1510. In some embodiments, the micro-channels 1510 may form an array including 50 or more of the micro-channels 1510. In some embodiments, the micro-channels 1510 may form an array including 100 or more of the micro-channels 1510. In some embodiments, the micro-channels 1510 may form an array including 150 or more of the micro-channels 1510. In some embodiments, the micro-channels 1510 may form an array including 200 or more of the micro-channels 1510. In some embodiments, the micro-channels 1510 may form an array including 250 or more of the micro-channels 1510. In some embodiments, the micro-channels 1510 may form an array including 300 or more of the micro-channels 1510. In some embodiments, the micro-channels 1510 may form an array including 350 or more of the micro-channels 1510. In some embodiments, the micro-channels 1510 may form an array including 2150 micro-channels. In some embodiments, the micro-channels 1510 may form an array including about 240 micro-channels.

In some embodiments, the micro-channels 1510 may form an array including 400 or fewer of the micro-channels 1510. In some embodiments, the micro-channels 1510 may form an array including 350 or fewer of the micro-channels 1510. In some embodiments, the micro-channels 1510 may form an array including 300 or fewer of the micro-channels 1510. In some embodiments, the micro-channels 1510 may form an array including 250 or fewer of the micro-channels 1510. In some embodiments, the micro-channels 1510 may form an array including 200 or fewer of the micro-channels 1510. In some embodiments, the micro-channels 1510 may form an array including 150 or fewer of the micro-channels 1510. In some embodiments, the micro-channels 1510 may form an array including 100 or fewer of the micro-channels 1510.

It will be appreciated by those skilled in the art that the dimensions, shape, and/or number of the micro-channels 1510 may vary with applications.

In some embodiments, of the micro-channels 1510 can be coated with extracellular matrix (ECM) molecules and/or filled with cells to create a tumor tissue like micro-environment.

One of the benefits of the CMAP assemblies 1500 is the high density of the micro-channels 1510, e.g., 2150 micro-channels in each well, in an industry standard format, e.g., ninety-six (156) wells, and a total 23,0150 micro-channels per plate.

As illustrated in FIG. 15B, the CMAP assembly 1500 includes a sealing component 1550 operable to retain the cells and/or fluid within the desired sections (e.g., the reservoirs 1520, the troughs 1528, etc.). The sealing component 1550 includes a trough gasket 1551 which is operable to be positioned against the bottom end 1518 of the well 1506 such that the sealing component 1550 is sandwiched between the divisional wall 1544 and the trough component 1504. The trough gasket 1551 can be operable to retain the cells within the troughs 1528 such that the plurality of cells migrating towards the second reservoir 1520 are isolated within the corresponding troughs 1528.

The alignment and seal provided by the sealing component 1550 (e.g., the trough gasket 1551) is critical to maintaining the cells within the troughs 1528. During testing, it was determined that without the sealing component 1550, a gap may be formed between a top of the trough 1528 and the bottom end 1518 of the divisional wall 1544. Accordingly, cells would escape out of the top of the troughs 1528, and the individual cells were not isolated. Additionally, it was determined that maintaining position of the top plate 1502, the sealing component 1550, and the trough component 1504 is critical to achieve a successful seal to maintain isolation of the cells within the troughs 1528. Due to the microscopic size of the individual cells, it cannot be determined whether the desired seal has been achieved until the experiment begins. Accordingly, it is imperative that the desired position of the sealing component 1550 and the pressure on the sealing component 1550 is realized.

The bottom end 1518 of the top plate 1502 can form a gasket recess 1552 operable to receive the trough gasket 1551. The gasket recess 1552 can have a corresponding shape and size to the trough gasket 1551 to assist in aligning the trough gasket 1551 and maintaining position of the trough gasket 1551 in relation to the top plate 1502 and the trough component 1504.

Additionally, the trough component 1504 can be at least partially transparent so that the cells 1100 can be visualized during the process of cell migration. With this visualization, cell migration can be studied for various purposes such as screening various tumor drugs. Accordingly, the user can determine whether the cells are ready to be removed from the micro-channels 1510.

In at least one embodiment, the sealing component 1550 is operable to retain the cells within the first reservoir 1520 and/or the second reservoir 1520 except via the plurality of troughs 1528. Accordingly, the sealing component 1550 can also provide a seal around each reservoir 1520. Along with the trough gasket 1551, the sealing component 1550 can then ensure that the cells are retained in either the reservoirs 1520 and/or the troughs 1528. As illustrated in FIG. 15B, the sealing component 1550 can include a grid gasket 1560. As illustrated in FIG. 15B, the grid gasket 1560 can surround the reservoirs 1520 and the trough gasket 1551. In at least one embodiment, the grid gasket 1560 can be separate from the trough gasket 1551. In some embodiments, the grid gasket 1560 can be integral with the trough gasket 1551. The grid gasket 1560 can be substantially rectangular. The grid gasket 1560 can form a grid to form a seal around each of the first reservoir 15202, the second reservoir 15204, and the trough gasket 1551. When the trough component 1504 is positioned against the top plate 1502 sandwiching the grid gasket 1560, the position of the trough component 1504 with the top plate 1502 is maintained.

In at least one embodiment, as illustrated in FIGS. 15A-15B, the CMAP assembly 1500 can include clamp component 1503 operable to receive the trough component 1504 and the top plate 1502. The clamp component 1503 can be operable to compress the top plate 1502 and the trough component 1504 together and to hold the positioning of the top plate 1502 in relation to the trough component 1504. The clamp component 1503 is operable to compress the top plate 1502 and the trough component 1504 together so that the trough gasket 1551 maintains contact with the divisional wall 1544 and the troughs 1528. The clamp component 1503 can include a top component 1590 and a bottom component 1580. The top plate 1502, the seal component 1550, and the trough component 1504 can be provided between the top component 1590 and the bottom component 1580. Accordingly, the arrangement of the CMAP assembly 1500 can be the top component 1590, the top plate 1502, the sealing component 1550, the trough component 1504, and the bottom component 1580.

The bottom component 1580 of the clamp component 1503 can include a receiving portion 1582 operable to receive the trough component 1504 to ensure alignment and positioning of the trough component 1504. The receiving portion 1582 can form a recess to receive the trough component 1504. In at least one embodiment, the receiving portion 1582 of the alignment plate 1580 can be at least partially transparent to permit visualization of the cells migrating in the trough component 1504.

In some embodiments, to ensure the alignment and maintain positioning of the top plate 1502, the sealing component 1550, and the trough component 1504, the clamp component 1503 can include alignment features 1594, 1591 operable to receive a portion of the top plate 1502 to align the top plate 1502 with the clamp component 1503. The alignment features 1594, 1591 can include raised portions 1594 and/or recesses 1591. The raised portions 1594, as illustrated in FIGS. 15A and 15B, can extend from the bottom component 1580 and abut against the top plate 1502. In some embodiments, the raised portions 1594 can extend from the top component 1590. The raised portions 1593 form a space to receive the top plate 1502 such that the top plate 1502 can only be positioned in the desired alignment. Also, the raised portions 1593 can maintain the position of the top plate 1502 by preventing movement and/or rotation of the top plate 1502 in relation to the clamp component 1503. As illustrated in FIG. 15B, the top component 1590 can form a recess 1591 shaped and sized to receive the top plate 1502. When the top plate 1502 is received in the recess 1591, the top plate 1502 can only be positioned in the desired alignment. Also, the recess 1591 can maintain the position of the top plate 1502 by preventing movement and/or rotation of the top plate 1502 in relation to the clamp component 1503.

In at least one embodiment, as illustrated in FIG. 15B, the top component 1590 can form an aperture 1595 such that the wells 1506 of the top plate 1502 can extend through the aperture 1595. The aperture 1595, when receiving the wells 1506, maintains position and alignment of the top plate 1502 in relation to the clamp component 1503 by preventing movement and/or rotation of the top plate 1502 in relation to the clamp component 1503.

In some embodiments, the clamp component 1503 can include at least two screws 1592 operable to secure the top component 1590 to the bottom component 1580. Accordingly, the screws 1592 cannot be easily removed, ensuring the positioning of the top plate 1502, the sealing component 1550, and the trough component 1504 within the clamping component 1503. As the screws 1592 are tightened, the top component 1590 and the bottom component 1580 of the clamp component 1503 are brought closer together. When the top component 1590 and the bottom component 1580 are brought closer together, the sealing component 1550 (e.g., the trough gasket 1551) is compressed against the top plate 1502 and the trough component 1504, forming a tighter seal to maintain the cells within the troughs 1528.

To permit a user to retrieve the isolated cells within the micro-channels 1510 of the troughs 1528, at least a portion of the trough component 1504 is reconfigurable in relation to the trough gasket 1551 and the top plate 1502 such that the plurality of troughs 1528 is exposed. For example, the portion of the trough component 1504 with the troughs 1528 can be separated from the trough gasket 1551 and the top plate 1502. In at least one embodiment, for example as illustrated in FIG. 15B, the screws 1592 are operable to be removed from the clamp component 1503 to decouple the top component 1590 from the bottom component 1580. The clamp component 1503 can then be opened so that the trough component is separable from the top plate 1502.

Retrieval of the Cells

When the cells disposed in the troughs are exposed, the isolated cells can be detached from the troughs.

In at least one embodiment, ultrasound can be applied to the trough component to detach the one or more cells from the troughs. In at least one embodiment, a cell detachment medium can be provided to the one or more cells to detach the cells from the troughs. In an embodiment, the cell detachment medium can include accutase. Other mechanisms to detach the cells from the troughs can be utilized without deviating from the scope of the inventive concept.

Once the cells are detached from the troughs, the isolated cells can be retrieved.

Applications

Drug development is a time-consuming and prohibitively-expensive process. High failure rates of tumor drugs can be attributed, in part, to poor selectivity of drug molecules during in-vitro screening. The CMAP assembly 100, 400 significantly improves in-vitro drug screening sensitivity of tumor drugs.

The CMAP assembly 100, 400 facilitates drug screening applications where high throughput and high content capability are beneficial, for example, when a large library of drug molecules need to be screened. The CMAP assembly 100 with ninety-six (96) wells 106 is particularly designed to provide an optically clear bottom plate or window, enable high throughput, and be compatible with high content plate imagers for drug screening assays.

Cancer or tumor cells generally have a big nucleus, with a width varying from 5 μm to 50 μm. Cancer cells may squeeze through and migrate through the micro-channels 210, 410. However, an effective drug may block or stop the cancer or tumor cells from migrating through the micro-channels 210, 410. Indeed, various types of drugs can be tested with the cancer cells using the micro-channels 210, 410. If the drug prevents the cancer cells from migrating through the micro-channels 210, 410, such is indicative that the drug can cure cancer.

In some embodiments, cell culture protocols are provided. For instance, cell culture protocol may vary based on a number of factors including type of cells and/or type of assay. Or, cell culture protocol may be a single, generic cell culture protocol applicable regardless of any factors such as, but not limited to cell type and/or assay type. Cells can be cultured with drugs prior to drug testing in the CMAP assembly 100, 400. For example, with drug X tested along with cancer or tumor cells, the cells may only migrate half of a distance through the micro-channels 210, 410 relative to the cells' migration through the micro-channels 210, 410 without use of the drug X. With drug Y tested along with cancer or tumor cells, the cells may move a quarter of the distance through the micro-channels 210, 410 relative to the cells' migration through the micro-channels 210, 410 without use of the drug Y. As such, these tests demonstrate that the drug Y is more effective than the drug X to block movement of cancer or tumor cells within the micro-channels 210, 410. Therefore, drug Y may be more effective than drug X to cure cancer.

A drug may work well at the beginning to block cell migration through the micro-channels 210, 410, but may not work well later. As discussed herein, dimensions of a single one of the micro-channels 210, 410 can be designed to have reduced dimensions, for example, starting with a cross-section area of 20 by 20 μm2, which continually reduces to a cross-section area of 15 by 15 μm2, then to a cross-section area of 10 by 10 μm2, and finally to a cross-section area of 5 by 5 μm2. As such, the single one of the micro-channels 210, 410 is advantageously operable to yield a cell migration study in what would otherwise require four different ones of the micro-channels 210, 410.

The CMAP assembly 100, 400 have been used to test patient-derived glioma cells. In addition, migration tests with lung cancer cells and breast cancer cells have been conducted using the CMAP assembly 100, 400.

In some embodiments, the CMAP assembly 100, 400 can also be used as a diagnostic assay to score tumor invasion potential of individual patients. For example, different tumor cells may be tested. Tumor cells that demonstrate higher or quicker migration through the micro-channels 210, 410 of the CMAP assembly 100, 400 may be concluded to be more invasive to humans than tumor cells with lower or slower migration through the micro-channels 210, 410 of the CMAP assembly 100, 400.

Having described several embodiments, it will be recognized by those skilled in the art that various modifications, alternative constructions, and equivalents may be used without departing from the spirit of the present inventive concept. Additionally, a number of well-known processes and elements have not been described in order to avoid unnecessarily obscuring the present inventive concept. Accordingly, this description should not be taken as limiting the scope of the present inventive concept.

Those skilled in the art will appreciate that the presently disclosed embodiments teach by way of example and not by limitation. Therefore, the matter contained in this description or shown in the accompanying drawings should be interpreted as illustrative and not in a limiting sense. The following claims are intended to cover all generic and specific features described herein, as well as all statements of the scope of the method and assemblies, which, as a matter of language, might be said to fall therebetween.

What is claimed is:

1. A cell migration assay plates (CMAP) assembly comprising:

a top plate having a well with a bottom end, the well having a first reservoir and a second reservoir separated by a divisional wall, the divisional wall having a divisional bottom end, the first reservoir having a first opening at the bottom end, the second reservoir having a second opening at the bottom end;

a trough component operable to be positioned proximate to the divisional bottom end of the divisional wall of the top plate, the trough component including a plurality of troughs, the plurality of troughs spanning the divisional wall between the first opening of the first reservoir and the second opening of the second reservoir such that a plurality of cells deposited in the first reservoir are operable to migrate towards the second reservoir via the plurality of troughs; and a sealing component including a trough gasket operable to be positioned against the bottom end of the well such that the sealing component is sandwiched between the divisional wall and the trough component, the trough gasket operable to retain the plurality of cells within the plurality of troughs such that the plurality of cells migrating towards the second reservoir are isolated within each corresponding trough of the plurality of troughs, wherein at least a portion of the trough component is reconfigurable in relation to the trough gasket and the top plate such that the plurality of troughs is exposed to permit a user to retrieve one or more of the plurality of cells from the plurality of troughs.

2. The CMAP assembly of claim 1, wherein the trough gasket has a central portion and two end portions on opposing sides of the central portion, wherein the central portion is substantially linear while the two end portions are substantially circular or oval.

3. The CMAP assembly of claim 1, wherein the top plate includes a gasket recess operable to receive the trough gasket, wherein the gasket recess has a corresponding shape to the trough gasket to assist in aligning the trough gasket and maintaining position of the trough gasket in relation to the top plate and the trough component.

4. The CMAP assembly of claim 1, wherein the sealing component is operable to retain the plurality of cells within the first reservoir and/or the second reservoir except via the plurality of troughs.

5. The CMAP assembly of claim 4, wherein the sealing component includes a grid gasket such that the grid gasket forms a seal around each of the first reservoir, the second reservoir, and the trough gasket.

6. The CMAP assembly of claim 4, wherein the sealing component includes laser welding of the trough component to the top plate.

7. The CMAP assembly of claim 6, further comprising: one or more die cut blades operable to cut the trough component, the one or more die cut blades shaped to cut the trough component adjacent to the laser welding so that the portion of the trough component including the plurality of troughs is separable from the trough gasket and the top plate.

8. The CMAP assembly of claim 1, further comprising: a clamp component operable to compress the top plate and the trough component and to hold the positioning of the top plate in relation to the trough component.

9. The CMAP assembly of claim 8, wherein the clamp component is operable to compress the top plate and the trough component so that the trough gasket maintains contact with the divisional wall and the plurality of troughs.

10. The CMAP assembly of claim 9, wherein the clamp component is operable to be opened so that the trough component is separable from the top plate.

11. The CMAP assembly of claim 8, wherein the clamp component includes alignment features operable to receive a portion of the top plate to align the top plate with the clamp component.

12. The CMAP assembly of claim 11, wherein the alignment features include one or more raised portions and/or recesses.

13. The CMAP assembly of claim 8, wherein the clamp component includes a top component and a bottom component, wherein the top component is secured to the bottom component via screws.

14. The CMAP assembly of claim 13, wherein the bottom component includes a transparent portion such that the trough component is visible.

15. The CMAP assembly of claim 1, further comprising: an alignment plate operable to receive the trough component and the top plate.

16. The CMAP assembly of claim 15, wherein the alignment plate includes at least two pins extending therefrom, wherein the top plate includes at least two receiving portions operable to receive the corresponding at least two pins to align the top plate, the trough component, and the alignment plate.

17. The CMAP assembly of claim 16, wherein the at least two receiving portions form holes having a substantially frustoconical shape.

18. The CMAP assembly of claim 16, wherein the at least two pins are operable to be removed from the at least two receiving portions to decouple the alignment plate from the top plate such that the trough component is separable from the top plate.

19. The CMAP assembly of claim 1, wherein the divisional wall tapers such that a top end of the divisional wall opposite the divisional bottom end has a first thickness greater than a second thickness of the divisional bottom end of the divisional wall.

20. The CMAP assembly of claim 1, wherein the trough component includes a film that forms the plurality of troughs.

21. A method comprising:
providing a cell migration assay plate (CMAP) assembly, the CMAP including:
a top plate having a well with a bottom end, the well having a first reservoir and a second reservoir separated by a divisional wall, the divisional wall having a divisional bottom end, the first reservoir having a first opening at the bottom end, the second reservoir having a second opening at the bottom end;
a trough component operable to be positioned proximate to the divisional bottom end of the divisional wall of the top plate, the trough component including a plurality of troughs, the plurality of troughs spanning the divisional wall between the first opening of the first reservoir and the second opening of the second reservoir; and
a sealing component including a trough gasket operable to be positioned against the bottom end of the well such that the sealing component is sandwiched between the divisional wall and the trough component, the trough gasket operable to retain a plurality of cells within the plurality of troughs such that the plurality of cells migrating towards the second reservoir are isolated within each corresponding trough of the plurality of troughs;
depositing the plurality of cells into the first reservoir such that the plurality of cells migrate towards the second reservoir via the plurality of troughs;
exposing a set of troughs by reconfiguring at least a portion of the trough component in relation to the top plate; and
retrieving one or more cells of the plurality of cells disposed in the plurality of troughs.

22. The method of claim 21, wherein retrieving the one or more cells of the plurality of cells disposed in the plurality of troughs further includes:
applying ultrasound to the trough component to detach the one or more cells from the plurality of troughs.

23. The method of claim 21, wherein retrieving the one or more cells of the plurality of cells disposed in the plurality of troughs further includes:
providing a cell detachment medium to the one or more cells to detach the one or more cells from the plurality of troughs.

24. The method of claim 23, wherein the cell detachment medium includes accutase.

25. The method of claim 21, wherein exposing the set of troughs further includes:
cutting the trough component adjacent to laser welding so that the portion of the trough component including the plurality of troughs is separable from the trough gasket and the top plate.

26. The method of claim 21, wherein exposing the set of troughs further includes:
opening a clamp component so that the trough component is separable from the top plate.

27. The method of claim 21, wherein exposing the set of troughs further includes:

removing at least two pins of an alignment plate from at least two receiving portions of the top plate to decouple the alignment plate from the top plate such that the trough component is separable from the top plate.

* * * * *